United States Patent
Hunziker et al.

(10) Patent No.: US 9,493,486 B2
(45) Date of Patent: Nov. 15, 2016

(54) DIAZASPIROCYCLOALKANE AND AZASPIROCYCLOALKANE

(71) Applicant: Hoffmann-La Roche Inc., Little Falls, NJ (US)

(72) Inventors: Daniel Hunziker, Moehlin (CH); Patrizio Mattei, Riehen (CH); Harald Mauser, Riehen (CH); Marco Prunotto, Delémont (CH); Christoph Ullmer, Fischingen (DE)

(73) Assignee: Hoffmann-La Roches Inc., Little Falls, NJ (US)

( * ) Notice: Subject to any disclaimer, the term of this patent is extended or adjusted under 35 U.S.C. 154(b) by 0 days.

(21) Appl. No.: 14/569,564

(22) Filed: Dec. 12, 2014

(65) Prior Publication Data
US 2015/0099734 A1    Apr. 9, 2015

Related U.S. Application Data

(63) Continuation of application No. PCT/EP2013/061890, filed on Jun. 10, 2013.

(30) Foreign Application Priority Data

Jun. 13, 2012   (EP) ..................... 12171839

(51) Int. Cl.
| | | |
|---|---|---|
| C07D 519/00 | (2006.01) | |
| C07D 487/10 | (2006.01) | |
| C07D 205/12 | (2006.01) | |
| C07D 405/06 | (2006.01) | |
| C07D 405/12 | (2006.01) | |
| C07D 413/12 | (2006.01) | |
| C07D 249/18 | (2006.01) | |
| C07D 471/10 | (2006.01) | |
| C07D 403/12 | (2006.01) | |

(52) U.S. Cl.
CPC .......... C07D 519/00 (2013.01); C07D 205/12 (2013.01); C07D 249/18 (2013.01); C07D 403/12 (2013.01); C07D 405/06 (2013.01); C07D 405/12 (2013.01); C07D 413/12 (2013.01); C07D 471/10 (2013.01); C07D 487/10 (2013.01)

(58) Field of Classification Search
CPC   C07D 405/06; C07D 405/12; C07D 413/12; C07D 249/18; C07D 519/00; C07D 487/10; C07D 205/12; C07D 403/12; C07D 471/10
USPC .................. 546/16; 548/147, 216, 255, 953; 514/210.18, 210.17
See application file for complete search history.

(56) References Cited

U.S. PATENT DOCUMENTS

2010/0298290 A1   11/2010   Anand et al.

FOREIGN PATENT DOCUMENTS

| EP | 0 417 631 A2 | 3/1991 |
|---|---|---|
| EP | 2 301 936 A1 | 3/2011 |
| WO | 2005/040167 A1 | 5/2005 |
| WO | 2007/030061 A1 | 3/2007 |
| WO | 2008/033456 A1 | 3/2008 |
| WO | 2008/060767 A2 | 5/2008 |
| WO | 2009/046841 A2 | 4/2009 |
| WO | 2010/055006 A1 | 5/2010 |
| WO | 2010/115491 A2 | 10/2010 |
| WO | 2010/141817 A1 | 12/2010 |
| WO | 2011/114271 A1 | 9/2011 |
| WO | 2011/115813 A1 | 9/2011 |
| WO | 2013/033059 A1 | 3/2013 |
| WO | 2013/064467 A1 | 5/2013 |
| WO | 2013/065712 A1 | 5/2013 |

OTHER PUBLICATIONS

Litherland and Mann The amino derivatives of Pentaerythritol 1938.*
1206969-43-8,Database Registry [retrieved online May 25, 2016] Chemical Abstracts Service, Feb. 22, 2010, BroadPharm: XP002707619, retreived from STN Database accession No. 1206969-43-8 the whole document.
959567-58-9,Database Registry [retreived online May 25, 2016] Chemical Abstracts Service Dec. 26, 2007, NH Chemical Genomics Center: XP002707620,retreived from STN Database accession No. 959567-58-9.
Albers et al., "Chemical Evolution of Autotaxin Inhibitors" Chemical Reviews(XP055073234), 112(5):2593-2603 (May 9, 2012).
CAS Registry Database, 1300725-30-7,Database Registry [retreived online May 25, 2016] Chemical Abstracts Service May 25, 2011, Focus Synthesis LLC: XP002707618, retreived from STN Database accession No. 1300725-30-7 the whole document.
CAS Registry Database, 1352926-47-7,Database Registry [retreived online May 25, 2016] Chemical Abstracts Service Jan. 12, 2012, All i chem LLC: XP002707617, retrieved from STN Database accession No. 1352926-14-7 see also RN: 135295-74-6; the whole document.
ISR for PCT/EP2013/061890.
Kung et al., "Identification of spirocyclic piperidine-azetidine inverse agaonists of the ghrelin receptor" Bioorganic & Medicinal Chemistry Letters (XP028490993), 22(13): 4281-4287 (May 8, 2012).
Litherland et al., "The Amino-derivatives of Pentuerythritol. Part I. Preparation." (Published on Jan. 1, 1938. Downloaded by Roche Group on May 24, 2016 17:23:15.),:1588-1595.

(Continued)

*Primary Examiner* — Rita Desai
(74) *Attorney, Agent, or Firm* — Robert C. Hall

(57) ABSTRACT

The invention provides novel compounds having the general formula (I)

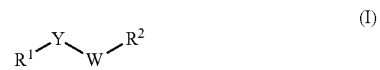

wherein $R^1$, $R^2$, Y and W are as described herein, compositions including the compounds and methods of using the compounds.

6 Claims, No Drawings

(56) References Cited

OTHER PUBLICATIONS

Orr et al., "One-pot synthesis of chiral azetidines from chloroaldehyde and chiral amines" Tetrahedron Letters (XP055073241), 52:3618-3620 (2011).

Overberger et al., "Absolute Configuration of 2,7-Diazaspiro-[4.4]nonane. A Reassignment" J. Org. Chem. (XP055072840), 46:2757-2764 (1981).
Stocks et al., "A Practical Method for Targeted Library Design Balancing Lead-like Properties with Diversity" Chem Med Chem (XP002707616), 4:800-808 (2009).
Written Opinion for PCT/EP2013/061890.

* cited by examiner

DIAZASPIROCYCLOALKANE AND AZASPIROCYCLOALKANE

PRIORITY OF INVENTION

This application claims priority under 35 U.S.C. 120 and 35 U.S.C. 365(c) to International Application Nos. PCT/EP2013/061890 filed on Jun. 10, 2013 and claims priority to 35 U.S.C. 119(a), to European Patent Application No. 1271839.9 filed on Jun. 13, 2012. The entire content of the applications referenced above are hereby incorporated by reference herein.

BACKGROUND OF INVENTION

Autotaxin (ATX) is a secreted enzyme also called ecto-nucleotide pyrophosphatase/phosphodiesterase 2 or lyso-phospholipase D that is important for converting lysophosphatidyl choline (LPC) to the bioactive signaling molecule lysophosphatidic acid (LPA). It has been shown that plasma LPA levels are well correlated with ATX activity and hence ATX is believed to be an important source of extracellular LPA. Early experiments with a prototype ATX inhibitor have shown that such a compound is able to inhibit the LPA synthesizing activity in mouse plasma. Work conducted in the 1970s and early 1980s has demonstrated that LPA can elicit a wide range of cellular response; including smooth muscle cell contraction, platelet activation, cell proliferation, chemotaxis and others. LPA mediates its effects via signaling to several G protein coupled receptors (GPCRs); the first members were originally denoted Edg (endothelial cell differentiation gene) receptors or ventricular zone gene-1(vzg-1) but are now called LPA receptors. The prototypic group now consists of LPA1/Edg-2/VZG-1, LPA2/Edg-4, and LPA3/Edg-7. Recently, three additional LPA receptors LPA4/p2y9/GPR23, LPAS/GPR92 and LPA6/p2Y5 have been described that are more closely related to nucleotide-selective purinergic receptors than to the prototypic LPA1-3 receptors. The ATX-LPA signaling axis is involved in a large range of physiological and pathophysiological functions, including, for example, nervous system function, vascular development, cardiovascular physiology, reproduction, immune system function, chronic inflammation, tumor metastasis and progression, organ fibrosis as well as obesity and/or other metabolic diseases such as diabetes mellitus. Therefore, increased activity of ATX and/or increased levels of LPA, altered LPA receptor expression and altered responses to LPA may contribute to the initiation, progression and/or outcome of a number of different pathophysiological conditions related to the ATX/LPA axis.

SUMMARY OF INVENTION

In one aspect, the present invention relates to organic compounds useful for therapy or prophylaxis in a mammal, and in particular to autotaxin (ATX) inhibitors which are inhibitors of lysophosphatidic acid (LPA) production and thus modulators of LPA levels and associated signaling, for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

The present invention provides novel compounds of formula (I)

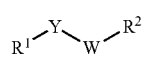

wherein $R^1$ is alkyl, haloalkyl, cycloalkyl, substituted phenyl, substituted phenylalkyl, substituted phenoxyalkyl, substituted phenylcycloalkyl, substituted phenylalkenyl, substituted phenylalkynyl, substituted pyridinyl, substituted pyridinylalkyl, substituted pyridinylalkenyl, substituted pyridinylalkynyl, substituted thiophenyl, substituted thiophenylalkyl, substituted thiophenylalkenyl, substituted thiophenylalkynyl, substituted 2,3-dihydro-1H-isoindol-2-yl, substituted 1H-indol-2-yl or substituted benzofuran-2-yl, wherein substituted phenyl, substituted phenylalkyl, substituted phenoxyalkyl, substituted phenylcycloalkyl, substituted phenylalkenyl, substituted phenylalkynyl, substituted pyridinyl, substituted pyridinylalkyl, substituted pyridinylalkenyl, substituted pyridinylalkynyl, substituted thiophenyl, substituted thiophenylalkyl, substituted thiophenylalkenyl, substituted thiophenylalkynyl, substituted 2,3-dihydro-1H-isoindol-2-yl, substituted 1H-indol-2-yl and substituted benzofuran-2-yl are substituted with $R^8$, $R^9$ and $R^{10}$, wherein in case $R^1$ is alkyl and Y is —C(O)—, then $R^3$ is selected from the groups S, T, U, V, X, Z, AA, AB, AC, AD, AE, AF, AG, AH, AI, AJ, AK and AL;

$R^2$ is —$(CR^4R^5)_n$—$R^3$, —C(O)—$R^3$, —S(O)$_2$—$R^3$ or —C(O)—$NR^6R^3$;

Y is —OC(O)—, —$NR^{14}$C(O)—, —C(O)—, —S(O)$_2$—,

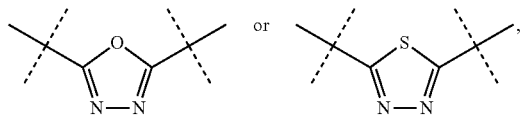

wherein in case $R^1$ is substituted phenylalkenyl, substituted pyridinylalkenyl or substituted thiophenylalkenyl, then Y is not —OC(O)—;

W is selected from one of the following ring systems:

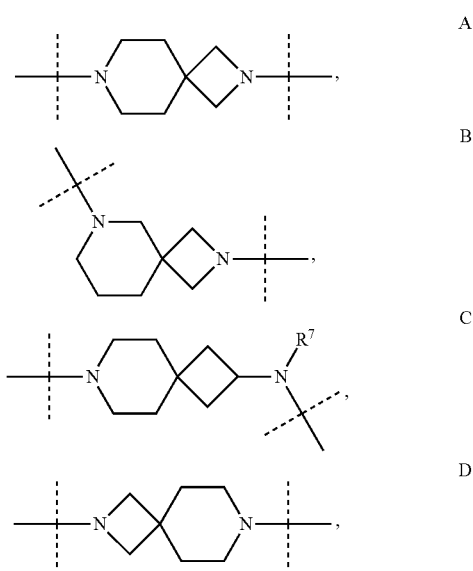

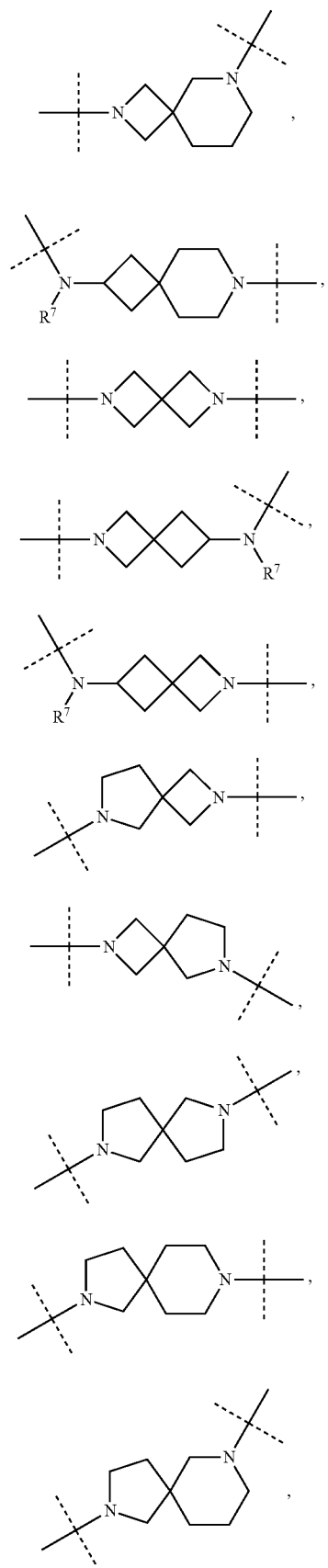
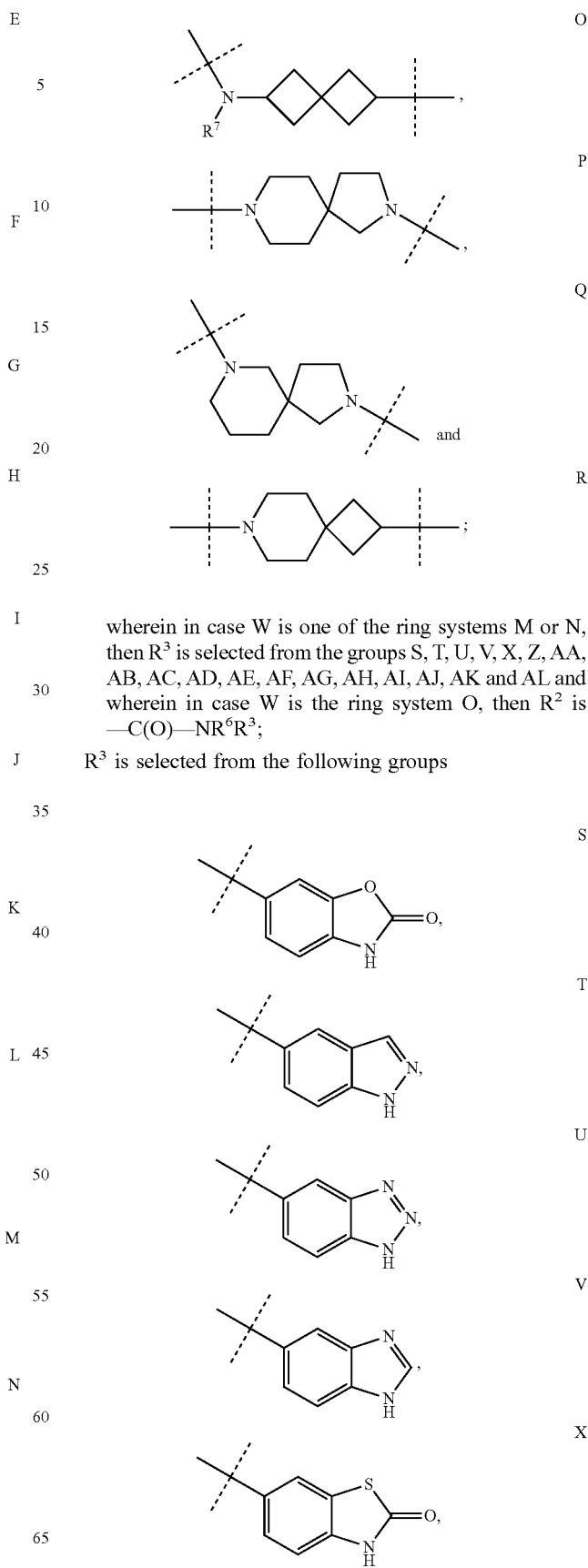
wherein in case W is one of the ring systems M or N, then R³ is selected from the groups S, T, U, V, X, Z, AA, AB, AC, AD, AE, AF, AG, AH, AI, AJ, AK and AL and wherein in case W is the ring system O, then R² is —C(O)—NR⁶R³;
R³ is selected from the following groups Z 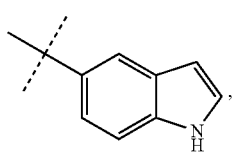

AA 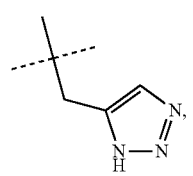

AB 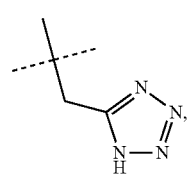

AC 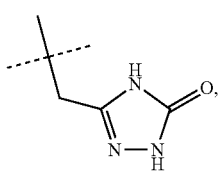

AD 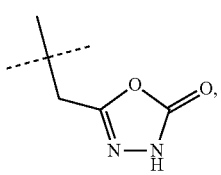

AE 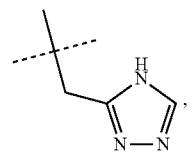

AF 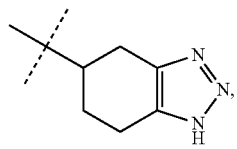

AG 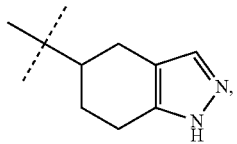

AH 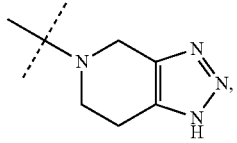

AI 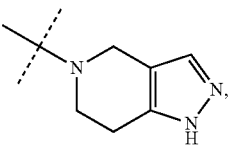

AJ 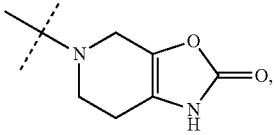

AK 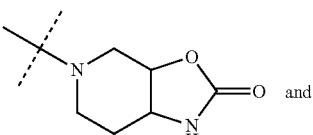

and

AL 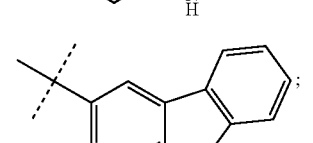

or $R^3$ is substituted phenyl, substituted pyridinyl or substituted thiophenyl, wherein substituted phenyl, substituted pyridinyl and substituted thiophenyl are substituted with $R^{11}$, $R^{12}$ and $R^{13}$;

$R^4$ and $R^5$ are independently selected from H, halogen, alkyl and cycloalkyl;

$R^6$, $R^7$ and $R^{14}$ are independently selected from H, alkyl and cycloalkyl;

$R^8$, $R^9$, $R^{10}$, $R^{11}$, $R^{12}$, and $R^{13}$ are independently selected from H, alkyl, hydroxyalkyl, haloalkyl, cycloalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, halogen, hydroxy, cyano, alkylsulfonyl, cycloalkylsulfonyl, substituted aminosulfonyl, substituted amino and substituted aminoalkyl, wherein substituted aminosulfonyl, substituted amino and substituted aminoalkyl are substituted on the nitrogen atom with one to two substituents independently selected from hydrogen, alkyl, cycloalkyl, cycloalkylalkyl, hydroxyalkyl, alkoxyalkyl, alkylcarbonyl and cycloalkylcarbonyl;

n is zero, 1, 2 or 3;

or pharmaceutically acceptable salts.

In another aspect of the invention, the compounds of formula (I) or their pharmaceutically acceptable salts and esters can be used for the treatment or prophylaxis of diseases, disorders or conditions that are associated with the activity of autotaxin and/or the biological activity of lysophosphatidic acid (LPA).

The compounds of formula (I) or their pharmaceutically acceptable salts and esters herein inhibit autotaxin activity and therefore inhibit LPA production and modulate LPA levels and associated signaling. Autotaxin inhibitors described herein are useful as agents for the treatment or prevention of diseases or conditions in which ATX activity and/or LPA signaling participates, is involved in the etiology or pathology of the disease, or is otherwise associated with at least one symptom of the disease. The ATX-LPA axis has been implicated for example in angiogenesis, chronic inflammation, autoimmune diseases, fibrotic diseases, cancer and tumor metastasis and progression, ocular conditions, metabolic conditions such as obesity and/or diabetes mellitus, conditions such as cholestatic or other forms of chronic pruritus as well as acute and chronic organ transplant rejection.

In another aspect, the present invention provides for compound of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of ATX and/or the biological activity of lysophosphatidic acid (LPA), particularly in the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and—chronic organ transplant rejection, and the use of the said compounds, salts or esters for the production of medicaments for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

DETAILED DESCRIPTION OF THE INVENTION

Definitions

The term "alkenyl" denotes a monovalent linear or branched hydrocarbon group of 2 to 7 carbon atoms with at least one double bond. In particular embodiments, alkenyl has 2 to 4 carbon atoms with at least one double bond. Examples of alkenyl include ethenyl, propenyl, prop-2-enyl, isopropenyl, n-butenyl and iso-butenyl. Particular alkenyl group is ethenyl.

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy.

The term "alkoxyalkoxy" denotes an alkoxy group wherein at least one of the hydrogen atoms of the alkoxy group has been replaced by another alkoxy group. Examples of alkoxyalkoxy group include methoxymethoxy, ethoxymethoxy, methoxyethoxy, ethoxyethoxy, methoxypropoxy and ethoxypropoxy. Particular alkoxyalkoxy groups include methoxymethoxy and methoxyethoxy.

The term "alkoxyalkoxyalkyl" denotes an alkyl group wherein at least one of the hydrogen atoms of the alkyl group has been replaced by an alkoxyalkoxy group. Examples of alkoxyalkoxyalkyl group include methoxymethoxymethyl, ethoxymethoxymethyl, methoxyethoxymethyl, ethoxyethoxymethyl, methoxypropoxymethyl, ethoxypropoxymethyl, methoxymethoxyethyl, ethoxymethoxyethyl, methoxyethoxyethyl, ethoxyethoxyethyl, methoxypropoxyethyl and ethoxypropoxyethyl.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxyethyl, ethoxyethyl, methoxypropyl, ethoxypropyl and isopropoxymethyl. Particular alkoxyalkyl group include include methoxymethyl, methoxyethyl and isopropoxymethyl.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl and sec-butyl, pentyl. Particular alkyl groups include methyl, ethyl, propyl and isopropyl. More particular alkyl group is methyl.

The term "alkylcarbonyl" denotes a group of the formula —C(O)—R', wherein R' is an alkyl group. Examples of alkylcarbonyl groups include groups of the formula —C(O)—R', wherein R' is methyl or ethyl. Particular alkylcarbonyl groups include groups of the formula —C(O)—R', wherein R' is methyl.

The term "alkylsulfonyl" denotes a group of the formula —S(O)$_2$—R', wherein R' is an alkyl group. Examples of alkylsulfonyl groups include groups of the formula —S(O)$_2$—R', wherein R' is methyl, ethyl, n-propyl, isopropyl, n-butyl, isobutyl or tert-butyl. Particulars alkylsulfonyl group include group of the formula —S(O)$_2$—R', wherein R' is methyl.

The term "alkynyl" denotes a monovalent linear or branched saturated hydrocarbon group of 2 to 7 carbon atoms comprising one, two or three triple bonds. In particular embodiments alkynyl has from 2 to 4 carbon atoms comprising one or two triple bonds. Examples of alkynyl include ethynyl, propynyl, prop-2-ynyl, isopropynyl and n-butynyl.

The term "amino" denotes a —NH$_2$ group.

The term "aminosulfonyl" denotes a —S(O)$_2$—NH$_2$ group.

The term "carbonyl" denotes a —C(O)— group.

The term "cyano" denotes a —C≡N group.

The term "cycloalkoxy" denotes a group of the formula —O—R', wherein R' is a cycloalkyl group. Examples of cycloalkoxy group include cyclopropoxy, cyclobutoxy, cyclopentyloxy, cyclohexyloxy, cycloheptyloxy and cyclooctyloxy. Particular cycloalkoxy group is cyclopropoxy.

The term "cycloalkoxyalkyl" denotes an alkyl group wherein at least one of the hydrogen atoms of the alkyl group has been replaced by a cycloalkoxy group. Examples of cycloalkoxyalkyl group include cyclopropoxymethyl, cyclopropoxyethyl, cyclobutoxymethyl, cyclobutoxyethyl, cyclopentyloxymethyl, cyclopentyloxyethyl, cyclohexyloxymethyl, cyclohexyloxyethyl, cycloheptyloxymethyl, cycloheptyloxyethyl, cyclooctyloxymethyl and cyclooctyloxyethyl.

The term "cycloalkyl" denotes a monovalent saturated monocyclic or bicyclic hydrocarbon group of 3 to 10 ring carbon atoms. In particular embodiments, cycloalkyl denotes a monovalent saturated monocyclic hydrocarbon group of 3 to 8 ring carbon atoms. Bicyclic means consisting of two saturated carbocycles having two carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl groups are cyclopropyl, cyclobutanyl, cyclopentyl and cyclohexyl. More particular monocyclic cycloalkyl group is cyclopropyl.

The term "cycloalkylalkoxy" denotes an alkoxy group wherein at least one of the hydrogen atoms of the alkoxy group is replaced by a cycloalkyl group. Examples of cycloalkylalkoxy include cyclopropylmethoxy, cyclobutylmethoxy, cyclopentylmethoxy, cyclohexylmethoxy, cycloheptylmethoxy and cyclooctylmethoxy.

The term "cycloalkylalkoxyalkyl" denotes an alkyl group wherein at least one of the hydrogen atoms of the alkyl group is replaced by a cycloalkylalkoxy group. Examples of cycloalkylalkoxyalkyl include cyclopropylmethoxymethyl, cyclopropylmethoxyethyl, cyclobutylmethoxymethyl, cyclobutylmethoxyethyl, cyclopentylmethoxyethyl, cyclopentylmethoxyethyl, cyclohexylmethoxymethyl, cyclohexylmethoxyethyl, cycloheptylmethoxymethyl, cycloheptylmethoxyethyl, cyclooctylmethoxymethyl and cyclooctylmethoxyethyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclopropylbutyl, cyclobutylpropyl, 2-cyclopropylbutyl and cyclopentylbutyl. Particular examples of cycloalkylalkyl groups are cyclopropylmethyl, cyclopropylbutyl and 2-cyclopropylbutyl.

The term "cycloalkylcarbonyl" of the formula —C(O)—R', wherein R' is a cycloalkyl group. Examples of cycloalkylcarbonyl groups include groups of the formula —C(O)—R', wherein R' is cyclopropyl.

The term "cycloalkylsulfonyl" denotes a group of the formula —S(O)$_2$—R', wherein R' is a cycloalkyl group. Examples of cycloalkylsulfonyl groups include groups of the formula —S(O)$_2$—R', wherein R' is cyclopropyl.

The term "haloalkoxy" denotes an alkoxy group wherein at least one of the hydrogen atoms of the alkoxy group has been replaced by the same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy group is trifluoromethoxy.

The term "haloalkoxyalkyl" denotes an alkyl group wherein at least one of the hydrogen atoms of the alkyl group has been replaced by a haloalkoxy group. Examples of haloalkoxyalkyl include fluoromethoxymethyl, difluoromethoxymethyl, trifluoromethoxymethyl, fluoroethoxymethyl, difluoroethoxymethyl, trifluoroethoxymethyl, fluoromethoxyethyl, difluoromethoxyethyl, trifluoromethoxyethyl, fluoroethoxyethyl, difluoroethoxyethyl, trifluoroethoxyethyl, fluoromethoxypropyl, difluoromethoxypropyl, trifluoromethoxypropyl, fluoroethoxypropyl, difluoroethoxypropyl and trifluoroethoxypropyl. Particular haloalkoxyalkyl is 2,2,2-trifluoroethoxyethyl.

The term "haloalkyl" denotes an alkyl group wherein at least one of the hydrogen atoms of the alkyl group has been replaced by the same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl group is trifluoromethyl.

The term "halogen" and "halo" are used interchangeably herein and denote fluoro, chloro, bromo, or iodo. Particular halogens are chloro, fluoro and bromo.

In the case of $R^8$, $R^9$ and $R^{10}$ further particular halogen is chloro.

In the case of $R'^2$, further particular halogen is fluoro.

The term "hydroxy" denotes a —OH group.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxy-1-methyl-ethyl, hydroxypropyl, hydroxymethylpropyl and dihydroxypropyl. Particular examples are hydroxymethyl and hydroxyethyl.

The term "phenoxy" denotes a group of the formula —O—R', wherein R' is a phenyl.

The term "phenoxyalkyl" denotes an alkyl group wherein at least one of the hydrogen atoms of the alkyl group has been replaced by a phenoxy group. Exemplary phenoxyalkyl groups include phenoxymethyl, phenoxyethyl and phenoxypropyl. Particular alkoxyalkyl group is phenoxymethyl.

The term "phenylalkenyl" denotes an alkenyl group wherein at least one of the hydrogen atoms of the alkenyl group has been replaced a phenyl. Particular phenylalkenyl group is phenylethenyl.

The term "phenylalkyl" denotes an alkyl group wherein at least one of the hydrogen atoms of the alkyl group has been replaced a phenyl. Particular phenylalkyl groups are benzyl, phenethyl and phenylpropyl. More particular phenylalkyl groups are benzyl, pheneth-1-yl, pheneth-2-yl and phenylpropyl. Further particular phenylalkyl group is benzyl.

The term "phenylalkynyl" denotes an alkynyl group wherein at least one of the hydrogen atoms of the alkynyl group has been replaced a phenyl. Particular phenylalkynyl group is phenylethynyl.

The term "phenylcyloalkyl" denotes a cycloalkyl group wherein at least one of the hydrogen atoms of the cycloalkyl group has been replaced a phenyl. Particular phenylcycloalkyl group is phenylcyclopropyl.

The term "pyridinylalkenyl" denotes an alkenyl group wherein at least one of the hydrogen atoms of the alkenyl group has been replaced a pyridinyl. Particular pyridinylalkenyl group is pyridinylethenyl.

The term "pyridinylalkyl" denotes an alkyl group wherein at least one of the hydrogen atoms of the alkyl group has been replaced a pyridinyl. Particular pyridinylalkyl groups are pyridinylmethyl, pyridinylethyl and pyridinylpropyl. More particular pyridinylalkyl group is pyridinylmethyl.

The term "pyridinylalkynyl" denotes an alkynyl group wherein at least one of the hydrogen atoms of the alkynyl group has been replaced a pyridinyl. Particular pyridinylalkynyl group is pyridinylethynyl.

The term "thiophenylalkenyl" denotes an alkenyl group wherein at least one of the hydrogen atoms of the alkenyl group has been replaced a thiophenyl. Particular thiophenylalkenyl group is thiophenylethenyl.

The term "thiophenylalkyl" denotes an alkyl group wherein at least one of the hydrogen atoms of the alkyl group has been replaced a thiophenyl. Particular thiophenylalkyl groups are thiophenylmethyl, thiophenylethyl and thiophenylpropyl. More particular thiophenylalkyl group is thiophenylmethyl.

The term "thiophenylalkynyl" denotes an alkynyl group wherein at least one of the hydrogen atoms of the alkynyl group has been replaced a thiophenyl. Particular thiophenylalkynyl group is thiophenylethynyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc).

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Compounds

The present invention provides novel compounds of formula (I)

wherein

R$^1$ is alkyl, haloalkyl, cycloalkyl, substituted phenyl, substituted phenylalkyl, substituted phenoxyalkyl, substituted phenylcycloalkyl, substituted phenylalkenyl, substituted phenylalkynyl, substituted pyridinyl, substituted pyridinylalkyl, substituted pyridinylalkenyl, substituted pyridinylalkynyl, substituted thiophenyl, substituted thiophenylalkyl, substituted thiophenylalkenyl, substituted thiophenylalkynyl, substituted 2,3-dihydro-1H-isoindol-2-yl, substituted 1H-indol-2-yl or substituted benzofuran-2-yl, wherein substituted phenyl, substituted phenylalkyl, substituted phenoxyalkyl, substituted phenylcycloalkyl, substituted phenylalkenyl, substituted phenylalkynyl, substituted pyridinyl, substituted pyridinylalkyl, substituted pyridinylalkenyl, substituted pyridinylalkynyl, substituted thiophenyl, substituted thiophenylalkyl, substituted thiophenylalkenyl, substituted thiophenylalkynyl, substituted 2,3-dihydro-1H-isoindol-2-yl, substituted 1H-indol-2-yl and substituted benzofuran-2-yl are substituted with R$^8$, R$^9$ and R$^{10}$, wherein in case R$^1$ is alkyl and Y is —C(O)—, then R$^3$ is selected from the groups S, T, U, V, X, Z, AA, AB, AC, AD, AE, AF, AG, AH, AI, AJ, AK and AL;

R$^2$ is —(CR$^4$R$^5$)$_n$—R$^3$, —C(O)—R$^3$, —S(O)$_2$—R$^3$ or —C(O)—NR$^6$R$^3$;

Y is —OC(O)—, —NR$^{14}$C(O)—, —C(O)—, —S(O)$_2$—,

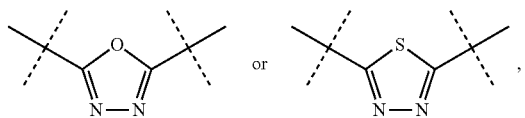

wherein in case R$^1$ is substituted phenylalkenyl, substituted pyridinylalkenyl or substituted thiophenylalkenyl, then Y is not —OC(O)—;

W is selected from one of the following ring systems:

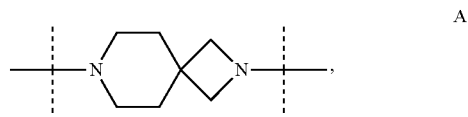

A

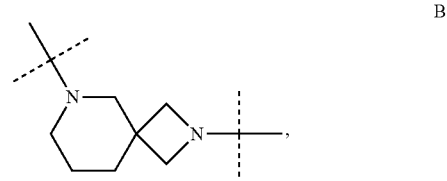

B

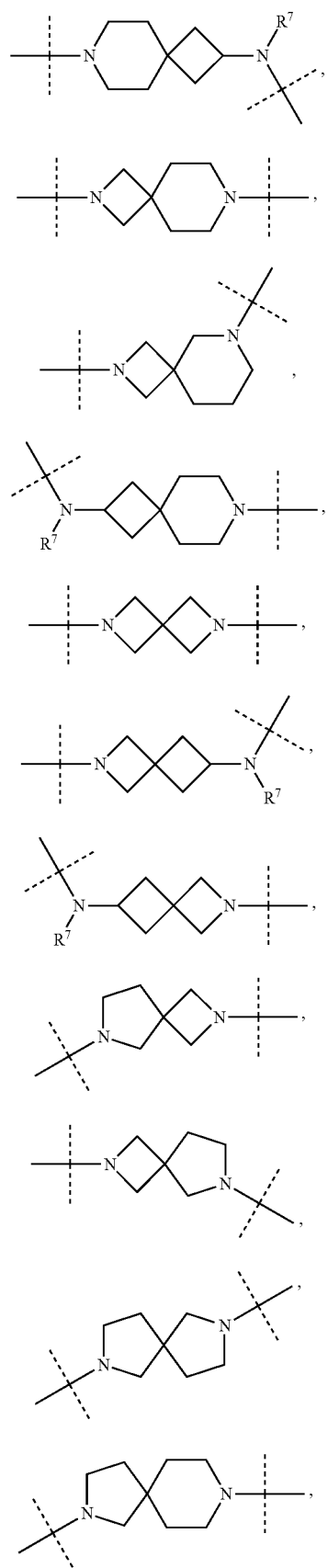
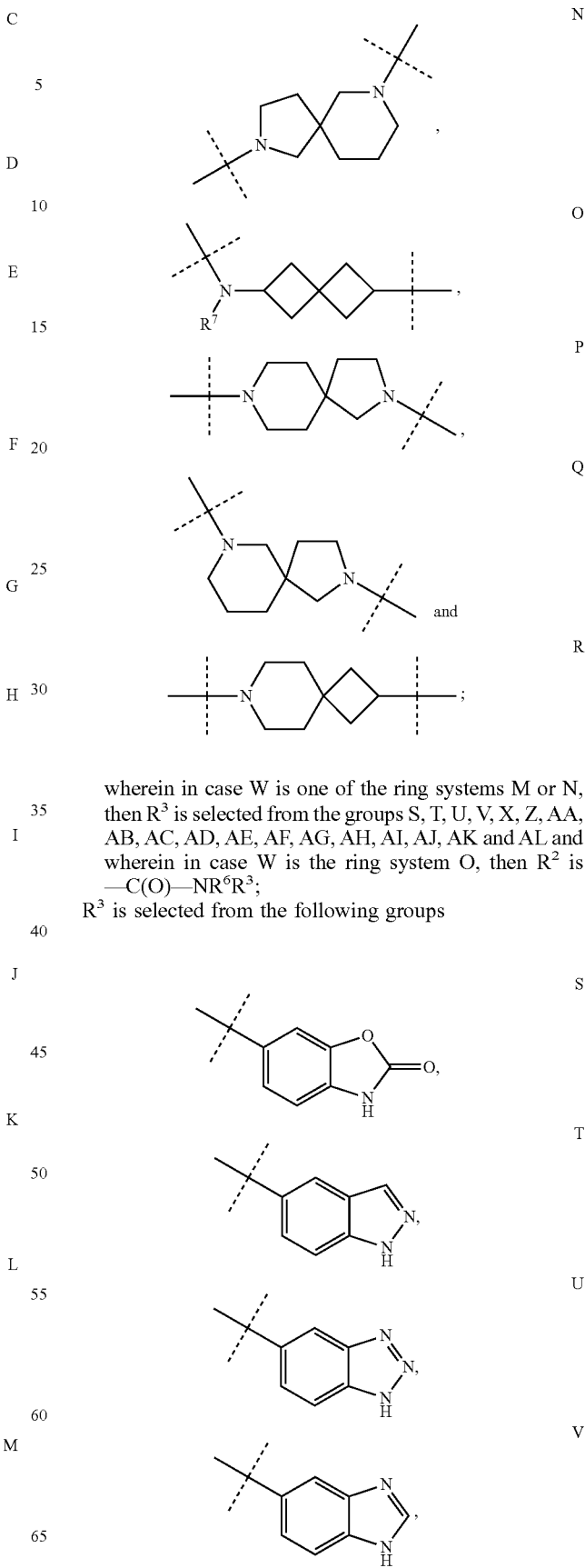
wherein in case W is one of the ring systems M or N, then R³ is selected from the groups S, T, U, V, X, Z, AA, AB, AC, AD, AE, AF, AG, AH, AI, AJ, AK and AL and wherein in case W is the ring system O, then R² is —C(O)—NR⁶R³;
R³ is selected from the following groups -continued X
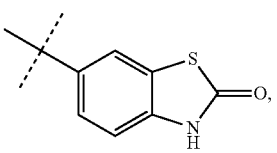

Z
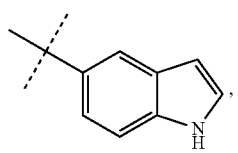

AA
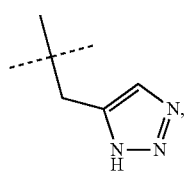

AB
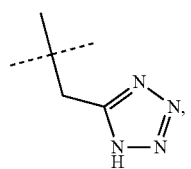

AC
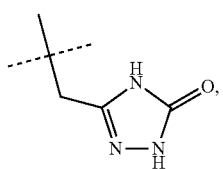

AD
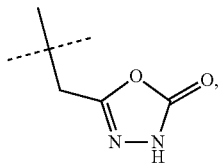

AE
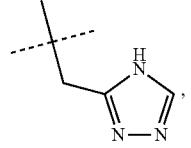

AF
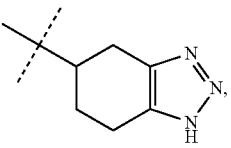

AG
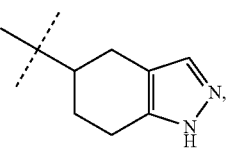

-continued

AH
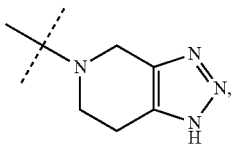

AI
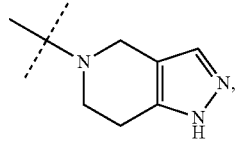

AJ
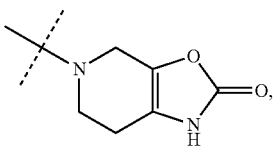

AK
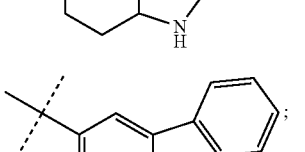 and

AL
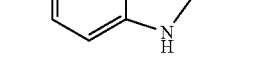;

or $R^3$ is substituted phenyl, substituted pyridinyl or substituted thiophenyl, wherein substituted phenyl, substituted pyridinyl and substituted thiophenyl are substituted with $R^{11}$, $R^{12}$ and $R^{13}$;

$R^4$ and $R^5$ are independently selected from H, halogen, alkyl and cycloalkyl;

$R^6$, $R^7$ and $R^{14}$ are independently selected from H, alkyl and cycloalkyl;

$R^8$, $R^9$, $R^{10}$, $R^{11}$, $R^{12}$, and $R^{13}$ are independently selected from H, alkyl, hydroxyalkyl, haloalkyl, cycloalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, halogen, hydroxy, cyano, alkylsulfonyl, cycloalkylsulfonyl, substituted aminosulfonyl, substituted amino and substituted aminoalkyl, wherein substituted aminosulfonyl, substituted amino and substituted aminoalkyl are substituted on the nitrogen atom with one to two substituents independently selected from hydrogen, alkyl, cycloalkyl, cycloalkylalkyl, hydroxyalkyl, alkoxyalkyl, alkylcarbonyl and cycloalkylcarbonyl;

n is zero, 1, 2 or 3;

or pharmaceutically acceptable salts.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

The substituents Y and $R^2$ are respectively connected to the left hand-side and right hand-side of the ring system W as described herein. For example, in case W is A, then the compounds of formula (I) as described herein are of formula (Ia).

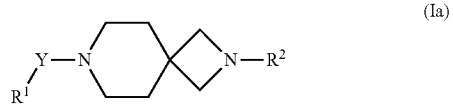

Another embodiment of the present invention are compounds according to formula (I) as described herein, wherein $R^1$ is substituted phenyl, substituted phenylalkyl, substituted phenoxyalkyl, substituted phenylcycloalkyl, substituted phenylalkenyl, substituted phenylalkynyl, substituted pyridinylalkyl, substituted thiophenylalkyl, substituted 2,3-dihydro-1H-isoindol-2-yl, substituted 1H-indol-2-yl or substituted benzofuran-2-yl, wherein substituted phenyl, substituted phenylalkyl, substituted phenoxyalkyl, substituted phenylcycloalkyl, substituted phenylalkenyl, substituted pyridinylalkyl, substituted thiophenylalkyl, substituted 2,3-dihydro-1H-isoindol-2-yl, substituted 1H-indol-2-yl and substituted benzofuran-2-yl are substituted with $R^8$, $R^9$ and $R^{10}$.

A further embodiment of the present invention are compounds according to formula (I) as described herein, wherein $R^1$ is substituted phenyl, substituted phenylalkyl, substituted phenoxyalkyl, substituted phenylcycloalkyl, substituted phenylalkenyl, substituted pyridinylalkyl, substituted thiophenylalkyl, substituted 2,3-dihydro-1H-isoindol-2-yl, substituted 1H-indol-2-yl or substituted benzofuran-2-yl, wherein substituted phenyl, substituted phenylalkyl, substituted phenoxyalkyl, substituted phenylcycloalkyl, substituted phenylalkenyl, substituted pyridinylalkyl, substituted thiophenylalkyl, substituted 2,3-dihydro-1H-isoindol-2-yl, substituted 1H-indol-2-yl and substituted benzofuran-2-yl are substituted with $R^8$, $R^9$ and $R^{10}$.

A particular embodiment of the present invention are compounds according to formula (I) as described herein, wherein $R^1$ is substituted phenyl, substituted phenylalkyl, substituted phenoxyalkyl, substituted phenylcycloalkyl or substituted phenylalkenyl, wherein substituted phenyl, substituted phenylalkyl, substituted phenoxyalkyl, substituted phenylcycloalkyl and substituted phenylalkenyl are substituted with $R^8$, $R^9$ and $R^{10}$.

In a further embodiment of the present invention are compounds according to formula (I) as described herein, wherein $R^1$ is substituted phenylalkyl or substituted phenylalkenyl, wherein substituted phenylalkyl and substituted phenylalkenyl are substituted with $R^8$, $R^9$ and $R^{10}$.

Another embodiment of the present invention are compounds according to formula (I) as described herein, wherein $R^1$ is 3,5-dichlorobenzyl, 3-chloro-5-(methylsulfonyl)benzyl, 3-(methylsulfonyl)-5-(trifluoromethyl)benzyl or 3,5-dichlorophenylethenyl.

The present invention also relates to compounds according to formula (I) as described herein, wherein $R^1$ is phenylalkyl substituted with $R^8$, $R^9$ and $R^{10}$.

A further particular embodiment of the present invention are compounds according to formula (I) as described herein, wherein $R^1$ is 3,5-dichlorobenzyl, 3-chloro-5-(methylsulfonyl)benzyl or 3-(methylsulfonyl)-5-(trifluoromethyl)benzyl.

Another further embodiment of the present invention are compounds according to formula (I) as described herein, wherein $R^1$ is phenylalkenyl substituted with $R^8$, $R^9$ and $R^{10}$.

Another embodiment of the present invention are compounds according to formula (I) as described herein, wherein $R^1$ is 3,5-dichlorophenylethenyl.

A more particular embodiment of the present invention are compounds according to formula (I) as described herein, wherein $R^2$ is —C(O)—$R^3$.

Also an embodiment of the present invention are compounds according to formula (I) as described herein, wherein Y is —OC(O)— or —C(O)—, wherein in case $R^1$ is substituted phenylalkenyl, substituted pyridinylalkenyl or substituted thiophenylalkenyl, then Y is not —OC(O)—.

The present invention also relates to compounds according to formula (I) as described herein, wherein Y is —OC(O)— and $R^1$ is not substituted phenylalkenyl, substituted pyridinylalkenyl or substituted thiophenylalkenyl.

Another embodiment of the present invention are compounds according to formula (I) as described herein, wherein Y is —C(O)—.

Another embodiment of the present invention are compounds according to formula (I) as described herein, wherein Y is —C(O)— and of formula (In).

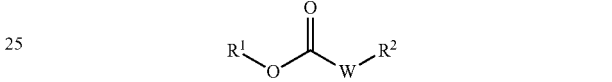

A further particular embodiment of the present invention are compounds according to formula (I) as described herein, wherein is W is selected from one of the ring systems A, C, D, H, I, J, L, M, N, O, Q and R, wherein in case W is one of the ring systems M or N, then $R^3$ is selected from the groups S, T, U, V, X, Z, AA, AB, AC, AD, AE, AF, AG, AH, AI, AJ, AK and AL, and wherein in case W is the ring system O, then $R^2$ is —C(O)—$NR^6R^3$.

A further particular embodiment of the present invention are compounds according to formula (I) as described herein, wherein is W is A and of formula (Ia).

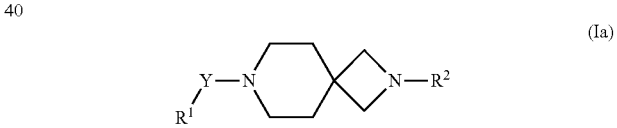

A further particular embodiment of the present invention are compounds according to formula (I) as described herein, wherein is W is C and of formula (Ib).

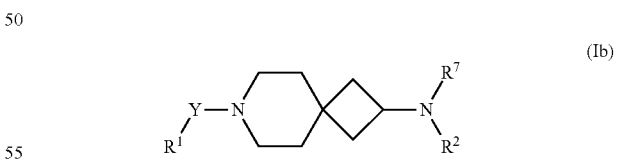

A further particular embodiment of the present invention are compounds according to formula (I) as described herein, wherein is W is D and of formula (Ic).

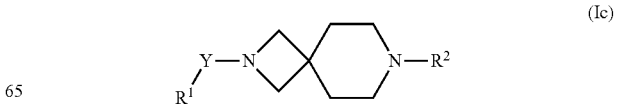

A further particular embodiment of the present invention are compounds according to formula (I) as described herein, wherein is W is H and of formula (Id).

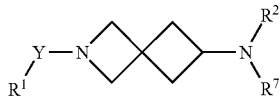

(Id)

A further particular embodiment of the present invention are compounds according to formula (I) as described herein, wherein is W is I and of formula (Ie).

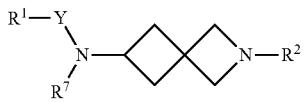

(Ie)

A further particular embodiment of the present invention are compounds according to formula (I) as described herein, wherein is W is J and of formula (If).

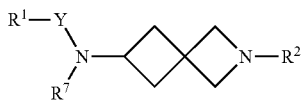

(If)

A further particular embodiment of the present invention are compounds according to formula (I) as described herein, wherein is W is L and of formula (Ig).

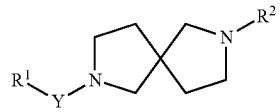

(Ig)

A further particular embodiment of the present invention are compounds according to formula (I) as described herein, wherein is W is M, $R^3$ is selected from the groups S, T, U, V, X, Z, AA, AB, AC, AD, AE, AF, AG, AH, AI, AJ, AK and AL and of formula (Ih).

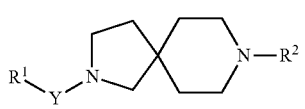

(Ih)

A further particular embodiment of the present invention are compounds according to formula (I) as described herein, wherein is W is $NR^3$ is selected from the groups S, T, U, V, X, Z, AA, AB, AC, AD, AE, AF, AG, AH, AI, AJ, AK and AL and of formula (Ii).

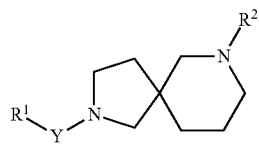

(Ii)

A further particular embodiment of the present invention are compounds according to formula (I) as described herein, wherein is W is $OR^2$ is —C(O)—$NR^6R^3$ and of formula (Ij).

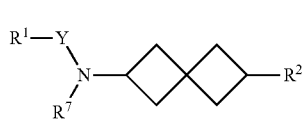

(Ij)

A further particular embodiment of the present invention are compounds according to formula (I) as described herein, wherein is W is Q and of formula (Ik).

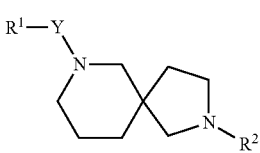

(Ik)

A further particular embodiment of the present invention are compounds according to formula (I) as described herein, wherein is W is R and of formula (Im).

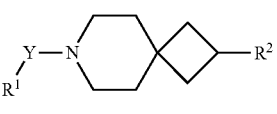

(Im)

A particular embodiment of the present invention are compounds according to formula (I) as described herein, wherein W is selected from one of the ring systems A and H.

Also an embodiment of the present invention are compounds according to formula (I) as described herein, wherein W is the ring system A.

The present invention also relates to compounds according to formula (I) as described herein, wherein $R^3$ is substituted phenyl, substituted pyridinyl or substituted thiophenyl, wherein substituted phenyl, substituted pyridinyl and substituted thiophenyl are substituted with $R^{11}$, $R^{12}$ and $R^{13}$.

Another embodiment of the present invention are compounds according to formula (I) as described herein, wherein $R^3$ is selected from the groups S, T, U, V, X, Z, AA, AB, AC and AD.

The present invention also relates to compounds according to formula (I) as described herein, wherein $R^3$ is phenyl substituted with $R^{11}$, $R^{12}$ and $R^{13}$.

Also an embodiment of the present invention are compounds according to formula (I) as described herein, wherein $R^3$ is selected from the groups S, U, X, AA and AF.

Also an embodiment of the present invention are compounds according to formula (I) as described herein, wherein $R^3$ is selected from the groups S, U, X and AA.

Another embodiment of the present invention are compounds according to formula (I) as described herein, wherein $R^3$ is selected from the groups S, U and AF.

Another embodiment of the present invention are compounds according to formula (I) as described herein, wherein $R^3$ is selected from the groups S and U.

Also an embodiment of the present invention are compounds according to formula (I) as described herein, wherein $R^4$ and $R^5$ are H.

A particular embodiment of the present invention are compounds according to formula (I) as described herein, wherein $R^6$, $R^7$ and $R^{14}$ are H.

A further particular embodiment of the present invention are compounds according to formula (I) as described herein, wherein $R^8$, $R^9$ and $R^{10}$ are independently selected from H, alkyl, haloalkyl, haloalkoxy, halogen, cyano and alkylsulfonyl.

A more particular embodiment of the present invention are compounds according to formula (I) as described herein, wherein $R^8$ is H, alkyl, haloalkyl, haloalkoxy, halogen, cyano or alkylsulfonyl.

Also a particular embodiment of the present invention are compounds according to formula (I) as described herein, wherein $R^8$ is haloalkoxy, halogen or alkylsulfonyl.

Also a particular embodiment of the present invention are compounds according to formula (I) as described herein, wherein $R^8$ is halogen or alkylsulfonyl.

The present invention also relates to compounds according to formula (I) as described herein, wherein $R^9$ is H, alkyl, haloalkyl or halogen.

A further particular embodiment of the present invention are compounds according to formula (I) as described herein, wherein $R^9$ is alkyl, haloalkyl or halogen.

A more particular embodiment of the present invention are compounds according to formula (I) as described herein, wherein $R^9$ is haloalkyl or halogen.

Also an embodiment of the present invention are compounds according to formula (I) as described herein, wherein $R^{10}$ is H or halogen.

The present invention also relates to compounds according to formula (I) as described herein, wherein $R^{10}$ is H.

Another embodiment of the present invention are compounds according to formula (I) as described herein, wherein $R^{11}$, $R^{12}$ and $R^{13}$ are independently selected from H, haloalkoxy, halogen, hydroxy, substituted aminosulfonyl and substituted amino, wherein substituted aminosulfonyl and substituted amino are substituted on the nitrogen atom with two hydrogens.

A further particular embodiment of the present invention are compounds according to formula (I) as described herein, wherein is $R^{11}$ is haloalkoxy, halogen, substituted aminosulfonyl or substituted amino, wherein substituted aminosulfonyl and substituted amino are substituted on the nitrogen atom with two hydrogens.

A particular embodiment of the present invention are compounds according to formula (I) as described herein, wherein $R^{12}$ is H or hydroxy.

Also an embodiment of the present invention are compounds according to formula (I) as described herein, wherein $R^{13}$ is H.

The present invention also relates to compounds according to formula (I) as described herein, wherein n is zero or 1.

Particular examples of compounds of formula (I) as described herein are selected from 3,5-dichlorobenzyl 2-(1H-benzo[d][1,2,3]triazole-5-carbonyl)-2,7-diazaspiro[3.5]nonane-7-carboxylate;

benzyl 2-(1H-benzo[d][1,2,3]triazole-5-carbonyl)-2,7-diazaspiro[3.5]nonane-7-carboxylate;

4-chlorobenzyl 2-(1H-benzo[d][1,2,3]triazole-5-carbonyl)-2,7-diazaspiro[3.5]nonane-7-carboxylate;

3-chlorobenzyl 2-(1H-benzo[d][1,2,3]triazole-5-carbonyl)-2,7-diazaspiro[3.5]nonane-7-carboxylate;

1-(2-(1H-benzo[d][1,2,3]triazole-5-carbonyl)-2,7-diazaspiro[3.5]nonan-7-yl)-3-(3,5-dichlorophenyl)propan-1-one;

1-(2-(4-amino-3-hydroxybenzoyl)-2,7-diazaspiro[3.5]nonan-7-yl)-3-(3,5-dichlorophenyl)propan-1-one;

3,5-dichlorobenzyl 2-(4-amino-3-hydroxybenzoyl)-2,7-diazaspiro[3.5]nonane-7-carboxylate;

6-[(1H-benzotriazole-5-carbonyl)-amino]-2-aza-spiro[3.3]heptane-2-carboxylic acid benzyl ester;

N-(2-(4-phenylbutanoyl)-2-azaspiro[3.3]heptan-6-yl)-1H-benzo[d][1,2,3]triazole-5-carboxamide;

3-chloro-5-(methylsulfonyl)benzyl 2-(1H-benzo[d][1,2,3]triazole-5-carbonyl)-2,7-diazaspiro[3.5]nonane-7-carboxylate;

[2-(1H-benzotriazole-5-carbonyl)-2-aza-spiro[3.3]hept-6-yl]-carbamic acid benzyl ester;

N-(2-(3-(3,5-dichlorophenyl)propanoyl)-2-azaspiro[3.3]heptan-6-yl)-1H-benzo[d][1,2,3]triazole-5-carboxamide;

[2-(1H-benzotriazole-5-carbonyl)-2-aza-spiro[3.3]hept-6-yl]-carbamic acid 3,5-dichloro-benzyl ester;

6-[(1H-benzotriazole-5-carbonyl)-amino]-2-aza-spiro[3.3]heptane-2-carboxylic acid 3,5-dichloro-benzyl ester;

3,5-dichlorobenzyl 2-(1H-benzo[d][1,2,3]triazole-5-carbonyl)-2,6-diazaspiro[3.4]octane-6-carboxylate;

3,5-dichlorobenzyl 7-(1H-benzo[d][1,2,3]triazole-5-carbonyl)-2,7-diazaspiro[3.5]nonane-2-carboxylate;

3,5-dichlorobenzyl 6-(4-amino-3-hydroxybenzamido)-2-azaspiro[3.3]heptane-2-carboxylate;

3-chloro-5-(methylsulfonyl)benzyl 2-(4-sulfamoylbenzoyl)-2,7-diazaspiro[3.5]nonane-7-carboxylate;

3-chloro-5-(methylsulfonyl)benzyl 2-(3-sulfamoylbenzoyl)-2,7-diazaspiro[3.5]nonane-7-carboxylate;

3,5-dichlorobenzyl 8-(1H-benzo[d][1,2,3]triazole-5-carbonyl)-2,8-diazaspiro[4.5]decane-2-carboxylate;

3-fluoro-5-(trifluoromethoxy)benzyl 7-(1H-benzo[d][1,2,3]triazole-5-carbonyl)-2,7-diazaspiro[4.5]decane-2-carboxylate;

(1H-benzotriazol-5-yl)-{7-[2-(3-chloro-phenyl)-ethanesulfonyl]-2,7-diaza-spiro[3.5]non-2-yl}-methanone;

3,5-dichlorobenzyl 2-(2-oxo-2,3-dihydrobenzo[d]oxazole-6-carbonyl)-2,6-diazaspiro[3.4]octane-6-carboxylate;

3-chloro-5-(methylsulfonyl)benzyl 2-(2-oxo-2,3-dihydrobenzo[d]oxazole-6-carbonyl)-2,7-diazaspiro[3.5]nonane-7-carboxylate;

7-(2-oxo-2,3-dihydro-benzooxazole-6-carbonyl)-2,7-diazaspiro[3.5]nonane-2-carboxylic acid 3,5-dichloro-benzyl ester;

3,5-dichlorobenzyl 2-(2-oxo-2,3-dihydrobenzo[d]oxazol-6-ylsulfonyl)-2,7-diazaspiro[3.5]nonane-7-carboxylate;

2-oxo-2,3-dihydro-benzooxazole-6-sulfonic acid [2-(4-phenyl-butyryl)-2-aza-spiro[3.3]hept-6-yl]-amide;

benzyl 6-(2-oxo-2,3-dihydrobenzo[d]oxazole-6-sulfonamido)-2-azaspiro[3.3]heptane-2-carboxylate;

2-oxo-2,3-dihydro-benzooxazole-6-sulfonic acid {2-[3-(3,5-dichloro-phenyl)-propionyl]-2-aza-spiro[3.3]hept-6-yl}-amide;

3,5-dichlorobenzyl 6-(2-oxo-2,3-dihydrobenzo[d]oxazole-6-sulfonamido)-2-azaspiro[3.3]heptane-2-carboxylate;

[2-(2-oxo-2,3-dihydro-benzooxazole-6-sulfonyl)-2-aza-spiro[3.3]hept-6-yl]-carbamic acid 3,5-dichloro-benzyl ester;

3-chloro-5-(methylsulfonyl)benzyl 2-(2-oxo-2,3-dihydrobenzo[d]thiazol-6-ylsulfonyl)-2,7-diazaspiro[3.5]nonane-7-carboxylate;
3,5-dichlorobenzyl 2-((2-oxo-2,3-dihydrobenzo[d]oxazol-6-yl)methyl)-2,7-diazaspiro[3.5]nonane-7-carboxylate;
3,5-dichlorobenzyl 2-(2-oxo-2,3-dihydrobenzo[d]oxazole-6-carbonyl)-2,7-diazaspiro[3.5]nonane-7-carboxylate;
6-(7-(3-(3,5-dichlorophenyepropanoyl)-2,7-diazaspiro[3.5]nonane-2-carbonyl)benzo[d]oxazol-2(3H)-one;
6-[2-oxo-2,3-dihydro-benzooxazole-6-carbonyl)-amino]-2-aza-spiro[3.3]heptane-2-carboxylic acid 3,5-dichloro-benzyl ester;
(E)-1-(2-(1H-benzo[d][1,2,3]triazole-5-carbonyl)-2,7-diazaspiro[3.5]nonan-7-yl)-3-(3,5-dichlorophenyl)prop-2-en-1-one;
6-(7-(3-(3,5-dichlorophenyepropanoyl)-7-azaspiro[3.5]nonan-2-ylamino)benzo[d]oxazol-2(3H)-one;
1-(2-(1H-benzo[d][1,2,3]triazole-5-carbonyl)-2,7-diazaspiro[3.5]nonan-7-yl)-2-(3,5-dichlorophenoxy)ethanone;
(2-(1H-benzo[d][1,2,3]triazole-5-carbonyl)-2,7-diazaspiro[3.5]nonan-7-yl)(3,5-dichlorophenyemethanone;
6-{7-[(E)-3-(3,5-dichloro-phenyl)-acryloyl]-2,7-diaza-spiro[3.5]nonane-2-carbonyl}-3H-benzooxazol-2-one;
(2-(1H-benzo[d][1,2,3]triazole-5-carbonyl)-2,7-diazaspiro[3.5]nonan-7-yl)(trans-2-(3,5-difluorophenyl)cyclopropyl)methanone;
(7-(1H-benzo[d][1,2,3]triazole-5-carbonyl)-2,7-diazaspiro[4.4]nonan-2-yl)(5-chloro-1H-indol-2-yl)methanone;
(7-(1H-benzo[d][1,2,3]triazole-5-carbonyl)-2,7-diazaspiro[4.4]nonan-2-yl)(5-chlorobenzofuran-2-yl)methanone;
(E)-N-((1H-1,2,3-triazol-5-yl)methyl)-7-(3-(4-(trifluoromethoxy)phenyl)acryloyl)-7-azaspiro[3.5]nonane-2-carboxamide;
(1H-benzo[d][1,2,3]triazol-5-yl)(7-(5-(3,5-dichlorophenyl)-1,3,4-oxadiazol-2-yl)-2,7-diazaspiro[3.5]nonan-2-yl)methanone;
(1H-benzo[d][1,2,3]triazol-5-yl)(7-(5-(4-chlorophenyl)-1,3,4-oxadiazol-2-yl)-2,7-diazaspiro[3.5]nonan-2-yl)methanone;
(1H-benzo[d][1,2,3]triazol-5-yl)(7-(5-(4-chlorophenyl)-1,3,4-thiadiazol-2-yl)-2,7-diazaspiro[3.5]nonan-2-yl)methanone;
2-(1H-benzo[d][1,2,3]triazole-5-carbonyl)-N-(3,5-dichlorobenzyl)-2,7-diazaspiro[3.5]nonane-7-carboxamide;
(2-(1H-benzo[d][1,2,3]triazole-5-carbonyl)-2,7-diazaspiro[3.5]nonan-7-yl)(5-chloroisoindolin-2-yl)methanone;
benzyl 2-(2-oxo-2,3-dihydrobenzo[d]oxazol-6-ylamino)-7-azaspiro[3.5]nonane-7-carboxylate;
4-chloro-3-fluorobenzyl 2-(1H-benzo[d][1,2,3]triazole-5-carbonyl)-2,7-diazaspiro[3.5]nonane-7-carboxylate;
(2,6-dichloropyridin-4-yl)methyl 2-(1H-benzo[d][1,2,3]triazole-5-carbonyl)-2,7-diazaspiro[3.5]nonane-7-carboxylate;
3,4-dichlorobenzyl 2-(1H-benzo[d][1,2,3]triazole-5-carbonyl)-2,7-diazaspiro[3.5]nonane-7-carboxylate;
(5,6-dichloropyridin-3-yl)methyl 2-(1H-benzo[d][1,2,3]triazole-5-carbonyl)-2,7-diazaspiro[3.5]nonane-7-carboxylate;
2,4-dichlorobenzyl 2-(1H-benzo[d][1,2,3]triazole-5-carbonyl)-2,7-diazaspiro[3.5]nonane-7-carboxylate;
(6-chloropyridin-3-yl)methyl 2-(1H-benzo[d][1,2,3]triazole-5-carbonyl)-2,7-diazaspiro[3.5]nonane-7-carboxylate;
4-chloro-3-(methylsulfonyl)benzyl 2-(1H-benzo[d][1,2,3]triazole-5-carbonyl)-2,7-diazaspiro[3.5]nonane-7-carboxylate;
1-(3,5-dichlorophenyl)ethyl 2-(1H-benzo[d][1,2,3]triazole-5-carbonyl)-2,7-diazaspiro[3.5]nonane-7-carboxylate;
(5-chloropyridin-3-yl)methyl 2-(1H-benzo[d][1,2,3]triazole-5-carbonyl)-2,7-diazaspiro[3.5]nonane-7-carboxylate;
(5-bromopyridin-3-yl)methyl 2-(1H-benzo[d][1,2,3]triazole-5-carbonyl)-2,7-diazaspiro[3.5]nonane-7-carboxylate;
(4,6-dichloropyridin-2-yl)methyl 2-(1H-benzo[d][1,2,3]triazole-5-carbonyl)-2,7-diazaspiro[3.5]nonane-7-carboxylate;
3-chloro-4-fluorobenzyl 2-(1H-benzo[d][1,2,3]triazole-5-carbonyl)-2,7-diazaspiro[3.5]nonane-7-carboxylate;
(5-chlorothiophen-3-yl)methyl 2-(1H-benzo[d][1,2,3]triazole-5-carbonyl)-2,7-diazaspiro[3.5]nonane-7-carboxylate;
thiophen-3-ylmethyl 2-(1H-benzo[d][1,2,3]triazole-5-carbonyl)-2,7-diazaspiro[3.5]nonane-7-carboxylate;
(5-bromothiophen-3-yl)methyl 2-(1H-benzo[d][1,2,3]triazole-5-carbonyl)-2,7-diazaspiro[3.5]nonane-7-carboxylate;
4-(trifluoromethyl)benzyl 2-(1H-benzo[d][1,2,3]triazole-5-carbonyl)-2,7-diazaspiro[3.5]nonane-7-carboxylate;
3,5-dichlorobenzyl 7-(1H-benzo[d][1,2,3]triazole-5-carbonyl)-2,7-diazaspiro[4.4]nonane-2-carboxylate;
2,4,6-trichlorobenzyl 2-(1H-benzo[d][1,2,3]triazole-5-carbonyl)-2,7-diazaspiro[3.5]nonane-7-carboxylate;
6-[(1H-benzotriazole-5-carbonyl)-amino]-2-aza-spiro[3.3]heptane-2-carboxylic acid 3-chloro-5-trifluoromethoxy-benzyl ester;
6-[(1H-benzotriazole-5-carbonyl)-amino]-2-aza-spiro[3.3]heptane-2-carboxylic acid 3-trifluoromethyl-benzyl ester;
6-[(1H-benzotriazole-5-carbonyl)-amino]-2-aza-spiro[3.3]heptane-2-carboxylic acid 3-chloro-5-cyano-benzyl ester;
6-[(1H-benzotriazole-5-carbonyl)-amino]-2-aza-spiro[3.3]heptane-2-carboxylic acid 3-chloro-4-fluoro-benzyl ester;
4-(trifluoromethyl)benzyl 2-(2-oxo-2,3-dihydrobenzo[d]oxazole-6-carbonyl)-2,7-diazaspiro[3.5]nonane-7-carboxylate;
6-[(1H-benzotriazole-5-carbonyl)-amino]-2-aza-spiro[3.3]heptane-2-carboxylic acid 3-fluoro-5-trifluoromethyl-benzyl ester;
6-[(1H-benzotriazole-5-carbonyl)-amino]-2-aza-spiro[3.3]heptane-2-carboxylic acid 3-chloro-4-methyl-benzyl ester;
3-(methylsulfonyl)-5-(trifluoromethyl)benzyl 2-(1H-benzo[d][1,2,3]triazole-5-carbonyl)-2,7-diazaspiro[3.5]nonane-7-carboxylate;
3-(methylsulfonyl)-5-(trifluoromethyl)benzyl 2-(2-oxo-2,3-dihydrobenzo[d]oxazole-6-carbonyl)-2,7-diazaspiro[3.5]nonane-7-carboxylate;
4-chloro-2-(methylsulfonyl)benzyl 2-(1H-benzo[d][1,2,3]triazole-5-carbonyl)-2,7-diazaspiro[3.5]nonane-7-carboxylate;
2-chloro-4-(methylsulfonyl)benzyl 2-(1H-benzo[d][1,2,3]triazole-5-carbonyl)-2,7-diazaspiro[3.5]nonane-7-carboxylate;
3,5-dichlorobenzyl 6-(1H-benzo[d][1,2,3]triazol-5-ylcarbamoyl)spiro[3.3]heptan-2-ylcarbamate;
3-fluoro-5-(trifluoromethoxy)benzyl 2-(1H-benzo[d][1,2,3]triazole-5-carbonyl)-2,7-diazaspiro[4.5]decane-7-carboxylate;
3-chloro-5-(methylsulfonyl)benzyl 2-(2-oxo-2,3-dihydrobenzo[d]oxazol-6-ylsulfonyl)-2,7-diazaspiro[3.5]nonane-7-carboxylate;
2-[(3H-[1,2,3]triazol-4-ylmethyl)-carbamoyl]-7-aza-spiro[3.5]nonane-7-carboxylic acid 3,5-dichloro-benzyl ester;
and pharmaceutically acceptable salts thereof.

Also particular examples of compounds of formula (I) as described herein are selected from 4-(trifluoromethoxy)benzyl 2-(4-sulfamoylbenzoyl)-2,7-diazaspiro[3.5]nonane-7-carboxylate;

2-fluoro-4-(trifluoromethoxy)benzyl 2-(4-sulfamoylbenzoyl)-2,7-diazaspiro[3.5]nonane-7-carboxylate;

1-(2-(1H-benzo[d][1,2,3]triazole-5-carbonyl)-2,7-diazaspiro[3.5]nonan-7-yl)-3-(4-(trifluoromethoxy)phenyl)propan-1-one;

3-isopropyl-4-(2-oxo-2-(2-(4,5,6,7-tetrahydro-1H-benzo[d][1,2,3]triazole-5-carbonyl)-2,7-diazaspiro[3.5]nonan-7-yl)ethoxy)benzonitrile;

1-(2-(1H-benzo[d][1,2,3]triazole-5-carbonyl)-2,7-diazaspiro[3.5]nonan-7-yl)-2-(4-chloro-2-isopropylphenoxy)ethanone;

2-(4-chloro-2-isopropylphenoxy)-1-(2-(4,5,6,7-tetrahydro-1H-benzo[d][1,2,3]triazole-5-carbonyl)-2,7-diazaspiro[3.5]nonan-7-yl)ethanone;

1-(2-(4,5,6,7-tetrahydro-1H-benzo[d][1,2,3]triazole-5-carbonyl)-2,7-diazaspiro[3.5]nonan-7-yl)-3-(4-(trifluoromethoxy)phenyl)propan-1-one;

1-(2-(1H-benzo[d][1,2,3]triazole-5-carbonyl)-2,7-diazaspiro[3.5]nonan-7-yl)-3-(3-chlorophenyl)prop-2-yn-1-one;

1-(2-(1H-benzo[d][1,2,3]triazole-5-carbonyl)-2,7-diazaspiro[3.5]nonan-7-yl)-3-(4-chlorophenyl)prop-2-yn-1-one;

3-fluoro-4-(trifluoromethoxy)benzyl 7-(4,5,6,7-tetrahydro-1H-benzo[d][1,2,3]triazole-5-carbonyl)-2,7-diazaspiro[3.5]nonane-2-carboxylate;

4-(trifluoromethoxy)benzyl 7-(4,5,6,7-tetrahydro-1H-benzo[d][1,2,3]triazole-5-carbonyl)-2,7-diazaspiro[3.5]nonane-2-carboxylate;

[4-(trifluoromethyl)phenyl]methyl 2-(3a,4,5,6,7,7a-hexahydro-1H-benzotriazole-5-carbonyl)-2,7-diazaspiro[3.5]nonane-7-carboxylate;

[2-fluoro-4-(trifluoromethyl)phenyl]methyl 2-(4,5,6,7-tetrahydro-1H-benzotriazole-5-carbonyl)-2,7-diazaspiro[3.5]nonane-7-carboxylate;

[2-methyl-4-(trifluoromethoxy)phenyl]methyl 2-(4,5,6,7-tetrahydro-1H-benzotriazole-5-carbonyl)-2,7-diazaspiro[3.5]nonane-7-carboxylate;

2-fluoro-4-(2,2,2-trifluoroethoxy)benzyl 2-(4,5,6,7-tetrahydro-1H-benzo[d][1,2,3]triazole-6-carbonyl)-2,7-diazaspiro[3.5]nonane-7-carboxylate;

4-(2,2,2-trifluoroethoxy)benzyl 2-(4,5,6,7-tetrahydro-1H-benzo[d][1,2,3]triazole-6-carbonyl)-2,7-diazaspiro[3.5]nonane-7-carboxylate;

3-fluoro-4-(2,2,2-trifluoroethoxy)benzyl 2-(4,5,6,7-tetrahydro-1H-benzo[d][1,2,3]triazole-6-carbonyl)-2,7-diazaspiro[3.5]nonane-7-carboxylate;

2-fluoro-4-(trifluoromethoxy)benzyl 7-(4,5,6,7-tetrahydro-1H-benzo[d][1,2,3]triazole-5-carbonyl)-2,7-diazaspiro[3.5]nonane-2-carboxylate;

2-fluoro-4-(trifluoromethoxy)benzyl 2-(4,5,6,7-tetrahydro-1H-benzo[d][1,2,3]triazole-5-carbonyl)-2,7-diazaspiro[3.5]nonane-7-carboxylate;

4-(trifluoromethoxy)benzyl 2-(4,5,6,7-tetrahydro-1H-benzo[d][1,2,3]triazole-5-carbonyl)-2,7-diazaspiro[3.5]nonane-7-carboxylate;

3-chloro-5-(trifluoromethyl)benzyl 2-(1H-benzo[d][1,2,3]triazole-5-carbonyl)-2,7-diazaspiro[3.5]nonane-7-carboxylate;

3-(methylsulfonyl)-5-(trifluoromethyl)benzyl 2-(2-oxo-2,3-dihydrobenzo[d]oxazol-6-ylsulfonyl)-2,7-diazaspiro[3.5]nonane-7-carboxylate;

4-(trifluoromethoxy)benzyl 2-(4,5,6,7-tetrahydro-1H-[1,2,3]triazolo[4,5-c]pyridine-5-carbonyl)-2,7-diazaspiro[3.5]nonane-7-carboxylate;

2-fluoro-4-(trifluoromethoxy)benzyl 2-(4,5,6,7-tetrahydro-1H-[1,2,3]triazolo[4,5-c]pyridine-5-carbonyl)-2,7-diazaspiro[3.5]nonane-7-carboxylate;

[4-(trifluoromethoxy)phenyl]methyl 2-((1H-triazol-4-ylmethyl)carbamoyl)-2,7-diazaspiro[3.5]nonane-7-carboxylate;

[2-fluoro-4-(trifluoromethoxy)phenyl]methyl 2-((1H-triazol-4-ylmethyl)carbamoyl)-2,7-diazaspiro[3.5]nonane-7-carboxylate;

(−)-2-fluoro-4-(trifluoromethoxy)benzyl 2-(4,5,6,7-tetrahydro-1H-benzo[d][1,2,3]triazole-5-carbonyl)-2,7-diazaspiro[3.5]nonane-7-carboxylate;

(+)-2-fluoro-4-(trifluoromethoxy)benzyl 2-(4,5,6,7-tetrahydro-1H-benzo[d][1,2,3]triazole-5-carbonyl)-2,7-diazaspiro[3.5]nonane-7-carboxylate;

[2-fluoro-4-(trifluoromethyl)phenyl]methyl 2-[4,5,6,7-tetrahydro-1H-benzotriazole-5-carbonyl]-2,7-diazaspiro[3.5]nonane-7-carboxylate (enantiomer A);

[2-fluoro-4-(trifluoromethyl)phenyl]methyl 2-[4,5,6,7-tetrahydro-1H-benzotriazole-5-carbonyl]-2,7-diazaspiro[3.5]nonane-7-carboxylate (enantiomer B);

and pharmaceutically acceptable salts thereof.

Further particular examples of compounds of formula (I) as described herein are selected from 3,5-dichlorobenzyl 2-(1H-benzo[d][1,2,3]triazole-5-carbonyl)-2,7-diazaspiro[3.5]nonane-7-carboxylate;

3-chloro-5-(methylsulfonyl)benzyl 2-(1H-benzo[d][1,2,3]triazole-5-carbonyl)-2,7-diazaspiro[3.5]nonane-7-carboxylate;

3-chloro-5-(methylsulfonyl)benzyl 2-(2-oxo-2,3-dihydrobenzo[d]oxazole-6-carbonyl)-2,7-diazaspiro[3.5]nonane-7-carboxylate;

3,5-dichlorobenzyl 2-(2-oxo-2,3-dihydrobenzo[d]oxazole-6-carbonyl)-2,7-diazaspiro[3.5]nonane-7-carboxylate;

(E)-1-(2-(1H-benzo[d][1,2,3]triazole-5-carbonyl)-2,7-diazaspiro[3.5]nonan-7-yl)-3-(3,5-dichlorophenyl)prop-2-en-1-one;

3-(methylsulfonyl)-5-(trifluoromethyl)benzyl 2-(1H-benzo[d][1,2,3]triazole-5-carbonyl)-2,7-diazaspiro[3.5]nonane-7-carboxylate;

[2-methyl-4-(trifluoromethoxy)phenyl]methyl 2-(4,5,6,7-tetrahydro-1H-benzotriazole-5-carbonyl)-2,7-diazaspiro[3.5]nonane-7-carboxylate;

(+)-2-fluoro-4-(trifluoromethoxy)benzyl 2-(4,5,6,7-tetrahydro-1H-benzo[d][1,2,3]triazole-5-carbonyl)-2,7-diazaspiro[3.5]nonane-7-carboxylate;

and pharmaceutically acceptable salts thereof.

Also further particular examples of compounds of formula (I) as described herein are selected from 3,5-dichlorobenzyl 2-(1H-benzo[d][1,2,3]triazole-5-carbonyl)-2,7-diazaspiro[3.5]nonane-7-carboxylate;

3-chloro-5-(methylsulfonyl)benzyl 2-(1H-benzo[d][1,2,3]triazole-5-carbonyl)-2,7-diazaspiro[3.5]nonane-7-carboxylate;

3-chloro-5-(methylsulfonyl)benzyl 2-(2-oxo-2,3-dihydrobenzo[d]oxazole-6-carbonyl)-2,7-diazaspiro[3.5]nonane-7-carboxylate;

3,5-dichlorobenzyl 2-(2-oxo-2,3-dihydrobenzo[d]oxazole-6-carbonyl)-2,7-diazaspiro[3.5]nonane-7-carboxylate;

(E)-1-(2-(1H-benzo[d][1,2,3]triazole-5-carbonyl)-2,7-diazaspiro[3.5]nonan-7-yl)-3-(3,5-dichlorophenyeprop-2-en-1-one;

3-(methylsulfonyl)-5-(trifluoromethyl)benzyl 2-(1H-benzo[d][1,2,3]triazole-5-carbonyl)-2,7-diazaspiro[3.5]nonane-7-carboxylate;

and pharmaceutically acceptable salts thereof.

General Synthetic Procedures

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein.

Compounds of general formula (I) can be synthesised from amine precursor H—W—R² (1) and appropriate reagents, using methods well known in the art.

For instance, amine 1 is reacted with a suitable chloroformate ester of formula R¹—O—C(O)—Cl (2), or with an imidazole-1-carboxylate ester of formula (3A), or with a succinimidyl carbonate derivative of formula (3B), leading to compound of formula (I) wherein Y is —OC(O)—.

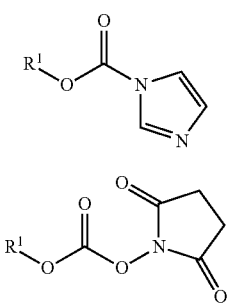

The reaction is performed in a suitable solvent such as dichloromethane, tetrahydrofuran, N,N-dimethylformamide, acetonitrile, acetone, water, or mixtures thereof, in the presence or not of a base, e.g., triethylamine, diisopropylethylamine, pyridine, potassium hydrogencarbonate, potassium carbonate, at temperatures between 0° C. and the boiling point of the solvent or solvent mixture.

Chloroformate esters 2 are commercially available or can be synthesised from the corresponding alcohol of formula R¹—OH, by reaction with phosgene or a phosgene equivalent (e.g., diphosgene, triphosgene) by methods known to those skilled in the art.

Imidazole-1-carboxylate esters 3A are synthesised from the corresponding alcohols of formula R¹—OH, by reaction with 1,1'-carbonyldiimidazole. The reaction is performed at room temperature, in a solvent such as dichloromethane, tetrahydrofuran, or acetonitrile. The imidazole-1-carboxylate esters 3A are typically not isolated but directly reacted with amines 1 as described above.

Succinimidyl carbonate derivatives 3B are synthesised from the corresponding alcohols of formula R¹—OH, by reaction with N,N'-disuccinimidyl carbonate. The reaction is performed at room temperature, in a solvent such as dichloromethane, tetrahydrofuran, or acetonitrile, optionally in the presence of a base, e.g., triethylamine. The succinimidyl carbonate derivatives 3B are typically not isolated but directly reacted with amines 1 as described above.

Alcohols of formula R¹—OH are commercially available or can be produced by method described herein or known in the art.

Alternatively, amine 1 is reacted with a suitable N-(chlorocarbonyl)amine of formula R¹—N(R¹⁴)—C(O)—Cl (4), or, in the case where R¹⁴ is H, with isocyanate of formula R¹—NCO (5), leading to compound of formula (I) wherein Y is —NR¹⁴C(O)—.

N—(Chlorocarbonyl)amines (4) are synthesised from the corresponding amines of formula R¹—N(R¹⁴)H by reaction with phosgene or a phosgene equivalent, as described in the literature.

Isocyanates 5 are commercially available or can be prepared from the corresponding amines of formula R¹—NH₂, by reaction with phosgene or a phosgene equivalent (e.g., diphosgene, triphosgene, 1,1'-carbonyldiimidazole), as described in the literature.

Alternatively, amine 1 is reacted with a suitable carboxylic acid of formula R¹—COOH (6) leading to compound of formula (I), wherein Y is —C(O)—. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N', N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Amine 1 can also be reacted with suitable acylating reagents, such as acyl chlorides of formula R¹—COCl (7) to lead to compounds of formula (I) wherein Y is —C(O)—. The reaction is performed in a solvent such as dichloromethane, tetrahydrofuran, or N,N-dimethylformamide, in the presence of a base such as triethylamine or 4-methylmorpholine, at temperatures between 0° C. and 80° C.

Carboxylic acids (6) and acyl halides (7) are commercially available or can be prepared as described herein or in the literature.

Alternatively, amine 1 is reacted with a suitable sulfonyl chloride of formula R¹—SO₂Cl (8), leading to compounds of formula (I) wherein Y is —S(O₂)—. The reaction is performed in a suitable solvent such as dichloromethane, tetrahydrofuran, N,N-dimethylformamide, acetonitrile, acetone, water, or mixtures thereof, in the presence of a base, e.g., triethylamine, diisopropylethylamine, pyridine, potassium hydrogencarbonate, potassium carbonate, at temperatures between 0° C. and the boiling point of the solvent or solvent mixture.

Sulfonyl chlorides (8) are commercially available or can be synthesised as described herein or in the literature.

Alternatively, amine 1 is reacted with a suitable chlorooxadiazole reagent of general formula 9, or with oxadiazolone reagent 10, leading to compound of formula (I), wherein Y is

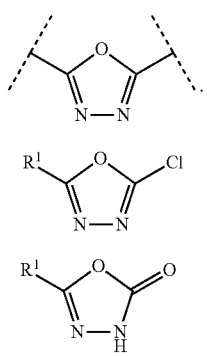

In the case where compound s of formula (I) are produced from amine 1 and chloro-oxadiazole 9, the reaction is performed in the presence of a base, e.g., potassium carbonate, triethylamine, or 1,8-diazabicyclo[5.4.0]undec-7-ene, in a solvent such as toluene, ethanol, N,N-dimethylformamide, or 1,4-dioxane, at temperatures between 20° C. and 150° C.

In the case where compounds of formula (I) are produced from amine 1 and oxadiazolone 10, the reaction is performed in the presence of a coupling agent, e.g., benzotriazol-1-yl-oxy-tris-(dimethylamino)-phosphonium hexafluorophosphate, and a base, e.g., diisopropylethylamine or 4-methylmorpholine, in a solvent such as N,N-dimethylformamide, at temperatures between 20° C. and 100° C., as described in the literature (*Org. Lett.* 2008, 10, 1755).

Oxadiazolones 10 are commercially available or can be produced as described in the experimental section.

Chloro-oxadiazoles 9 are commercially available or can be produced from the corresponding oxadiazolones, by reaction with a suitable halogenating reagent, e.g., phosphorus oxychloride and/or phosphorus pentachloride, at temperatures between 60° C. and 120° C.

Alternatively, amine 1 is reacted with a suitable halo-thiadiazole reagent of general formula II (X=Cl or Br), or with thiadiazolethione reagent 12, leading to compounds of (I) wherein Y is

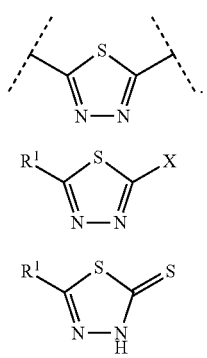

In the case where compounds of formula (I) are produced from amine 1 and halo-thiadiazole 11, the reaction is performed in the presence of a base, e.g., potassium carbonate, triethylamine, or 1,8-diazabicyclo[5.4.0]undec-7-ene, in a solvent such as toluene, ethanol, N,N-dimethylformamide, or 1,4-dioxane, at temperatures between 20° C. and 150° C.

In the case where compounds of formula (I) are produced from amine 1 and thiadiazolethione 12, the reaction is performed in a solvent such as ethanol or N,N-dimethylformamide, at temperatures between 20° C. and 100° C., as described in the literature.

Thiadiazolethiones 12 are commercially available or can be produced as described in the literature.

Halo-thiadiazoles 11 are commercially available or can be produced as described in the literature.

Amines of general formula H—W—$R^2$ (1) are synthesised from suitably protected precursors, PG—W—$R^2$ (13). Suitable protective groups (PG) are tert-butoxycarbonyl benzyloxycarbonyl and substituted benzyloxycarbonyl such as 3,5-dichloro benzyloxycarbonyl. The deprotection of intermediates 13 can be performed using methods and reagents known in the art.

For instance, in the case where PG is optionally substituted benzyloxycarbonyl, the deprotection may be performed by hydrogenation at pressures between 1 bar and 100 bar, in the presence of a suitable catalyst such as palladium on activated charcoal, at temperatures between 20° C. and 150° C., in solvents such as methanol or ethanol.

Alternatively, in the case where PG is tert-butoxycarbonyl, the deprotection may be performed in the presence of a suitable acid, e.g, hydrochloric acid or trifluoroacetic acid, in a solvent such as water, 2-propanol, dichloromethane, or 1,4-dioxane, at temperatures between 0° C. and 30° C.

Carbamates 13, wherein W is A, B, C, D, E, F, G, H, I, J, K, L, M, N, P or Q are represented by general structure PG—W—$R^2$ (13A). PG is a suitable protective group, e.g., tert-butoxycarbonyl, benzyloxycarbonyl and substituted benzyloxycarbonyl such as 3,5-dichloro benzyloxycarbonyl.

Carbamates 13A can be produced from amine precursors of general formula PG—W—H (14) by reaction with appropriate reagents, using methods known in the art.

For instance, 14 is reacted with alkylating agents of general formula X—$(CR^4R^5)_n$—$R^3$ (15) where X is a leaving group such as Cl, Br, I, or $OSO_2CH_3$, leading to 13A, wherein $R^2$ is —$(CR^4R^5)_n$—$R^3$. This reaction is performed in a solvent such as tetrahydrofuran or N,N-dimethylformamide, in the presence of a base, e.g., triethylamine or potassium carbonate, at temperatures between 0° C. and 100° C.

Alternatively, compounds of formula 13A, wherein $R^2$ is —$(CR^4R^5)_n R^3$, $R^4$ is hydrogen, alkyl or cycloalkyl, $R^5$ is H and n is 1, amine 14 is reacted with aldehydes or ketones of general formula $R^4$—C(O)—$R^3$ (16) in a reductive amination reaction, leading to 13A. This reaction is performed in the presence of a suitable reducing agent, e.g., sodium borohydride or sodium triacetoxyborohydride, in a solvent such as methanol, acetic acid, tetrahydrofuran, 1,2-dichloroethane, or mixtures thereof, at temperatures between 0° C. and 50° C.

Alternatively, amine 14 is reacted with a suitable carboxylic acid of formula $R^3$—COOH (17), leading to compounds of formula 13A, wherein $R^2$ is —C(O)—$R^3$. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, 0-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C., in the presence or absence of a base such as triethylamine, diisopropylethylamine, 4-methylmorpholine and/or 4-(dimethylamino)pyridine.

Alternatively, amine 14 is reacted with a suitable sulfonyl chloride of formula $R^3$—$SO_2Cl$ (18), leading to compounds of formula 13A, wherein $R^2$ is —$S(O_2)$—$R^3$, The reaction is performed in a suitable solvent such as dichloromethane, tetrahydrofuran, N,N-dimethylformamide, acetonitrile, acetone, water, or mixtures thereof, in the presence of a base, e.g., triethylamine, diisopropylethylamine, pyridine, potassium hydrogencarbonate, potassium carbonate, at temperatures between 0° C. and the boiling point of the solvent or solvent mixture.

Alternatively, amine 14 is reacted with a suitable N-(chlorocarbonyl)amine of formula $R^3$—$N(R^6)$—$C(O)$—$Cl$ (19) leading to compounds of formula 13A, wherein $R^2$ is —$C(O)$—$NR^6R^3$, or with isocyanate of formula $R^3$—NCO (20), leading to compounds of formula 13A, wherein $R^2$ is —$C(O)$—$NR^6R^3$ and $R^6$ is H.

Alternatively, amine 14 is reacted with phosgene or a phosgene equivalent (diphosgene, triphosgene) in the presence of a base (e.g., pyridine, triethylamine), in a solvent such as dichloromethane or tetrahydrofuran, to the corresponding N-(chlorocarbonyl)amine of formula PG—W—C(O)Cl (21), which is then reacted with an amine of formula $HN(R^6)R^3$ (22), leading to compounds of formula 13A, wherein $R^2$ is —$C(O)$—$NR^6R^3$.

N—(Chlorocarbonyl)amines 19 are synthesised from the corresponding amines 22 by reaction with phosgene or a phosgene equivalent (diphosgene, triphosgene), as described in the literature.

Isocyanates 20 are commercially available or can be prepared from the corresponding amines of formula $R^3$—$NH_2$, by reaction with phosgene or a phosgene equivalent (e.g., diphosgene, triphosgene, 1,1'-carbonyldiimidazole), as described in the literature.

Amines 14, alkylating agents 15, aldehydes/ketones 16, carboxylic acids 17, sulfonyl chlorides 18, and amines 22 are commercially available or can be synthesised as described in the experimental section.

Carbamates 13 wherein W is C or H, $R^2$ is —$(CR^4R^5)_n$—$R^3$ and n is zero are represented by general formula 13B, wherein p is 1 or 2 and PG is a suitable protective group, e.g tert-butoxycarbonyl benzyloxycarbonyl and substituted benzyloxycarbonyl such as 3,5-dichloro benzyloxycarbonyl.

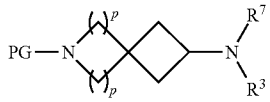

13B

Compound 13B is produced from ketone 23, wherein p is 1 or 2 by reaction with an amine of formula $HN(R^7)R^3$ (24) in the presence of a suitable reducing agent, e.g., sodium borohydride or sodium triacetoxyborohydride, in a solvent such as methanol, acetic acid, tetrahydrofuran, 1,2-dichloroethane, or mixtures thereof, at temperatures between 0° C. and 50° C.

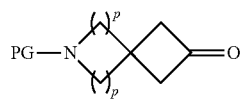

23

Ketones 23 and amines 24 are commercially available or can be prepared as described in the experimental section.

Carbamates 13 in W is O or R and $R^2$ is —$C(O)$—$N(R^6)R^3$ are represented by general formula 13C.

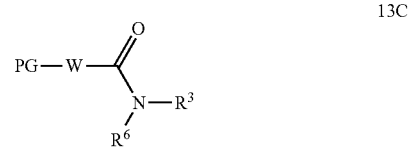

13C

Amide 13C is produced from carboxylic acid 25 by coupling reaction with an amine of formula $HN(R^6)R^3$ (22).

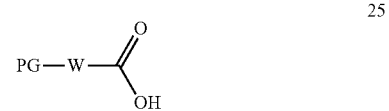

25

The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Carboxylic acids 25 are commercially available or can be produced as described in the literature.

Compounds of formula (I), wherein W is A, B, C, D, E, F, G, H, I, J, K, L, M, N, P or Q can be produced from amine precursors of general formula $R^1$—Y—W—H (26) by reaction with appropriate reagents, using methods known in the art.

For instance, an amine of formula 26 is reacted with alkylating agents of general formula X—$(CR^4R^5)_n R^3$ (15) where X is a leaving group such as Cl, Br, I, or $OSO_2CH_3$, leading to compounds of formula (I), wherein W is A, B, C, D, E, F, G, H, I, J, K, L, M, N, P or Q and $R^2$ is —$(CR^4R^5)_n$—$R^3$. This reaction is performed in a solvent such as tetrahydrofuran or N,N-dimethylformamide, in the presence of a base, e.g., triethylamine or potassium carbonate, at temperatures between 0° C. and 100° C.

Alternatively, an amine of formula 26 is reacted with aldehydes or ketones of general formula $R^4$—$C(O)$—$R^3$ (16) in a reductive amination reaction, leading to compounds of formula (I) wherein W is A, B, C, D, E, F, G, H, I, J, K, L, M, N, P or Q, $R^2$ is —$(CR^4R^5)_n$—$R^3$, $R^4$ is hydrogen, alkyl or cycloalkyl, $R^5$ is H and n is 1. This reaction is performed in the presence of a suitable reducing agent, e.g., sodium borohydride or sodium triacetoxyborohydride, in a solvent such as methanol, acetic acid, tetrahydrofuran, 1,2-dichloroethane, or mixtures thereof, at temperatures between 0° C. and 50° C.

Alternatively, amine 26 is reacted with a suitable carboxylic acid of formula $R^3$—COOH (17), leading to compounds of formula (I) wherein W is A, B, C, D, E, F, G, H, I, J, K, L, M, N, P or Q and $R^2$ is —C(O)—$R^3$. The reaction is performed in the presence a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Alternatively, amine 26 is reacted with a suitable sulfonyl chloride of formula $R^3$—$SO_2Cl$ (18), leading to wherein W is A, B, C, D, E, F, G, H, I, J, K, L, M, N, P or Q and $R^2$ is —$S(O_2)$—$R^3$. The reaction is performed in a suitable solvent such as dichloromethane, tetrahydrofuran, N,N-dimethylformamide, acetonitrile, acetone, water, or mixtures thereof, in the presence of a base, e.g., triethylamine, diisopropylethylamine, pyridine, potassium hydrogencarbonate, potassium carbonate, at temperatures between 0° C. and the boiling point of the solvent or solvent mixture.

Alternatively, an amine of formula 26 is reacted with a suitable N-(chlorocarbonyl)amine of formula $R^3$—N($R^6$)—C(O)—Cl (19) leading to compounds of formula (I), wherein $R^2$ is —C(O)—$NR^6R^3$, or with isocyanate $R^3$—NCO (20), leading to compounds of formula (I), wherein $R^2$ is —C(O)—$NR^6R^3$ and $R^6$ is H.

Amines 26 can be synthesised from their tert-butyl carbamate derivatives of formula $R^1$—Y—W—C(O)O—C($CH_3$)$_3$ (27) by carbamate deprotection. The deprotection may be performed in the presence of a suitable acid, e.g, hydrochloric acid or trifluoroacetic acid, in a solvent such as water, 2-propanol, dichloromethane, or 1,4-dioxane, at temperatures between 0° C. and 30° C.

Tert-Butyl carbamates 27 can be synthesised from an amine precursor of formula H—W—C(O)O—C($CH_3$)$_3$ (28) and appropriate reagents, using methods well known in the art.

For instance, an amine of formula 28 is reacted with a suitable chloroformate ester of formula $R^1$—O—C(O)—Cl (2), or with an imidazole-1-carboxylate ester of formula (3A) or with a succinimidyl carbonate derivative of formula (3B), leading to compounds of formula 27, wherein Y is —OC(O)—. The reaction is performed in a suitable solvent such as dichloromethane, tetrahydrofuran, N,N-dimethylformamide, acetonitrile, acetone, water, or mixtures thereof, in the presence or not of a base, e.g., triethylamine, diisopropylethylamine, pyridine, potassium hydrogencarbonate, potassium carbonate, at temperatures between 0° C. and the boiling point of the solvent or solvent mixture.

Alternatively, an amine of formula 28 is reacted with a suitable N-(chlorocarbonyl)amine of formula $R^1$—N($R^{14}$)—C(O)—Cl (4) leading to compounds of formula 27, wherein Y is —$NR^{14}C(O)$—, or with an isocyanate of formula $R^1$—NCO (5) leading to leading to compounds of formula 27, wherein Y is —$NR^{14}C(O)$— and $R^{14}$ is H.

Alternatively, amine 28 is reacted with a suitable carboxylic acid of formula $R^1$—COOH (6) leading to compounds of formula 27, wherein Y is —C(O)—. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Amine 28 can also be reacted with suitable acylating reagents, such as acyl chlorides of formula $R^1$—COCl (7) to lead to compounds of formula 27, wherein Y is —C(O)—. The reaction is performed in a solvent such as dichloromethane, tetrahydrofuran, or N,N-dimethylformamide, in the presence of a base such as triethylamine or 4-methylmorpholine, at temperatures between 0° C. and 80° C.

Alternatively, amine 1 is reacted with a suitable sulfonyl chloride of formula $R^1$—$SO_2Cl$ (8), leading to compounds of formula 27, wherein Y is —$S(O_2)$—. The reaction is performed in a suitable solvent such as dichloromethane, tetrahydrofuran, N,N-dimethylformamide, acetonitrile, acetone, water, or mixtures thereof, in the presence of a base, e.g., triethylamine, diisopropylethylamine, pyridine, potassium hydrogencarbonate, potassium carbonate, at temperatures between 0° C. and the boiling point of the solvent or solvent mixture.

Alternatively, amine 28 is reacted with a suitable chloro-oxadiazole reagent of general formula 9, or with oxadiazolone reagent 10, leading to compounds of formula 27, wherein Y is

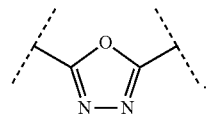

In the case where 27 is produced from amine 28 and chloro-oxadiazole 9, the reaction is performed in the presence of a base, e.g., potassium carbonate, triethylamine, or 1,8-diazabicyclo[5.4.0]undec-7-ene, in a solvent such as toluene, ethanol, N,N-dimethylformamide, or 1,4-dioxane, at temperatures between 20° C. and 150° C.

In the case where 27 is produced from amine 28 and oxadiazolone 10, the reaction is performed in the presence of a coupling agent, e.g., benzotriazol-1-yl-oxy-tris-(dimethylamino)-phosphonium hexafluorophosphate, and a base, e.g., diisopropylethylamine or 4-methylmorpholine, in a solvent such as N,N-dimethylformamide, at temperatures between 20° C. and 100° C., as described in the literature (*Org. Lett.* 2008, 10, 1755).

Alternatively, amine 28 is reacted with a suitable halothiadiazole reagent of general formula II (X is Cl or Br), or with thiadiazolethione reagent 12, leading to compounds of formula 27, wherein Y is

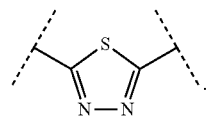

In the case where 27 is produced from amine 28 and halo-thiadiazole 11, the reaction is performed in the presence of a base, e.g., potassium carbonate, triethylamine, or 1,8-diazabicyclo[5.4.0]undec-7-ene, in a solvent such as toluene, ethanol, N,N-dimethylformamide, or 1,4-dioxane, at temperatures between 20° C. and 150° C.

In the case where 27 is produced from amine 28 and thiadiazolethione 12, the reaction is performed in a solvent such as ethanol or N,N-dimethylformamide, at temperatures between 20° C. and 100° C., as described in the literature Also an embodiment of the present invention is a process to prepare a compound of formula (I) as defined above comprising a) the reaction of a compound of formula (II) in the presence of a compound of formula

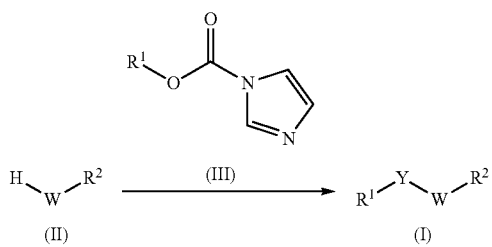

or b) the reaction of a compound of formula (IV) in the presence of a compound of formula (V);

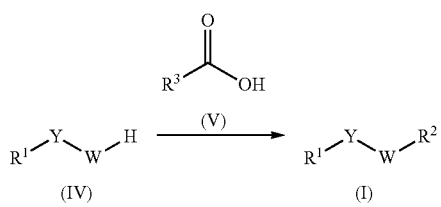

wherein in step a) $R^1$, $R^2$ and W are as defined above, Y is —C(O)— and compounds of formula (I) are of formula (In), and wherein in step b) $R^1$ and Y are as defined above, W is A, B, C, D, E, F, G, H, I, J, K, L, M, N, P or Q and $R^2$ is —C(O)—$R^3$.

In particular, in step a), in the presence of a coupling agent such as O-(7-azabenzotriazol-1-yl)-N,N,N',N'-tetramethyl-uronium hexafluoro-phosphate, in a solvent such as N,N-dimethylformamide, in the presence of a base such as 4-methylmorpholine and at a temperature comprised between −78° C. and reflux, particularly between −10° C. and room temperature.

In particular, in step b), in an aprotic solvent such as acetonitrile, in the presence of a base such as triethylamine and at a temperature comprised between 0° C. and reflux, particularly between room temperature and reflux.

Pharmaceutical Compositions and Methods of Use

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

An object of the invention is the use of a compound according to formula (I) as described herein for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

Renal conditions include, but are not limited to, acute kidney injury and chronic renal disease with and without proteinuria including end-stage renal disease (ESRD). In more detail, this includes decreased creatinine clearance and decreased glomerular filtration rate, micro-albuminuria, albuminuria and proteinuria, glomerulosclerosis with expansion of reticulated mesangial matrix with or without significant hypercellularity (particularly diabetic nephropathy and amyloidosis), focal thrombosis of glomerular capillaries (particularly thrombotic microangiopathies), global fibrinoid necrosis, ischemic lesions, malignant nephrosclerosis (such as ischemic retraction, reduced renal blood flow and renal arteriopathy), swelling and proliferation of intracapillary (endothelial and mesangial) and/or extracapillary cells (crescents) like in glomerular nephritis entities, focal segmental glomerular sclerosis, IgA nephropathy, vasculitides/systemic diseases as well as acute and chronic kidney transplant rejection.

Liver conditions include, but are not limited to, liver cirrhosis, hepatic congestion, cholestatic liver disease including pruritus, nonalcoholic steatohepatitis and acute and chronic liver transplant rejection.

Inflammatory conditions include, but are not limited to, arthritis, osteoarthritis, multiple sclerosis, systemic lupus erythematodes, inflammatory bowel disease, abnormal evacuation disorder and the like as well as inflammatory airways diseases such as idiopathic pulmonary fibrosis (IPF), chronic obstructive pulmonary disease (COPD) or chronic asthma bronchiale.

Further conditions of the respiratory system include, but are not limited to, other diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, silicosis, asbestos induced pulmonary fibrosis or acute respiratory distress syndrome (ARDS).

Conditions of the nervous system include, but are not limited to, neuropathic pain, schizophrenia, neuro-inflammation (e.g. astrogliosis), peripheral and/or autonomic (diabetic) neuropathies and the like.

Vascular conditions include, but are not limited to, atherosclerosis, thrombotic vascular disease as well as thrombotic microangiopathies, proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction and the like.

Cardiovascular conditions include, but are not limited to, acute coronary syndrome, coronary heart disease, myocardial infarction, arterial and pulmonary hypertension, stroke and other vascular damage.

Fibrotic diseases include, but are not limited to myocardial and vascular fibrosis, renal fibrosis, liver fibrosis, pulmonary fibrosis, skin fibrosis, scleroderma and encapsulating peritonitis.

In a particular embodiment, the compounds of formula (I) or their pharmaceutically acceptable salts and esters can be used for the treatment or prophylaxis of organ or skin fibrosis.

In another embodiment, the fibrotic disease is renal tubulo-interstitial fibrosis or glomerulosclerosis.

In another embodiment, the fibrotic disease is non-alcoholic liver steatosis, liver fibrosis or liver cirrhosis.

Cancer and cancer metastasis include, but are not limited to, breast cancer, ovarian cancer, lung cancer, prostate cancer, mesothelioma, glioma, hepatic carcinoma, gastrointestinal cancers and progression and metastatic aggressiveness thereof.

Ocular conditions include, but are not limited to, proliferative and non-proliferative (diabetic) retinopathy, dry and wet age-related macular degeneration (AMD), macular edema, central arterial/venous occlusion, traumatic injury, glaucoma and the like.

Metabolic conditions include, but are not limited to, obesity and diabetes.

In another embodiment, the compounds of formula (I) or their pharmaceutically acceptable salts and esters can be used for the treatment or prophylaxis of cholestatic or non-cholestatic chronic pruritus.

The present invention also relates to the use of a compound according to formula (I) as described herein for the treatment or prophylaxis of renal conditions, liver conditions, inflammatory conditions, conditions of the nervous system, fibrotic diseases and acute and chronic organ transplant rejection.

The present invention also relates to the use of a compound according to formula (I) as described herein for the treatment or prophylaxis of renal conditions, liver conditions and fibrotic diseases.

A particular embodiment of the present invention is a compound according to formula (I) as described herein for the treatment or prophylaxis of renal conditions, liver conditions, inflammatory conditions, conditions of the nervous system, fibrotic diseases and acute and chronic organ transplant rejection.

A particular embodiment of the present invention is a compound according to formula (I) as described herein for the treatment or prophylaxis of renal conditions, liver conditions and fibrotic diseases.

The present invention also relates to the use of a compound according to formula (I) as described herein for the preparation of a medicament for the treatment or prophylaxis of renal conditions, liver conditions, inflammatory conditions, conditions of the nervous system, fibrotic diseases and acute and chronic organ transplant rejection.

The present invention also relates to the use of a compound according to formula (I) as described herein for the preparation of a medicament for the treatment or prophylaxis of renal conditions, liver conditions and fibrotic diseases.

Also an object of the invention is a method for the treatment or prophylaxis of renal conditions, liver conditions, inflammatory conditions, conditions of the nervous system, fibrotic diseases and acute and chronic organ transplant rejection, which method comprises administering an effective amount of a compound according to formula (I) as described herein.

Also an object of the invention is a method for the treatment or prophylaxis of renal conditions, liver conditions and fibrotic diseases, which method comprises administering an effective amount of a compound according to formula (I) as described herein.

In a particular embodiment, the renal condition is selected from the group consisting of acute kidney injury, chronic kidney disease, diabetic nephropathy, acute kidney transplant rejection and chronic allograft nephropathy.

In another particular embodiment, the renal condition is acute kidney injury.

In another particular embodiment, the renal condition is chronic kidney disease.

In a further particular embodiment, the renal condition is diabetic nephropathy.

In another particular embodiment, the renal condition is acute kidney transplant rejection.

In another particular embodiment, the renal condition is chronic allograft nephropathy.

In a particular embodiment, the liver condition is acute and chronic liver transplant rejection In a particular embodiment, the inflammatory condition is arthritis.

In a particular embodiment, the condition of the nervous system is neuropathic pain.

In another embodiment, the fibrotic disease is encapsulating peritonitis

In another embodiment, the fibrotic disease is idiopathic pulmonary fibrosis.

In another embodiment, the fibrotic disease is non-alcoholic liver steatosis, liver fibrosis or liver cirrhosis.

Also an embodiment of the present invention are compounds of formula (I) as described herein, when manufactured according to any one of the described processes.

Assay Procedures

Production of Human Full Length ATX, with and without his Tag

Autotaxin (ATX—ENPP2) Cloning:

cDNA was prepared from commercial human hematopoietic cells total RNA and used as template in overlapping PCR to generate a full length human ENPP2 ORF with or without a 3'-6×His tag. These full length inserts were cloned into the pcDNA3.1V5-His TOPO (Invitrogen) vector. The DNA sequences of several single clones were verified. The DNA from a correct full length clone was used to transfect Hek293 cells for verification of protein expression. The sequence of the encoded ENPP2 conforms to Swissprot entry Q13822, with or without the additional C-terminal 6×His tag.

ATX Fermentation:

Recombinant protein was produced by large-scale transient transfection in 20 L controlled stirred tank bioreactors (Sartorius). During cell growth and transfection, temperature, stirrer speed, pH and dissolved oxygen concentration were maintained at 37° C., 120 rpm, 7.1 and 30% DO, respectively. FreeStyle 293-F cells (Invitrogen) were cultivated in suspension in FreeStyle 293 medium (Invitrogen) and transfected at ca. 1–1.5×10E6 cells/mL with above plasmid DNAs using X-tremeGENE Ro-1539 (commercial product, Roche Diagnostics) as complexing agent. Cells were fed a concentrated nutrient solution (J Immunol Methods 194 (1996), 19, 1-199 (page 193)) and induced by sodium butyrate (2 mM) at 72 h post-transfection and harvested at 96 h post-transfection. Expression was analyzed by Western Blot, enzymatic assay and/or analytical IMAC chromatography. After cooling the cell suspension to 4° C. in a flow-through heat exchanger, cell separation and sterile filtration of supernatant was performed by filtration through Zeta Plus 60MO2 E16 (Cuno) and Sartopore 2 XLG (Sartorius) filter units. The supernatant was stored at 4° C. prior to purification.

ATX Purification:

20 liter of culture supernatant were conditioned for ultrafiltration by adding Brij 35 to a final concentration of 0.02% and by adjusting the pH to 7.0 using 1 M HCl. Then the supernatant was first microfiltred through a 0.2 μm Ultran-Pilot Open Channel PES filter (Whatman) and afterwards concentrated to 1 liter through an Ultran-Pilot Screen Channel PES filter with 30 kDa MWCO (Whatman). Prior to IMAC chromatography, NiSO$_4$ was added to a final concentration of 1 mM. The cleared supernatant was then applied to a H isTrap column (GE Healthcare) previously equlibrated in 50 mM Na$_2$HPO$_4$ pH 7.0, 0.5 M NaCl, 10% glycerol, 0.3% CHAPS, 0.02% NaN$_3$. The column was washed stepwise with the same buffer containing 20 mM, 40 mM and 50 mM imidazole, respectively. The protein was subsequently eluted using a linear gradient to 0.5 M imidazole in 15 column volumes. ATX containing fractions were pooled and concentrated using an Amicon cell equipped with a 30 kDa PES filter membrane. The protein was further purified by size exclusion chromatography on Superdex S-200 prep grade (XK 26/100) (GE Healthcare) in 20 mM BICINE pH 8.5, 0.15 M NaCl, 10% glycerol, 0.3% CHAPS, 0.02% NaN$_3$. Final yield of protein after purification was 5-10 mg ATX per liter of culture supernatant. The protein was stored at −80° C.

Human ATX Enzyme Inhibition Assay

ATX inhibition was measured by a fluorescence quenching assay using a specifically labeled substrate analogue (MR121 substrate). To obtain this MR121 substrate, BOC and TBS protected 6-amino-hexanoic acid (R)-3-({2-[3-(2-{2-[2-(2-amino-ethoxy)-ethoxy]-ethoxy}-ethoxy)-propionylamino]-ethoxy}-hydroxy-phosphoryloxy)-2-hydroxy-propyl ester (Ferguson et al., Org Lett 2006, 8 (10), 2023) was labeled with MR121 fluorophore (CAS 185308-24-1, 143-carboxypropyl)-11-ethyl-1,2,3,4,8,9,10,11-octahydro-dipyrido[3,2-b:2',3'-i]phenoxazin-13-ium) on the free amine of the ethanolamine side and then, after deprotection, subsequently with tryptophan on the side of the aminohexanoic acid.

Assay working solutions were made as follows:
Assay buffer (50 mM Tris-HCl, 140 mM NaCl, 5 mM KCl, 1 mM CaCl$_2$, 1 mM MgCl$_2$, 0.01% Triton-X-100, pH 8.0;
ATX solution: ATX (human His-tagged) stock solution (1.08 mg/mL in 20 mM bicine, pH 8.5, 0.15 M NaCl, 10% glycerol, 0.3% CHAPS, 0.02% NaN$_3$), diluted to 1.4-2.5× final concentration in assay buffer;
MR121 substrate solution: MR121 substrate stock solution (800 μM MR121 substrate in DMSO), diluted to 2-5× final concentration in assay buffer.

Test compounds (10 mM stock in DMSO, 8 μL) were obtained in 384 well sample plates (Corning Costar #3655) and diluted with 8 μL DMSO. Row-wise serial dilutions were made by transferring 8 μL cpd solution to the next row up to row 0. The compound and control solutions were mixed five times and 2 μL were transferred to 384 well assay plates (Corning Costar #3702). Then, 15 μL of 41.7 nM ATX solution was added (30 nM final concentration), mixed five times and then incubated for 15 minutes at 30° C. 10 μL of MR121 substrate solution was added (1 μM final concentration), mixed 30 times and then incubated for 15 minutes at 30° C. Fluorescence was then measured every 2 minutes for 1 hour (Perkin Elmer plate: vision multimode reader); light intensity: 2.5%; exp. time: 1.4 sec, Filter: Fluo_630/690 nm) and IC$_{50}$ values were calculated from these readouts.

| Example | IC50 (μM) |
| --- | --- |
| 1 | 0.015 |
| 1.01 | 2.401 |
| 1.02 | 0.129 |
| 1.03 | 0.201 |
| 1.04 | 0.115 |
| 1.05 | 1.044 |
| 1.06 | 0.107 |
| 1.07 | 4.14 |
| 1.08 | 3.352 |
| 1.09 | 0.0505 |
| 1.10 | 3.699 |
| 1.11 | 0.155 |
| 1.12 | 0.035 |
| 1.13 | 5.426 |
| 1.14 | 0.0737 |
| 1.15 | 0.0645 |
| 1.16 | n.d. |
| 1.17 | 0.729 |
| 1.18 | 0.625 |
| 1.19 | 0.0395 |
| 1.20 | 0.12 |
| 1.21 | 0.821 |
| 1.22 | 0.015 |
| 1.23 | 0.001 |
| 1.24 | 0.012 |
| 1.25 | 0.074 |
| 1.26 | 0.008 |
| 1.27 | 0.041 |
| 1.28 | 0.11 |
| 2 | 0.026 |
| 2.1 | 0.038 |
| 2.2 | 0.0137 |
| 3 | 0.006 |
| 3.1 | 3.565 |
| 3.2 | 0.298 |
| 3.3 | 0.059 |
| 3.4 | 0.0195 |
| 3.5 | 0.02 |
| 3.6 | 0.067 |
| 4 | 0.546 |
| 5 | 0.007 |
| 5.1 | 0.061 |
| 5.2 | 0.0265 |
| 6 | 0.026 |
| 6.1 | 0.362 |
| 6.2 | 0.298 |
| 6.3 | 2.661 |
| 6.4 | 0.022 |
| 6.5 | 3.216 |
| 6.6 | 0.605 |
| 6.7 | 3.928 |
| 6.8 | 0.091 |
| 6.9 | 0.128 |
| 6.10 | 0.826 |
| 7 | 0.043 |
| 7.1 | 0.26 |
| 8 | 0.178 |
| 9 | 1.061 |
| 10 | 3.438 |
| 11 | 1.287 |
| 12 | 0.1305 |
| 12.01 | 0.15 |
| 12.02 | 0.044 |
| 12.03 | 0.6225 |
| 12.04 | 0.017 |
| 12.05 | 4.979 |
| 12.06 | 7.2435 |
| 12.07 | 0.3775 |
| 12.08 | 3.8335 |
| 12.09 | 1.6405 |
| 12.10 | 0.291 |
| 12.11 | 0.1685 |
| 12.12 | 0.3323 |
| 12.13 | 3.5195 |
| 12.14 | 0.2705 |
| 12.15 | 0.035 |
| 12.16 | 0.457 |
| 12.17 | 0.0203 |
| 12.18 | 0.0535 |

-continued

| Example | IC50 (μM) |
|---|---|
| 12.19 | 2.147 |
| 12.20 | 5.64 |
| 12.21 | 1.253 |
| 12.22 | 0.439 |
| 12.23 | 1.9113 |
| 12.24 | 0.229 |
| 12.25 | 0.092 |
| 12.26 | 0.053 |
| 12.27 | 0.14 |
| 12.28 | 0.138 |
| 12.29 | 0.0685 |
| 12.30 | 1.604 |
| 12.31 | 0.022 |
| 12.32 | 0.044 |
| 12.33 | 0.013 |
| 12.34 | 0.01 |
| 12.35 | 0.0045 |
| 12.36 | 0.001 |
| 12.37 | 0.001 |
| 12.38 | 0.0025 |
| 12.39 | 0.005 |
| 12.40 | 0.0025 |
| 12.41 | 0.002 |
| 12.42 | 0.001 |
| 12.43 | 0.001 |
| 12.44 | 0.008 |
| 12.45 | 0.039 |
| 13 | 0.003 |
| 13.01 | 0.001 |
| 14 | 0.023 |
| 14.01 | 0.0415 |
| 15A | 0.016 |
| 15B | 0.001 |
| 16A | 0.1 |
| 16B | 0.009 |

Compounds of formula (I) and their pharmaceutically acceptable salts or esters thereof as described herein have $IC_{50}$ values between 0.00001 μM and 1000 μM, particular compounds have $IC_{50}$ values between 0.0005 μM and 500 μM, further particular compounds have $IC_{50}$ values between 0.0005 μM and 50 μM, more particular compounds have $IC_{50}$ values between 0.0005 μM and 5 μM. These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parenterally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

The invention is illustrated hereinafter by Examples, which have no limiting character.

In case the preparative examples are obtained as a mixture of enantiomers, the pure enantiomers can be separated by methods described herein or by methods known to those skilled in the art, such as e.g. chiral chromatography or crystallization.

EXAMPLES

All examples and intermediates were prepared under argon atmosphere if not specified otherwise.

Abbreviations:

aq.=aqueous; CAS-RN=Chemical Abstracts Service Registry Number; MS=mass spectrum; sat.=saturated.

Example 1

3,5-Dichlorobenzyl 2-(1H-benzo[d][1,2,3]triazole-5-carbonyl)-2,7-diazaspiro[3.5]nonane-7-carboxylate

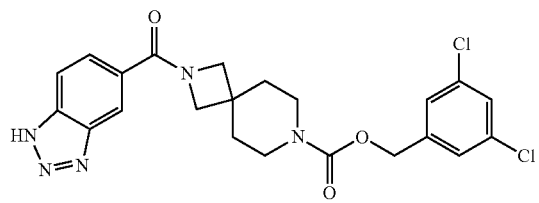 [SMILES: O=C(OCc1cc(Cl)cc(Cl)c1)N1CCC2(CC1)CN(C(=O)c1ccc3[nH]nnc3c1)C2]

To a solution of 3,5-dichlorobenzyl 2,7-diazaspiro[3.5]nonane-7-carboxylate hydrochloride (intermediate 1.18; 30 mg, 82 mmol), 4-methylmorpholine (41.5 mg, 410 μmol) and 1H-benzo[d][1,2,3]triazole-5-carboxylic acid (13 mg, 82 mmol) in N,N-dimethylformamide (1.5 ml) was added O-(7-azabenzotriazol-1-yl)-N,N,N',N'-tetramethyluronium hexafluoro-phosphate (46.8 mg, 123 mmol) at 0° C. The clear yellow solution was stirred at room temperature, then after 2 h the reaction mixture was partitioned between ethyl acetate and sat. aq. sodium hydrogencarbonate solution. The combined organic layer was washed with brine, dried over magnesium sulfate, filtered and evaporated. Chromatography (silica gel; gradient dichloromethane to dichloromethane/methanol/25% aq. ammonia solution 90:10:0.25) afforded the title compound (22 mg, 57%). Light yellow foam, MS: 474.1 (M+H)+.

The examples in Table 1 were prepared according to example 1, replacing 2,7-diazaspiro[3.5]nonane-7-carboxylate hydrochloride and 1H-benzo[d][1,2,3]triazole-5-carboxylic acid, respectively, by the corresponding amine reagent and carboxylic acid reagent described in Table 1.

TABLE 1

| No. | Systematic Name | Amine reagent | Carboxylic acid reagent | MS, m/e |
|---|---|---|---|---|
| 1.01 | benzyl 2-(1H-benzo[d][1,2,3]triazole-5-carbonyl)-2,7-diazaspiro[3.5]nonane-7-carboxylate | benzyl 2,7-diazaspiro[3.5]-nonane-7-carboxylate hydrochloride (CAS-RN 1227382-15-1) | 1H-benzo[d]-[1,2,3]triazole-5-carboxylic acid | 406.3 (M + H)+ |
| 1.02 | 4-chlorobenzyl 2-(1H-benzo[d][1,2,3]triazole-5-carbonyl)-2,7-diazaspiro[3.5]nonane-7-carboxylate | 4-chlorobenzyl 2,7-diazaspiro[3.5]-nonane-7-carboxylate hydrochloride (intermediate 1.17) | 1H-benzo[d]-[1,2,3]triazole-5-carboxylic acid | 440.3 (M + H)+ |
| 1.03 | 3-chlorobenzyl 2-(1H-benzo[d][1,2,3]triazole-5-carbonyl)-2,7-diazaspiro[3.5]nonane-7-carboxylate | 3-chlorobenzyl 2,7-diazaspiro[3.5]-nonane-7-carboxylate hydrochloride (intermediate 1.16) | 1H-benzo[d]-[1,2,3]triazole-5-carboxylic acid | 440.3 (M + H)+ |
| 1.04 | 1-(2-(1H-benzo[d][1,2,3]triazole-5-carbonyl)-2,7-diazaspiro[3.5]nonan-7-yl)-3-(3,5-dichlorophenyl)propan-1-one | 3-(3,5-dichlorophenyl)-1-(2,7-diazaspiro[3.5]nonan-7-yl)propan-1-one hydrochloride (intermediate 1.3) | 1H-benzo[d]-[1,2,3]triazole-5-carboxylic acid | 472.3 (M + H)+ |
| 1.05 | 1-(2-(4-amino-3-hydroxybenzoyl)-2,7-diazaspiro[3.5]nonan-7-yl)-3-(3,5-dichlorophenyl)propan-1-one | 3-(3,5-dichlorophenyl)-1-(2,7-diazaspiro[3.5]nonan-7-yl)propan-1-one hydrochloride (intermediate 1.3) | 4-amino-3-hydroxybenzoic acid | 462.2 (M + H)+ |

TABLE 1-continued

| No. | Systematic Name | Amine reagent | Carboxylic acid reagent | MS, m/e |
|---|---|---|---|---|
| 1.06 | 3,5-dichlorobenzyl 2-(4-amino-3-hydroxybenzoyl)-2,7-diazaspiro[3.5]nonane-7-carboxylate | 3,5-dichlorobenzyl 2,7-diazaspiro[3.5]-nonane-7-carboxylate hydrochloride (intermediate 1.18) | 4-amino-3-hydroxy-benzoic acid | 464.3 (M + H)+ |
| 1.07 | 6-[(1H-benzotriazole-5-carbonyl)-amino]-2-aza-spiro[3.3]heptane-2-carboxylic acid benzyl ester | benzyl 6-amino-2-azaspiro[3.3]heptane-2-carboxylate (intermediate 1.21) | 1H-benzo[d]-[1,2,3]triazole-5-carboxylic acid | 392.2 (M + H)+ |
| 1.08 | N-(2-(4-phenylbutanoyl)-2-azaspiro[3.3]heptan-6-yl)-1H-benzo[d][1,2,3]triazole-5-carboxamide | 1-(6-amino-2-azaspiro[3.3]heptan-2-yl)-4-phenylbutan-1-one (intermediate 1.7) | 1H-benzo[d]-[1,2,3]triazole-5-carboxylic acid | 404.2 (M + H)+ |
| 1.09 | 3-chloro-5-(methylsulfonyl)benzyl 2-(1H-benzo[d][1,2,3]triazole-5-carbonyl)-2,7-diazaspiro[3.5]nonane-7-carboxylate | 3-chloro-5-(methyl-sulfonyl)benzyl 2,7-diazaspiro[3.5]-nonane-7-carboxylate hydrochloride (intermediate 1.15) | 1H-benzo[d]-[1,2,3]triazole-5-carboxylic acid | 518.4 (M + H)+ |
| 1.10 | [2-(1H-benzotriazole-5-carbonyl)-2-aza-spiro[3.3]hept-6-yl]-carbamic acid benzyl ester | benzyl 2-azaspiro[3.3]heptan-6-ylcarbamate (intermediate 1.20) | 1H-benzo[d]-[1,2,3]triazole-5-carboxylic acid | 392.3 (M + H)+ |

TABLE 1-continued

| No. | Systematic Name | Amine reagent | Carboxylic acid reagent | MS, m/e |
|---|---|---|---|---|
| 1.11 | N-(2-(3-(3,5-dichlorophenyl)propanoyl)-2-azaspiro[3.3]heptan-6-yl)-1H-benzo[d][1,2,3]triazole-5-carboxamide | 1-(6-amino-2-azaspiro[3.3]heptan-2-yl)-3-(3,5-dichlorophenyl)propan-1-one (intermediate 1.6) | 1H-benzo[d]-[1,2,3]triazole-5-carboxylic acid | 458.4 (M + H)+ |
| 1.12 | [2-(1H-benzotriazole-5-carbonyl)-2-aza-spiro[3.3]hept-6-yl]-carbamic acid 3,5-dichloro-benzyl ester | 3,5-dichlorobenzyl 2-azaspiro[3.3]heptan-6-ylcarbamate (intermediate 1.12) | 1H-benzo[d]-[1,2,3]triazole-5-carboxylic acid | 460.1 (M + H)+ |
| 1.13 | 6-[(1H-benzotriazole-5-carbonyl)-amino]-2-aza-spiro[3.3]heptane-2-carboxylic acid 3,5-dichloro-benzyl ester | 3,5-dichlorobenzyl 6-amino-2-aza-spiro[3.3]heptane-2-carboxylate (intermediate 1.19) | 1H-benzo[d]-[1,2,3]triazole-5-carboxylic acid | 460.3 (M + H)+ |
| 1.14 | 3,5-dichlorobenzyl 2-(1H-benzo[d][1,2,3]triazole-5-carbonyl)-2,6-diazaspiro[3.4]octane-6-carboxylate | 3,5-dichlorobenzyl 2,6-diazaspiro[3.4]octane-6-carboxylate hydrochloride (intermediate 1.14) | 1H-benzo[d]-[1,2,3]triazole-5-carboxylic acid | 460.4 (M + H)+ |

TABLE 1-continued

| No. | Systematic Name | Amine reagent | Carboxylic acid reagent | MS, m/e |
|---|---|---|---|---|
| 1.15 | 3,5-dichlorobenzyl 7-(1H-benzo[d][1,2,3]triazole-5-carbonyl)-2,7-diazaspiro[3.5]nonane-2-carboxylate | 3,5-dichlorobenzyl 2,7-diazaspiro[3.5]-nonane-2-carboxylate hydrochloride (intermediate 1.13) | 1H-benzo[d]-[1,2,3]triazole-5-carboxylic acid | 474.4 (M + H)+ |
| 1.16 | 3,5-dichlorobenzyl 6-(4-amino-3-hydroxybenzamido)-2-azaspiro[3.3]heptane-2-carboxylate | 3,5-dichlorobenzyl 6-amino-2-aza-spiro[3.3]heptane-2-carboxylate (intermediate 1.19) | 4-amino-3-hydroxy-benzoic acid | 450.4 (M + H)+ |
| 1.17 | 3-chloro-5-(methylsulfonyl)benzyl 2-(4-sulfamoylbenzoyl)-2,7-diazaspiro[3.5]nonane-7-carboxylate | 3-chloro-5-(methyl-sulfonyl)benzyl 2,7-diazaspiro[3.5]-nonane-7-carboxylate hydrochloride (intermediate 1.15) | 4-sulfamoyl-benzoic acid | 556.4 (M + H)+ |
| 1.18 | 3-chloro-5-(methylsulfonyl)benzyl 2-(3-sulfamoylbenzoyl)-2,7-diazaspiro[3.5]nonane-7-carboxylate | 3-chloro-5-(methyl-sulfonyl)benzyl 2,7-diazaspiro[3.5]-nonane-7-carboxylate hydrochloride (intermediate 1.15) | 3-sulfamoyl-benzoic acid | 556.3 (M + H)+ |
| 1.19 | 3,5-dichlorobenzyl 8-(1H-benzo[d][1,2,3]triazole-5-carbonyl)-2,8-diazaspiro[4.5]decane-2-carboxylate | 3,5-dichlorobenzyl 2,8-diazaspiro[4.5]-decane-2-carboxylate hydrochloride (intermediate 1.10) | 1H-benzo[d]-[1,2,3]triazole-5-carboxylic acid | 488.4 (M + H)+ |

TABLE 1-continued

| No. | Systematic Name | Amine reagent | Carboxylic acid reagent | MS, m/e |
|---|---|---|---|---|
| 1.20 | 3-fluoro-5-(trifluoromethoxy)benzyl 7-(1H-benzo[d][1,2,3]triazole-5-carbonyl)-2,7-diazaspiro[4.5]decane-2-carboxylate | 3-fluoro-5-(trifluoromethoxy)benzyl 2,7-diazaspiro[4.5]decane-2-carboxylate 2,2,2-trifluoroacetate (intermediate 1.23) | 1H-benzo[d][1,2,3]triazole-5-carboxylic acid | 522.5 (M + H)+ |
| 1.21 | (1H-benzotriazol-5-yl)-{7-[2-(3-chloro-phenyl)-ethanesulfonyl]-2,7-diaza-spiro[3.5]non-2-yl}-methanone | 7-(3-chlorophenethylsulfonyl)-2,7-diazaspiro[3.5]nonane (intermediate 3) | 1H-benzo[d][1,2,3]triazole-5-carboxylic acid | 474.5 (M + H)+ |
| 1.22 | 4-(trifluoromethoxy)benzyl 2-(4-sulfamoylbenzoyl)-2,7-diazaspiro[3.5]nonane-7-carboxylate | 4-(trifluoromethoxy)benzyl 2,7-diaza-spiro[3.5]nonane-7-carboxylate (intermediate 1.27) | 4-sulfamoylbenzoic acid | 528.5 (M + H)+ |
| 1.23 | 2-fluoro-4-(trifluoromethoxy)benzyl 2-(4-sulfamoylbenzoyl)-2,7-diazaspiro[3.5]nonane-7-carboxylate | 2-fluoro-4-(trifluoromethoxy)benzyl 2,7-diaza-spiro[3.5]nonane-7-carboxylate (intermediate 1.28) | 4-sulfamoylbenzoic acid | 546.5 (M + H)+ |
| 1.24 | 1-(2-(1H-benzo[d][1,2,3]triazole-5-carbonyl)-2,7-diazaspiro[3.5]nonan-7-yl)-3-(4-(trifluoromethoxy)phenyl)propan-1-one | 1-(2,7-diazaspiro[3.5]nonan-7-yl)-3-(4-(trifluoromethoxy)phenyl)propan-1-one (intermediate 1.30) | 1H-benzo[d][1,2,3]triazole-5-carboxylic acid | 488.6 (M + H)+ |

TABLE 1-continued

| No. | Systematic Name | Amine reagent | Carboxylic acid reagent | MS, m/e |
|---|---|---|---|---|
| 1.25 | 3-isopropyl-4-(2-oxo-2-(2-(4,5,6,7-tetrahydro-1H-benzo[d][1,2,3]triazole-5-carbonyl)-2,7-diazaspiro[3.5]nonan-7-yl)ethoxy)benzonitrile | 3-isopropyl-4-(2-oxo-2-(2,7-diaza-spiro[3.5]nonan-7-yl)ethoxy)benzo-nitrile (intermediate 5) | 4,5,6,7-tetrahydro-1H-benzo[d]-[1,2,3]triazole-5-carboxylic acid (CAS-RN 33062-47-4) | 477.6 (M + H)+ |
| 1.26 | 1-(2-(1H-benzo[d][1,2,3]triazole-5-carbonyl)-2,7-diazaspiro[3.5]nonan-7-yl)-2-(4-chloro-2-isopropylphenoxy)ethanone | 2-(4-chloro-2-isopropylphenoxy)-1-(2,7-diaza-spiro[3.5]nonan-7-yl)ethanone (intermediate 5.1) | 1H-benzo[d]-[1,2,3]triazole-5-carboxylic acid | 482.4 (M + H)+ |
| 1.27 | 2-(4-chloro-2-isopropylphenoxy)-1-(2-(4,5,6,7-tetrahydro-1H-benzo[d][1,2,3]triazole-5-carbonyl)-2,7-diazaspiro[3.5]nonan-7-yl)ethanone | 2-(4-chloro-2-isopropylphenoxy)-1-(2,7-diaza-spiro[3.5]nonan-7-yl)ethanone (intermediate 5.1) | 4,5,6,7-tetrahydro-1H-benzo[d]-[1,2,3]triazole-5-carboxylic acid (CAS-RN 33062-47-4) | 486.6 (M + H)+ |
| 1.28 | 1-(2-(4,5,6,7-tetrahydro-1H-benzo[d][1,2,3]triazole-5-carbonyl)-2,7-diazaspiro[3.5]nonan-7-yl)-3-(4-(trifluoromethoxy)phenyl)propan-1-one | 1-(2,7-diaza-spiro[3.5]nonan-7-yl)-3-(4-(trifluoromethoxy)-phenyl)propan-1-one (intermediate 1.30) | 4,5,6,7-tetrahydro-1H-benzo[d]-[1,2,3]triazole-5-carboxylic acid (CAS-RN 33062-47-4) | 492.6 (M + H)+ |

Example 2

3,5-Dichlorobenzyl 2-(2-oxo-2,3-dihydro-benzo[d]oxazole-6-carbonyl)-2,6-diazaspiro[3.4]octane-6-carboxylate

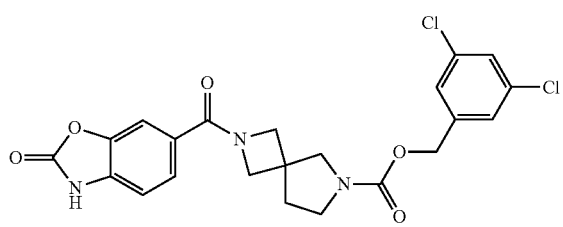 [SMILES: O=C(OCc1cc(Cl)cc(Cl)c1)N1CCC2(C1)CN(C(=O)c1ccc3[nH]c(=O)oc3c1)C2]

To a solution of 3,5-dichlorobenzyl 2,6-diazaspiro[3.4]octane-6-carboxylate hydrochloride (intermediate 1.14; 50 mg, 142 μmol, 4-methylmorpholine (72 mg, 711 μmol), and 4-amino-3-hydroxybenzoic acid (21.8 mg, 142 μmol) in N,N-dimethylformamide (1 ml) was added O-(7-azabenzotriazol-1-yl)-N,N,N',N'-tetramethyluronium hexafluorophosphate (64.9 mg, 171 μmol) at 0° C. After 2 h the ice bath was removed. Then after 4 h, 1,1'-carbonyldiimidazole (52.3 mg, 313 μmol) was added. After 16 h the reaction mixture was partitioned between ethyl acetate and 1 M aq. hydrochloric acid solution. The organic layer was washed with brine, dried over magnesium sulfate, filtered and evaporated in vacuo. The residue was azeotropically distilled with toluene and then chromatographed. Chromatography (silica gel; gradient dichloromethane to dichloromethane/methanol/25% aq. ammonia solution 90:10:0.25) afforded the title compound (35 mg, 52%). Light yellow gum, MS: 476.5 (M+H)$^+$.

The examples in Table 2 were prepared according to example 2, replacing 3,5-dichlorobenzyl 2,6-diazaspiro[3.4]octane-6-carboxylate hydrochloride by the corresponding amine reagent described in Table 2.

TABLE 2

| No. | Systematic Name | Amine reagent | MS, m/e |
|---|---|---|---|
| 2.1 | 3-chloro-5-(methylsulfonyl)benzyl 2-(2-oxo-2,3-dihydrobenzo[d]oxazole-6-carbonyl)-2,7-diazaspiro[3.5]nonane-7-carboxylate | 3-chloro-5-(methylsulfonyl)benzyl 2,7-diazaspiro[3.5]nonane-7-carboxylate hydrochloride (intermediate 1.15) | 534.4 (M + H)$^+$ |
| 2.2 | 7-(2-oxo-2,3-dihydro-benzooxazole-6-carbonyl)-2,7-diazaspiro[3.5]nonane-2-carboxylic acid 3,5-dichloro-benzyl ester | 3,5-dichlorobenzyl 2,7-diazaspiro[3.5]nonane-2-carboxylate hydrochloride (intermediate 1.13) | 490.5 (M + H)$^+$ |

Example 3

3,5-Dichlorobenzyl 2-(2-oxo-2,3-dihydro-benzo[d]oxazol-6-ylsulfonyl)-2,7-diazaspiro[3.5]nonane-7-carboxylate

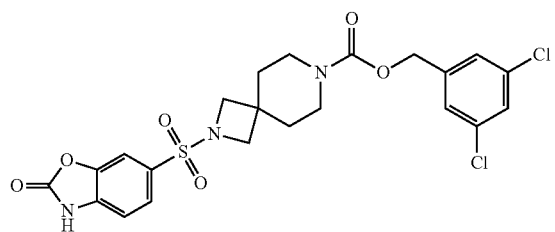 [SMILES: O=C(OCc1cc(Cl)cc(Cl)c1)N1CCC2(CC1)CN(S(=O)(=O)c1ccc3[nH]c(=O)oc3c1)C2]

To a suspension of 3,5-dichlorobenzyl 2,7-diazaspiro[3.5]nonane-7-carboxylate hydrochloride (intermediate 1.18; 30 mg, 82 μmol) and pyridine (32 mg, 410 μmol) in acetone (2 ml) was added 2-oxo-2,3-dihydrobenzo[d]oxazole-6-sulfonyl chloride (18 mg, 78 μmol) at room temperature. Then after 16 h the reaction mixture was partitioned between ethyl acetate and sat. aq. sodium hydrogencarbonate solution. The organic layer was washed with brine, dried over magnesium sulfate, filtered, and evaporated. Chromatography (silica gel; ethyl acetate) afforded the title compound (16 mg, 37%). White solid, MS: 524.1 (M−H)⁻.

The examples 3.1 to 3.6 in Table 3 were prepared according to example 3, replacing 3,5-dichlorobenzyl 2,7-diazaspiro[3.5]nonane-7-carboxylate hydrochloride and 2-oxo-2,3-dihydrobenzo[d]oxazole-6-sulfonyl chloride respectively by the corresponding amine reagent and the sulfonyl chloride described in Table 3.

TABLE 3

| No. | Systematic Name | Amine reagent | Sulfonyl chloride | MS, m/e |
|---|---|---|---|---|
| 3.1 | 2-oxo-2,3-dihydro-benzooxazole-6-sulfonic acid [2-(4-phenyl-butyryl)-2-aza-spiro[3.3]hept-6-yl]-amide | 1-(6-amino-2-azaspiro[3.3]heptan-2-yl)-4-phenylbutan-1-one (intermediate 1.7) | 2-oxo-2,3-dihydro-benzo[d]oxazole-6-sulfonyl chloride | 456.3 (M + H)⁺ |
| 3.2 | benzyl 6-(2-oxo-2,3-dihydrobenzo[d]oxazole-6-sulfonamido)-2-azaspiro[3.3]heptane-2-carboxylate | benzyl 6-amino-2-azaspiro[3.3]-heptane-2-carboxylate (CAS-RN 1211533-81-1) | 2-oxo-2,3-dihydro-benzo[d]oxazole-6-sulfonyl chloride | 442.1 (M − H)⁻ |
| 3.3 | 2-oxo-2,3-dihydro-benzooxazole-6-sulfonic acid {2-[3-(3,5-dichloro-phenyl)-propionyl]-2-aza-spiro[3.3]hept-6-yl}-amide | 1-(6-amino-2-azaspiro[3.3]heptan-2-yl)-3-(3,5-dichloro-phenyl)propan-1-one (intermediate 1.6) | 2-oxo-2,3-dihydro-benzo[d]oxazole-6-sulfonyl chloride | 510.4 (M + H)⁺ |

TABLE 3-continued

| No. | Systematic Name | Amine reagent | Sulfonyl chloride | MS, m/e |
|---|---|---|---|---|
| 3.4 | 3,5-dichlorobenzyl 6-(2-oxo-2,3-dihydrobenzo[d]oxazole-6-sulfonamido)-2-azaspiro[3.3]heptane-2-carboxylate | 3,5-dichlorobenzyl 6-amino-2-azaspiro[3.3]-heptane-2-carboxylate (intermediate 1.19) | 2-oxo-2,3-dihydro-benzo[d]oxazole-6-sulfonyl chloride | 510.4 (M − H)⁻ |
| 3.5 | [2-(2-oxo-2,3-dihydro-benzooxazole-6-sulfonyl)-2-aza-spiro[3.3]hept-6-yl]-carbamic acid 3,5-dichloro-benzyl ester | 3,5-dichlorobenzyl 2-azaspiro[3.3]heptan-6-ylcarbamate (intermediate 1.12) | 2-oxo-2,3-dihydro-benzo[d]oxazole-6-sulfonyl chloride | 512.2 (M + H)⁺ |
| 3.6 | 3-chloro-5-(methylsulfonyl)benzyl 2-(2-oxo-2,3-dihydrobenzo[d]thiazol-6-ylsulfonyl)-2,7-diazaspiro[3.5]nonane-7-carboxylate | 3-chloro-5-(methylsulfonyl)benzyl 2,7-diazaspiro[3.5]nonane-7-carboxylate hydrochloride (intermediate 1.15) | 2-oxo-2,3-dihydro-benzo[d]thiazole-6-sulfonyl chloride | 586.2 (M + H)⁺ |

Example 4

3,5-Dichlorobenzyl 2-((2-oxo-2,3-dihydro-benzo[d]oxazol-6-yl)methyl)-2,7-diaza-spiro[3.5]nonane-7-carboxylate

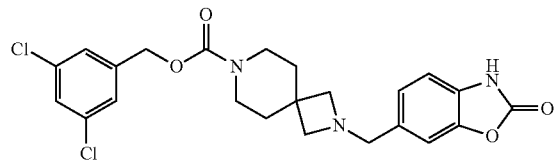 [SMILES: O=C(OCc1cc(Cl)cc(Cl)c1)N1CCC2(CC1)CN(Cc1ccc3[nH]c(=O)oc3c1)C2]

To a light yellow solution of 3,5-dichlorobenzyl 2,7-diazaspiro[3.5]nonane-7-carboxylate (intermediate 1.18; 44 mg, 121 μmol) and 2-oxo-2,3-dihydrobenzo[d]oxazole-6-carbaldehyde (CAS-RN 54903-15-0; 21 mg, 128 μmol) in tetrahydrofuran (1 ml) were added sodium triacetoxyborohydride (39 mg, 182 μmol) and acetic acid (11 mg, 182 μmol) at room temperature. Then after 16 h the reaction mixture was partitioned between ethyl acetate and sat. aq. sodium hydrogencarbonate solution. The organic layer was washed with brine, dried over magnesium sulfate, filtered, and evaporated. Chromatography (silica gel; gradient dichloromethane to dichloromethane/methanol/25% aq. ammonia solution 95:5:0.25) afforded the title compound (12 mg, 21%). White foam, MS: 476.2 (M+H)⁺.

Example 5

3,5-Dichlorobenzyl 2-(2-oxo-2,3-dihydrobenzo[d]oxazole-6-carbonyl)-2,7-diazaspiro[3.5]nonane-7-carboxylate

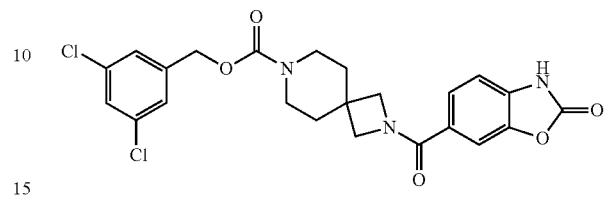

To a yellow solution of 3,5-dichlorobenzyl 2-(4-amino-3-hydroxybenzoyl)-2,7-diazaspiro[3.5]nonane-7-carboxylate (example 1.6; 50 mg, 108 μmol) in tetrahydrofuran (1 ml) was added dropwise at room temperature a solution of N,N'-carbonyldiimidazole (21.0 mg, 129 μmol) in tetrahydrofuran (0.5 ml). Then after 16 h the reaction mixture was partitioned between water and ethyl acetate. The organic layer was washed with brine, dried over magnesium sulfate, filtered, and evaporated. The residue was triturated in heptane/ethyl acetate 1:1 to produce the title compound (36 mg, 68%). Light yellow solid, MS: 490.2 (M+H)⁺.

The examples in Table 4 were prepared according to example 5, replacing 3,5-dichlorobenzyl 2-(4-amino-3-hydroxybenzoyl)-2,7-diazaspiro[3.5]nonane-7-carboxylate by the corresponding starting material described in Table 4.

TABLE 4

| No. | Systematic Name | Starting material | MS, m/e |
|---|---|---|---|
| 5.1 | 6-(7-(3-(3,5-dichlorophenyl)propanoyl)-2,7-diazaspiro[3.5]nonane-2-carbonyl)benzo[d]oxazol-2(3H)-one | 1-(2-(4-amino-3-hydroxybenzoyl)-2,7-diazaspiro[3.5]nonan-7-yl)-3-(3,5-dichlorophenyl)propan-1-one (example 1.5) | 488.2 (M + H)⁺ |
| 5.2 | 6-[(2-oxo-2,3-dihydro-benzooxazole-6-carbonyl)-amino]-2-azaspiro[3.3]heptane-2-carboxylic acid 3,5-dichloro-benzyl ester | 3,5-dichlorobenzyl 6-(4-amino-3-hydroxybenzamido)-2-azaspiro[3.3]heptane-2-carboxylate (example 1.16) | 476.4 (M + H)⁺ |

Example 6

(E)-1-(2-(1H-benzo[d][1,2,3]triazole-5-carbonyl)-2,7-diazaspiro[3.5]nonan-7-yl)-3-(3,5-dichlorophenyl)prop-2-en-1-one

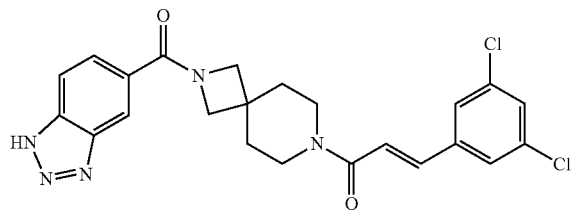 [SMILES: O=C(/C=C/c1cc(Cl)cc(Cl)c1)N1CCC2(CC1)CN(C(=O)c1ccc3[nH]nnc3c1)C2]

To a suspension of (1H-benzo[d][1,2,3]triazol-5-yl)(2,7-diazaspiro[3.5]nonan-2-yl)methanone hydrochloride (intermediate 1.2; 50 mg, 162 μmol), 4-methylmorpholine (82.2 mg, 812 μmol) and (E)-3-(3,5-dichlorophenyl)acrylic acid (35.3 mg, 162 μmol) in N,N-dimethylformamide (2 ml) was added O-(7-azabenzotriazol-1-yl)-N,N,N',N'-tetramethyluronium hexafluoro-phosphate (61.8 mg, 162 μmol) at 0° C. Then after 16 h at room temperature, the reaction mixture was partitioned between ethyl acetate and sat. aq. sodium hydrogencarbonate solution. The organic layer was washed with brine, dried over magnesium sulfate, filtered and evaporated. Chromatography (silica gel; gradient dichloromethane to dichloromethane/methanol/25% aq. ammonia solution 90:10:0.25) produced the title compound (72 mg, 94%). White foam, MS: 470.4 (M+H)$^+$.

The examples in Table 5 were prepared according to example 6, replacing (1H-benzo[d][1,2,3]triazol-5-yl)(2,7-diazaspiro[3.5]nonan-2-yl)methanone hydrochloride and (E)-3-(3,5-dichlorophenyl)acrylic acid respectively by the corresponding amine reagent and carboxylic acid reagent described in Table 5.

TABLE 5

| No. | Systematic Name | Amine reagent | Carboxylic acid reagent | MS, m/e |
|---|---|---|---|---|
| 6.1 | 6-(7-(3-(3,5-dichlorophenyl)propanoyl)-7-azaspiro[3.5]nonan-2-ylamino)benzo[d]oxazol-2(3H)-one | 6-(7-azaspiro[3.5]nonan-2-ylamino)-benzo[d]oxazol-2(3H)-one dihydrochloride (intermediate 1.11) | 3-(3,5-dichlorophenyl)-propanoic acid | 474.3 (M + H)$^+$ |
| 6.2 | 1-(2-(1H-benzo[d][1,2,3]triazole-5-carbonyl)-2,7-diazaspiro[3.5]nonan-7-yl)-2-(3,5-dichlorophenoxy)ethanone | (1H-benzo[d]-[1,2,3]triazol-5-yl)(2,7-diazaspiro[3.5]nonan-2-yl)methanone hydrochloride (intermediate 1.2) | 2-(3,5-dichlorophenoxy)-acetic acid | 474.4 (M + H)$^+$ |
| 6.3 | (2-(1H-benzo[d][1,2,3]triazole-5-carbonyl)-2,7-diazaspiro[3.5]nonan-7-yl)(3,5-dichlorophenyl)methanone | (1H-benzo[d]-[1,2,3]triazol-5-yl)(2,7-diaza-spiro[3.5]nonan-2-yl)methanone hydrochloride (intermediate 1.2) | 3,5-dichlorobenzoic acid | 444.4 (M + H)$^+$ |

TABLE 5-continued

| No. | Systematic Name | Amine reagent | Carboxylic acid reagent | MS, m/e |
|---|---|---|---|---|
| 6.4 | 6-{7-[(E)-3-(3,5-dichloro-phenyl)-acryloyl]-2,7-diaza-spiro[3.5]nonane-2-carbonyl}-3H-benzooxazol-2-one | 6-(2,7-diaza-spiro[3.5]nonane-2-carbonyl)-benzo[d]oxazol-2(3H)-one hydrochloride (intermediate 1.8) | (E)-3-(3,5-dichloro-phenyl)acrylic acid | 486.3 (M + H)+ |
| 6.5 | (2-(1H-benzo[d][1,2,3]triazole-5-carbonyl)-2,7-diazaspiro[3.5]nonan-7-yl)(trans-2-(3,5-difluorophenyl)cyclopropyl)methanone | (1H-benzo[d][1,2,3]triazol-5-yl)(2,7-diaza-spiro[3.5]nonan-2-yl)methanone hydrochloride (intermediate 1.2) | trans-2-(3,5-di-fluorophenyl)-cyclopropane-carboxylic acid (CAS-RN 705250-91-5) | 452.5 (M + H)+ |
| 6.6 | (7-(1H-benzo[d][1,2,3]triazole-5-carbonyl)-2,7-diazaspiro[4.4]nonan-2-yl)(5-chloro-1H-indol-2-yl)methanone | (1H-benzo[d][1,2,3]triazol-5-yl)(2,7-diaza-spiro[4.4]nonan-2-yl)methanone hydrochloride (intermediate 1.1) | 5-chloro-1H-indole-2-carboxylic acid | 449.5 (M + H)+ |
| 6.7 | (7-(1H-benzo[d][1,2,3]triazole-5-carbonyl)-2,7-diazaspiro[4.4]nonan-2-yl)(5-chlorobenzofuran-2-yl)methanone | (1H-benzo[d][1,2,3]triazol-5-yl)(2,7-diaza-spiro[4.4]nonan-2-yl)methanone hydrochloride (intermediate 1.1) | 5-chlorobenzo-furan-2-carboxylic acid | 450.5 (M + H)+ |

TABLE 5-continued

| No. | Systematic Name | Amine reagent | Carboxylic acid reagent | MS, m/e |
|---|---|---|---|---|
| 6.8 | (E)-N-((1H-1,2,3-triazol-5-yl)methyl)-7-(3-(4-(trifluoromethoxy)phenyl)acryloyl)-7-azaspiro[3.5]nonane-2-carboxamide | N-((1H-1,2,3-triazol-5-yl)methyl)-7-azaspiro[3.5]nonane-2-carboxamide 2,2,2-trifluoroacetate (intermediate 1.24) | (E)-3-(4-(trifluoromethoxy)phenyl)acrylic acid | 464.5 (M + H)+ |
| 6.9 | 1-(2-(1H-benzo[d][1,2,3]triazole-5-carbonyl)-2,7-diazaspiro[3.5]nonan-7-yl)-3-(4-chlorophenyl)prop-2-yn-1-one | (1H-benzo[d][1,2,3]triazol-5-yl)(2,7-diazaspiro[3.5]nonan-2-yl)methanone hydrochloride (intermediate 1.2) | 3-(4-chlorophenyl)-propiolic acid (CAS-RN 3240-10-6) | 434.4 (M + H)+ |
| 6.10 | 1-(2-(1H-benzo[d][1,2,3]triazole-5-carbonyl)-2,7-diazaspiro[3.5]nonan-7-yl)-3-(3-chlorophenyl)prop-2-yn-1-one | (1H-benzo[d][1,2,3]triazol-5-yl)(2,7-diazaspiro[3.5]nonan-2-yl)methanone hydrochloride (intermediate 1.2) | 3-(3-chlorophenyl)-propiolic acid (CAS-RN 7396-28-3) | 434.4 (M + H)+ |

Example 7

(1H-benzo[d][1,2,3]triazol-5-yl)(7-(5-(3,5-dichlorophenyl)-1,3,4-oxadiazol-2-yl)-2,7-diazaspiro[3.5]nonan-2-yl)methanone

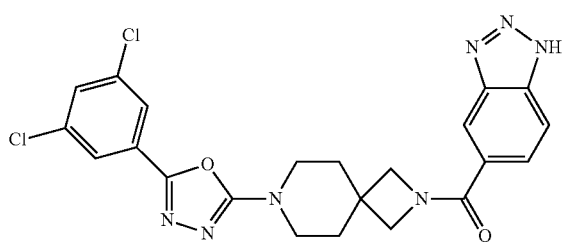 [SMILES: O=C(c1ccc2[nH]nnc2c1)N1CC2(CCN(c3nnc(-c4cc(Cl)cc(Cl)c4)o3)CC2)C1]

To a solution of 5-(3,5-dichlorophenyl)-1,3,4-oxadiazol-2(3H)-one (CAS-RN 129221-01-8; 50 mg, 216 mmol) and N,N-diisopropylethylamine (140 mg, 1.08 mmol) in N,N-dimethylformamide (2.8 ml) was added (1H-benzo[d][1,2,3]triazol-5-yl)(2,7-diazaspiro[3.5]nonan-2-yl)methanone hydrochloride (intermediate 1.2; 73.3 mg, 238 mmol) at room temperature. Then after 5 min benzotriazol-1-yl-oxy-tris-(dimethylamino)-phosphonium hexafluorophosphate (107 mg, 238 mmol) was added. The reaction mixture was heated at 50° C. for 16 h and was then partitioned between water and ethyl acetate. The organic layer was washed with brine, dried over magnesium sulfate, filtered and evaporated. The residue was triturated in ethyl acetate/methanol 19:1 to produce the title compound (33 mg, 32%). White solid, MS: 484.5 (M+H)+.

The example in Table 6 was prepared according to example 7, replacing (1H-benzo[d][1,2,3]triazol-5-yl)(2,7-diazaspiro[3.5]nonan-2-yl)methanone hydrochloride and 5-(3,5-dichlorophenyl)-1,3,4-oxadiazol-2(3H)-one respectively by the corresponding amine reagent and oxadiazolone reagent described in Table 6.

TABLE 6

| No. | Systematic Name | Amine reagent | Oxadiazolone reagent | MS, m/e |
|---|---|---|---|---|
| 7.1 | (1H-benzo[d][1,2,3]triazol-5-yl)(7-(5-(4-chlorophenyl)-1,3,4-oxadiazol-2-yl)-2,7-diazaspiro[3.5]nonan-2-yl)methanone | (1H-benzo[d]-[1,2,3]triazol-5-yl)(2,7-diazaspiro[3.5]nonan-2-yl)methanone hydrochloride (intermediate 1.2) | 5-(4-chlorophenyl)-1,3,4-oxadiazol-2(3H)-one (CAS-RN 1711-61-1) | 450.5 (M + H)+ |

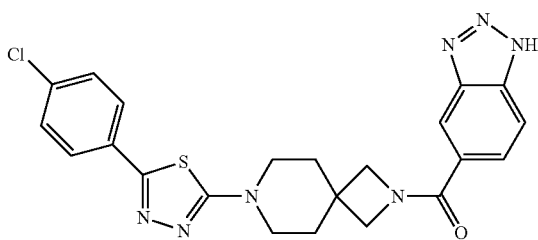 [SMILES: O=C(c1ccc2[nH]nnc2c1)N1CC2(CCN(c3nnc(-c4ccc(Cl)cc4)s3)CC2)C1]

Example 8

(1H-Benzo[d][1,2,3]triazol-5-yl)(7-(5-(4-chlorophenyl)-1,3,4-thiadiazol-2-yl)-2,7-diazaspiro[3.5]nonan-2-yl)methanone

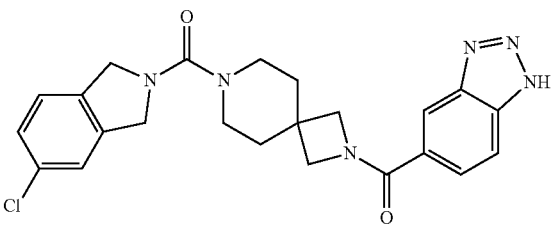

To a suspension of (1H-benzo[d][1,2,3]triazol-5-yl)(2,7-diazaspiro[3.5]nonan-2-yl)methanone hydrochloride (intermediate 1.2; 40 mg, 130 μmol) in toluene (3 ml) was added 1,8-diazabicyclo[5.4.0]undec-7-ene (79.1 mg, 520 μmol) and 2-bromo-5-(4-chlorophenyl)-1,3,4-thiadiazole (53.7 mg, 195 μmol). The reaction mixture was heated at reflux for 15 h and was then evaporated. After chromatography of the residue (silica gel; gradient dichloromethane to dichloromethane/methanol/25% aq. ammonia solution 90:10:0.25), the crude product was partitioned between ethyl acetate and 10% aq. citric acid solution. The organic layer was washed with sat. aq. sodium hydrogencarbonate solution and brine, dried over magnesium sulfate, filtered and evaporated to produce the title compound (27 mg, 45%). Light yellow foam, MS: 466.4 (M+H)+.

Example 9

2-(1H-Benzo[d][1,2,3]triazole-5-carbonyl)-N-(3,5-dichlorobenzyl)-2,7-diazaspiro[3.5]nonane-7-carboxamide

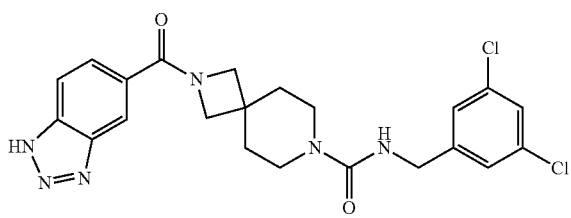 [SMILES: O=C(NCc1cc(Cl)cc(Cl)c1)N1CCC2(CC1)CN(C(=O)c1ccc3[nH]nnc3c1)C2]

To a solution of (3,5-dichlorophenyl)methanamine (27.1 mg, 146 mmol) in acetonitrile (2 ml) was added N,N'-carbonyldiimidazole (24.9 mg, 154 mmol) at room temperature, then after 2 h triethylamine (59.2 mg, 585 mmol) and (1H-benzo[d][1,2,3]triazol-5-yl)(2,7-diazaspiro[3.5]nonan-2-yl)methanone hydrochloride (intermediate 1.2; 45 mg, 146 mmol) were added. The light yellow suspension was heated at reflux for 30 min and was then partitioned between ethyl acetate and sat. aq. sodium hydrogencarbonate solution. The organic layer was washed with brine, dried over magnesium sulfate, filtered, and evaporated. Chromatography (silica gel; gradient dichloromethane/methanol/25% aq. ammonia solution 95:5:0.25 to 90:10:0.25) afforded the title compound (37 mg, 53%). White foam, MS: 473.1 (M+H)+.

Example 10

(2-(1H-Benzo[d][1,2,3]-triazole-5-carbonyl)-2,7-diazaspiro[3.5]nonan-7-yl)(5-chloroisoindolin-2-yl)methanone To a suspension of (1H-benzo[d][1,2,3]triazol-5-yl)(2,7-diazaspiro[3.5]nonan-2-yl)methanone hydrochloride (intermediate 1.2; 40 mg, 130 mmol) and N,N-diisopropylethylamine (50.4 mg, 390 mmol) in dichloromethane (4 ml) was added 5-chloroisoindoline-2-carbonyl chloride (CAS-RN 681483-91-0; 33.7 mg, 156 mmol) at 0° C. After 1 h the ice-bath was removed and the light brown suspension was stirred at room temperature. Then after 16 h the reaction mixture was partitioned between ethyl acetate and water. The organic layer was washed with brine, dried over magnesium sulfate, filtered and evaporated. Chromatography (silica gel; gradient dichloromethane/methanol/25% aq. ammonia solution 95:5:0.25 to 90:10:0.25) afforded the title compound (37 mg, 63%). Light yellow foam, MS: 451.4 (M+H)+.

Example 11

Benzyl 2-(2-oxo-2,3-dihydrobenzo[d]oxazol-6-ylamino)-7-azaspiro[3.5]nonane-7-carboxylate

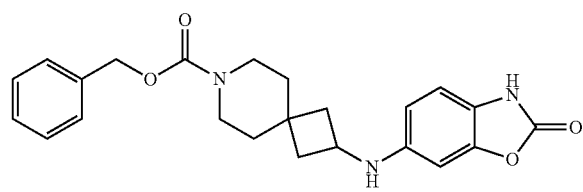 [SMILES: O=C(OCc1ccccc1)N1CCC2(CC1)CC(Nc1ccc3[nH]c(=O)oc3c1)C2]

To a colorless, clear solution of 6-(7-azaspiro[3.5]nonan-2-ylamino)benzo[d]oxazol-2(3H)-one dihydrochloride (intermediate 1.11; 60 mg, 173 mmol) and sodium hydrogencarbonate (87.3 mg, 1.04 mmol, Eq: 6) in acetone (1 ml) and water (1.00 ml) was added benzyl chloroformate (31.1 mg, 173 mmol) at room temperature. Then after 16 h the reaction mixture was partitioned between sat. aq. sodium hydrogencarbonate solution and ethyl acetate. The organic layer was washed with brine, dried over magnesium sulfate, filtered, and evaporated. Chromatography (silica gel; gradient dichloromethane/methanol/25% aq. ammonia solution 95:5:0.25 to 90:10:0.25) afforded the title compound (7 mg, 10%). White foam, MS: 408.3 (M+H)+.

Example 12

4-Chloro-3-fluorobenzyl 2-(1H-benzo[d][1,2,3]triazole-5-carbonyl)-2,7-diazaspiro[3.5]nonane-7-carboxylate

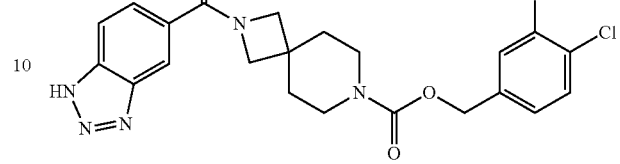

To a solution of (4-chloro-3-fluorophenyl)methanol (18.3 mg, 114 mmol) in acetonitrile (2 ml) was added N,N'-carbonyldiimidazole (19.4 mg, 119 mmol) at room temperature. Then after 2 h triethylamine (46.0 mg, 455 mmol) and (1H-benzo[d][1,2,3]triazol-5-yl)(2,7-diazaspiro[3.5]nonan-2-yl)methanone hydrochloride (intermediate 1.2; 35 mg, 114 mmol) were added. The reaction mixture was heated at reflux for 16 h and was then partitioned between ethyl acetate and sat. aq. sodium hydrogencarbonate solution. The organic layer was washed with brine, dried over magnesium sulfate, filtered, and evaporated. Chromatography (silica gel; gradient dichloromethane to dichloromethane/methanol/25% aq. ammonia solution 90:10:0.25) afforded the title compound (40 mg, 77%). White foam, MS:458.5 (M+H)+.

The examples in Table 7 were prepared according to example 12, replacing (1H-benzo[d][1,2,3]triazol-5-yl)(2,7-diazaspiro[3.5]nonan-2-yl)methanone hydrochloride and (4-chloro-3-fluorophenyl)methanol respectively by the corresponding amine reagent and benzyl alcohol reagent described in Table 7.

TABLE 7

| No. | Systematic Name | Amine reagent | Benzyl alcohol reagent | MS, m/e |
|---|---|---|---|---|
| 12.01 | (2,6-dichloropyridin-4-yl)methyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diazaspiro[3.5]nonan-2-yl)methanone hydrochloride (intermediate 1.2) | (2,6-dichloropyridin-4-yl)methanol | 475.4 (M + H)+ |
| 12.02 | 3,4-dichlorobenzyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diazaspiro[3.5]nonan-2-yl)methanone hydrochloride (intermediate 1.2) | (3,4-dichlorophenyl)-methanol | 474.4 (M + H)+ |

TABLE 7-continued

| No. | Systematic Name | Amine reagent | Benzyl alcohol reagent | MS, m/e |
|---|---|---|---|---|
| 12.03 | (5,6-dichloropyridin-3-yl)methyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diazaspiro[3.5]nonan-2-yl)methanone hydrochloride (intermediate 1.2) | (5,6-dichloro-pyridin-3-yl)methanol | 475.4 (M + H)+ |
| 12.04 | 2,4-dichlorobenzyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diazaspiro[3.5]nonan-2-yl)methanone hydrochloride (intermediate 1.2) | (2,4-dichloro-phenyl)-methanol | 474.4 (M + H)+ |
| 12.05 | (6-chloropyridin-3-yl)methyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diaza-spiro[3.5]nonan-2-yl)methanone hydrochloride (intermediate 1.2) | (6-chloro-pyridin-3-yl)methanol | 441.5 (M + H)+ |
| 12.06 | 4-chloro-3-(methylsulfonyl)benzyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diaza-spiro[3.5]nonan-2-yl)methanone hydrochloride (intermediate 1.2) | (4-chloro-3-(methyl-sulfonyl)phe-nyl)methanol (intermediate 2) | 518.4 (M + H)+ |

TABLE 7-continued

| No. | Systematic Name | Amine reagent | Benzyl alcohol reagent | MS, m/e |
|---|---|---|---|---|
| 12.07 | 1-(3,5-dichlorophenyl)ethyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diaza-spiro[3.5]nonan-2-yl)methanone hydrochloride (intermediate 1.2) | 1-(3,5-dichloro-phenyl)ethanol | 488.4 (M + H)+ |
| 12.08 | (5-chloropyridin-3-yl)methyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diazaspiro[3.5]nonan-2-yl)methanone hydrochloride (intermediate 1.2) | (5-chloro-pyridin-3-yl)methanol | 441.5 (M + H)+ |
| 12.09 | (5-bromopyridin-3-yl)methyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diazaspiro[3.5]nonan-2-yl)methanone hydrochloride (intermediate 1.2) | (5-bromopyridin-3-yl)methanol | 485.4 (M + H)+ |
| 12.10 | (4,6-dichloropyridin-2-yl)methyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diazaspiro[3.5]nonan-2-yl)methanone hydrochloride (intermediate 1.2) | (4,6-dichloro-pyridin-2-yl)methanol (CAS-RN 856163-79-6) | 475.4 (M + H)+ |

TABLE 7-continued

| No. | Systematic Name | Amine reagent | Benzyl alcohol reagent | MS, m/e |
|---|---|---|---|---|
| 12.11 | 3-chloro-4-fluorobenzyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diazaspiro[3.5]nonan-2-yl)methanone hydrochloride (intermediate 1.2) | (3-chloro-4-fluorophenyl)-methanol | 458.4 (M + H)+ |
| 12.12 | (5-chlorothiophen-3-yl)methyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diazaspiro[3.5]nonan-2-yl)methanone hydrochloride (intermediate 1.2) | (5-chlorothio-phen-3-yl)methanol | 446.4 (M + H)+ |
| 12.13 | thiophen-3-ylmethyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diaza-spiro[3.5]nonan-2-yl)methanone hydrochloride (intermediate 1.2) | thiophen-3-ylmethanol | 412.5 (M + H)+ |
| 12.14 | (5-bromothiophen-3-yl)methyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diazaspiro[3.5]nonan-2-yl)methanone hydrochloride (intermediate 1.2) | (5-bromothio-phen-3-yl)methanol | 490.4 (M + H)+ |

TABLE 7-continued

| No. | Systematic Name | Amine reagent | Benzyl alcohol reagent | MS, m/e |
|---|---|---|---|---|
| 12.15 | 4-(trifluoromethyl)benzyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diazaspiro[3.5]nonan-2-yl)methanone hydrochloride (intermediate 1.2) | (4-(trifluoromethyl)-phenyl)-methanol | 474.5 (M + H)+ |
| 12.16 | 3,5-dichlorobenzyl 7-(1H-benzo[d][1,2,3]triazole-5-carbonyl)-2,7-diazaspiro[4.4]nonane-2-carboxylate | (1H-benzo[d]-[1,2,3]triazol-5-yl)(2,7-diazaspiro[4.4]nonan-2-yl)methanone hydrochloride (intermediate 1.1) | (3,5-dichloro-phenyl)-methanol | 474.4 (M + H)+ |
| 12.17 | 2,4,6-trichlorobenzyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diazaspiro[3.5]nonan-2-yl)methanone hydrochloride (intermediate 1.2) | (2,4,6-trichloro-phenyl)-methanol | 506.4 (M − H)− |
| 12.18 | 6-[(1H-benzotriazole-5-carbonyl)-amino]-2-aza-spiro[3.3]heptane-2-carboxylic acid 3-chloro-5-trifluoromethoxy-benzyl ester | N-(2-azaspiro[3.3]-heptan-6-yl)-1H-benzo[d][1,2,3]tri-azole-5-carboxamide 2,2,2-trifluoroacetate (intermediate 1.5) | (3-chloro-5-(trifluoro-methoxy)-phenyl)-methanol | 508.6 (M − H)− |

TABLE 7-continued

| No. | Systematic Name | Amine reagent | Benzyl alcohol reagent | MS, m/e |
|---|---|---|---|---|
| 12.19 | 6-[(1H-benzotriazole-5-carbonyl)-amino]-2-aza-spiro[3.3]heptane-2-carboxylic acid 3-trifluoromethyl-benzyl ester | N-(2-azaspiro[3.3]heptan-6-yl)-1H-benzo[d][1,2,3]triazole-5-carboxamide 2,2,2-trifluoroacetate (intermediate 1.5) | (3-(trifluoromethyl)-phenyl)-methanol | 460.5 (M + H)+ |
| 12.20 | 6-[(1H-benzotriazole-5-carbonyl)-amino]-2-aza-spiro[3.3]heptane-2-carboxylic acid 3-chloro-5-cyano-benzyl ester | N-(2-azaspiro[3.3]heptan-6-yl)-1H-benzo[d][1,2,3]triazole-5-carboxamide 2,2,2-trifluoroacetate (intermediate 1.5) | 3-chloro-5-(hydroxymethyl)benzonitrile (CAS-RN 1021871-35-1) | 451.4 (M + H)+ |
| 12.21 | 6-[(1H-benzotriazole-5-carbonyl)-amino]-2-aza-spiro[3.3]heptane-2-carboxylic acid 3-chloro-4-fluoro-benzyl ester | N-(2-azaspiro[3.3]heptan-6-yl)-1H-benzo[d][1,2,3]triazole-5-carboxamide 2,2,2-trifluoroacetate (intermediate 1.5) | (3-chloro-4-fluorophenyl)-methanol | 444.4 (M + H)+ |

TABLE 7-continued

| No. | Systematic Name | Amine reagent | Benzyl alcohol reagent | MS, m/e |
|---|---|---|---|---|
| 12.22 | 4-(trifluoromethyl)benzyl 2-(2-oxo-2,3-dihydrobenzo[d]oxazole-6-carbonyl)-2,7-diazaspiro[3.5]nonane-7-carboxylate | 6-(2,7-diazaspiro[3.5]nonane-2-carbonyl)-benzo[d]oxazol-2(3H)-one hydrochloride (intermediate 1.8) | (4-(trifluoro-methyl)-phenyl)-methanol | 490.5 (M + H)+ |
| 12.23 | 6-[(1H-benzotriazole-5-carbonyl)-amino]-2-aza-spiro[3.3]heptane-2-carboxylic acid 3-fluoro-5-trifluoromethyl-benzyl ester | N-(2-azaspiro[3.3]-heptan-6-yl)-1H-benzo[d][1,2,3]tri-azole-5-carboxamide 2,2,2-trifluoroacetate (intermediate 1.5) | (3-fluoro-5-(trifluoro-methyl)-phenyl)-methanol | 478.4 (M + H)+ |
| 12.24 | 6-[(1H-benzotriazole-5-carbonyl)-amino]-2-aza-spiro[3.3]heptane-2-carboxylic acid 3-chloro-4-methyl-benzyl ester | N-(2-azaspiro[3.3]-heptan-6-yl)-1H-benzo[d][1,2,3]tri-azole-5-carboxamide 2,2,2-trifluoroacetate (intermediate 1.5) | (3-chloro-4-methyl-phenyl)-methanol | 440.4 (M + H)+ |

TABLE 7-continued

| No. | Systematic Name | Amine reagent | Benzyl alcohol reagent | MS, m/e |
|---|---|---|---|---|
| 12.25 | 3-(methylsulfonyl)-5-(trifluoromethyl)benzyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diaza-spiro[3.5]nonan-2-yl)methanone hydrochloride (intermediate 1.2) | (3-(methyl-sulfonyl)-5-(tri-fluoromethyl)-phenyl)-methanol (CAS-RN 1003843-94-4) | 552.4 (M + H)+ |
| 12.26 | 3-(methylsulfonyl)-5-(trifluoromethyl)benzyl 2-(2-oxo-2,3-dihydrobenzo[d]oxazole-6-carbonyl)-2,7-diazaspiro[3.5]nonane-7-carboxylate | 6-(2,7-diazaspiro[3.5]-nonane-2-carbonyl)-benzo[d]oxazol-2(3H)-one hydrochloride (intermediate 1.8) | (3-(methyl-sulfonyl)-5-(trifluoro-methyl)-phenyl)-methanol (CAS-RN 1003843-94-4) | 568.4 (M + H)+ |
| 12.27 | 4-chloro-2-(methylsulfonyl)benzyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diaza-spiro[3.5]nonan-2-yl)methanone hydrochloride (intermediate 1.2) | (4-chloro-2-(methyl-sulfonyl)-phenyl)-methanol (CAS-RN 773873-25-9) | 518.3 (M + H)+ |
| 12.28 | 2-chloro-4-(methylsulfonyl)benzyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diaza-spiro[3.5]nonan-2-yl)methanone hydrochloride (intermediate 1.2) | (2-chloro-4-(methyl-sulfonyl)-phenyl)-methanol (CAS-RN 181300-40-3) | 518.4 (M + H)+ |

TABLE 7-continued

| No. | Systematic Name | Amine reagent | Benzyl alcohol reagent | MS, m/e |
|---|---|---|---|---|
| 12.29 | 3,5-dichlorobenzyl 6-(1H-benzo[d][1,2,3]triazol-5-ylcarbamoyl)spiro[3.3]heptan-2-ylcarbamate | 6-amino-N-(1H-benzo[d][1,2,3]triazol-5-yl)spiro[3.3]heptane-2-carboxamide 2,2,2-trifluoroacetate (intermediate 1.9) | (3,5-dichlorophenyl)-methanol | 474.4 (M + H)+ |
| 12.30 | 3-fluoro-5-(trifluoromethoxy)benzyl 2-(1H-benzo[d][1,2,3]triazole-5-carbonyl)-2,7-diazaspiro[4.5]decane-7-carboxylate | (1H-benzo[d]-[1,2,3]triazol-5-yl)(2,7-diazaspiro[4.5]decan-2-yl)methanone 2,2,2-trifluoroacetate (intermediate 1.4) | (3-fluoro-5-(trifluoromethoxy)-phenyl)-methanol | 522.5 (M + H)+ |
| 12.31 | 3-chloro-5-(methylsulfonyl)benzyl 2-(2-oxo-2,3-dihydrobenzo[d]oxazol-6-ylsulfonyl)-2,7-diazaspiro[3.5]nonane-7-carboxylate | 6-(2,7-diazaspiro[3.5]nonan-2-ylsulfonyl)-benzo[d]oxazol-2(3H)-one hydrochloride (intermediate 1.22) | (3-chloro-5-(methylsulfonyl)-phenyl)-methanol (intermediate 2.1) | 568.3 (M − H)− |
| 12.32 | 2-[(3H-[1,2,3]triazol-4-ylmethyl)-carbamoyl]-7-aza-spiro[3.5]nonane-7-carboxylic acid 3,5-dichloro-benzyl ester | N-((1H-1,2,3-triazol-5-yl)methyl)-7-azaspiro[3.5]nonane-2-carboxamide 2,2,2-trifluoroacetate (intermediate 1.24) | (3,5-dichlorophenyl)-methanol | 452.5 (M + H)+ |

TABLE 7-continued

| No. | Systematic Name | Amine reagent | Benzyl alcohol reagent | MS, m/e |
|---|---|---|---|---|
| 12.33 | 3-fluoro-4-(trifluoromethoxy)benzyl 7-(4,5,6,7-tetrahydro-1H-benzo[d]-[1,2,3]triazole-5-carbonyl)-2,7-diazaspiro[3.5]nonane-2-carboxylate | 2,7-diaza-spiro[3.5]nonan-7-yl(4,5,6,7-tetrahydro-1H-benzo[d]-[1,2,3]triazol-5-yl)methanone 2,2,2-trifluoroacetate (intermediate 1.26) | (3-fluoro-4-(trifluoro-methoxy)-phenyl)-methanol (CAS-RN 886498-99-3) | 512.5 (M + H)+ |
| 12.34 | 4-(trifluoromethoxy)benzyl 7-(4,5,6,7-tetrahydro-1H-benzo[d]-[1,2,3]triazole-5-carbonyl)-2,7-diazaspiro[3.5]nonane-2-carboxylate | 2,7-diaza-spiro[3.5]nonan-7-yl(4,5,6,7-tetrahydro-1H-benzo[d]-[1,2,3]triazol-5-yl)methanone 2,2,2-trifluoroacetate (intermediate 1.26) | (4-(trifluoro-methoxy)-phenyl)-methanol | 494.5 (M + H)+ |
| 12.35 | [4-(trifluoromethyl)phenyl]methyl 2-(3a,4,5,6,7,7a-hexahydro-1H-benzotriazole-5-carbonyl)-2,7-diazaspiro[3.5]nonane-7-carboxylate | 2,7-diaza-spiro[3.5]nonan-2-yl(4,5,6,7-tetrahydro-1H-benzo[d]-[1,2,3]triazol-5-yl)methanone hydrochloride (intermediate 1.29) | (4-(trifluoro-methyl)-phenyl)-methanol | 478.6 (M + H)+ |
| 12.36 | [2-fluoro-4-(trifluoromethyl)phenyl]methyl 2-(4,5,6,7-tetrahydro-1H-benzotriazole-5-carbonyl)-2,7-diazaspiro[3.5]nonane-7-carboxylate | 2,7-diaza-spiro[3.5]nonan-2-yl(4,5,6,7-tetrahydro-1H-benzo[d]-[1,2,3]triazol-5-yl)methanone hydrochloride (intermediate 1.29) | (2-fluoro-4-(trifluoro-methyl)-phenyl)-methanol (CAS-RN 197239-49-9) | 496.2 (M + H)+ |

TABLE 7-continued

| No. | Systematic Name | Amine reagent | Benzyl alcohol reagent | MS, m/e |
|---|---|---|---|---|
| 12.37 | [2-methyl-4-(trifluoromethoxy)-phenyl]methyl 2-(4,5,6,7-tetrahydro-1H-benzotriazole-5-carbonyl)-2,7-diazaspiro[3.5]nonane-7-carboxylate | 2,7-diaza-spiro[3.5]nonan-2-yl(4,5,6,7-tetrahydro-1H-benzo[d]-[1,2,3]triazol-5-yl)methanone hydrochloride (intermediate 1.29) | (2-methyl-4-(trifluoro-methoxy)-phenyl)-methanol (CAS-RN 261951-94-4) | 508.2 (M + H)+ |
| 12.38 | 2-fluoro-4-(2,2,2-trifluoroethoxy)-benzyl 2-(4,5,6,7-tetrahydro-1H-benzo[d][1,2,3]triazole-6-carbonyl)-2,7-diazaspiro[3.5]nonane-7-carboxylate | 2,7-diaza-spiro[3.5]nonan-2-yl(4,5,6,7-tetrahydro-1H-benzo[d]-[1,2,3]triazol-5-yl)methanone hydrochloride (intermediate 1.29) | (2-fluoro-4-(2,2,2-trifluoro-ethoxy)-phenyl)-methanol (CAS-RN 1240257-07-1 | 526.8 (M + H)+ |
| 12.39 | 4-(2,2,2-trifluoroethoxy)benzyl 2-(4,5,6,7-tetrahydro-1H-benzo[d][1,2,3]triazole-6-carbonyl)-2,7-diazaspiro[3.5]nonane-7-carboxylate | 2,7-diaza-spiro[3.5]nonan-2-yl(4,5,6,7-tetrahydro-1H-benzo[d]-[1,2,3]triazol-5-yl)methanone hydrochloride (intermediate 1.29) | (4-(2,2,2-trifluoro-ethoxy)-phenyl)-methanol (CAS-RN 1020949-12-5) | 508.6 (M + H)+ |
| 12.40 | 3-fluoro-4-(2,2,2-trifluoroethoxy)-benzyl 2-(4,5,6,7-tetrahydro-1H-benzo[d][1,2,3]triazole-6-carbonyl)-2,7-diazaspiro[3.5]nonane-7-carboxylate | 2,7-diaza-spiro[3.5]nonan-2-yl(4,5,6,7-tetrahydro-1H-benzo[d]-[1,2,3]triazol-5-yl)methanone hydrochloride (intermediate 1.29) | (3-fluoro-4-(2,2,2-trifluoro-ethoxy)-phenyl)-methanol (CAS-RN 1039931-47-9) | 526.6 (M + H)+ |

TABLE 7-continued

| No. | Systematic Name | Amine reagent | Benzyl alcohol reagent | MS, m/e |
|---|---|---|---|---|
| 12.41 | 2-fluoro-4-(trifluoromethoxy)benzyl 7-(4,5,6,7-tetrahydro-1H-benzo[d]-[1,2,3]triazole-5-carbonyl)-2,7-diazaspiro[3.5]nonane-2-carboxylate | 2,7-diaza-spiro[3.5]nonan-7-yl(4,5,6,7-tetrahydro-1H-benzo[d]-[1,2,3]triazol-5-yl)methanone 2,2,2-trifluoroacetate (intermediate 1.26) | (2-fluoro-4-(trifluoro-methoxy)-phenyl)-methanol (CAS-RN 1240257-07-1) | 512.5 (M + H)+ |
| 12.42 | 2-fluoro-4-(trifluoromethoxy)benzyl 2-(4,5,6,7-tetrahydro-1H-benzo[d]-[1,2,3]triazole-5-carbonyl)-2,7-diazaspiro[3.5]nonane-7-carboxylate | 2,7-diaza-spiro[3.5]nonan-2-yl(4,5,6,7-tetrahydro-1H-benzo[d]-[1,2,3]triazol-5-yl)methanone hydrochloride (intermediate 1.29) | (2-fluoro-4-(trifluoro-methoxy)-phenyl)-methanol (CAS-RN 1240257-07-1) | 512.6 (M + H)+ |
| 12.43 | 4-(trifluoromethoxy)benzyl 2-(4,5,6,7-tetrahydro-1H-benzo[d]-[1,2,3]triazole-5-carbonyl)-2,7-diazaspiro[3.5]nonane-7-carboxylate | 2,7-diaza-spiro[3.5]nonan-2-yl(4,5,6,7-tetrahydro-1H-benzo[d]-[1,2,3]triazol-5-yl)methanone hydrochloride (intermediate 1.29) | (4-(trifluoro-methoxy)-phenyl)-methanol | 494.5 (M + H)+ |
| 12.44 | 3-chloro-5-(trifluoromethyl)benzyl 2-(1H-benzo[d][1,2,3]triazole-5-carbonyl)-2,7-diazaspiro[3.5]nonane-7-carboxylate | (1H-benzo[d]-[1,2,3]triazol-5-yl)(2,7-diaza-spiro[3.5]nonan-2-yl)methanone hydrochloride (intermediate 1.2) | (3-chloro-5-(trifluoro-methyl)-phenyl)-methanol | 508.5 (M + H)+ |

TABLE 7-continued

| No. | Systematic Name | Amine reagent | Benzyl alcohol reagent | MS, m/e |
|---|---|---|---|---|
| 12.45 | 3-(methylsulfonyl)-5-(trifluoro-methyl)benzyl 2-(2-oxo-2,3-dihydro-benzo[d]oxazol-6-ylsulfonyl)-2,7-diazaspiro[3.5]nonane-7-carboxylate | 6-(2,7-diaza-spiro[3.5]nonan-2-ylsulfonyl)-benzo[d]oxazol-2(3H)-one hydrochloride (intermediate 1.22) | (3-(methyl-sulfonyl)-5-(trifluoro-methyl)-phenyl)-methanol (CAS-RN 1003843-94-4) | 602.4 (M − H)− |

Example 13

4-(Trifluoromethoxy)benzyl 2-(4,5,6,7-tetrahydro-1H-[1,2,3]triazolo[4,5-c]pyridine-5-carbonyl)-2,7-diazaspiro[3.5]nonane-7-carboxylate

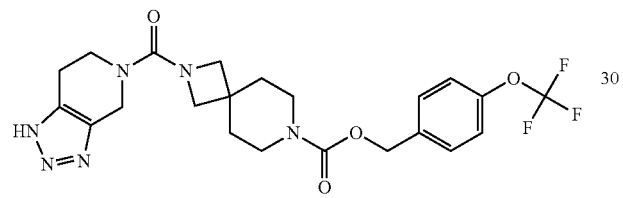

Sodium hydride dispersion (60% in mineral oil, 10.2 mg, 254 mmol) and sodium iodide (6.35 mg, 42.4 mmol) were added at room temperature to a solution of 4-(trifluoromethoxy)benzyl 4-(chloromethyl)-4-((4,5,6,7-tetrahydro-1H-[1,2,3]triazolo[4,5-c]pyridine-5-carboxamido)methyl)-piperidine-1-carboxylate (intermediate 3; 45 mg, 85 mmol) in N,N-dimethylformamide (2 mL). After 18 h the reaction mixture was partitioned between water and ethyl acetate, the organic layer was washed with brine, dried over sodium sulfate, filtered, and evaporated. The residue was purified by chromatography (silica gel; heptane-ethyl acetate gradient, followed by dichloromethane/methanol 19:1) to afford the title compound (13 mg, 30%). White foam, MS: 495.5 (M+H)+.

Example 13.1

2-Fluoro-4-(trifluoromethoxy)benzyl 2-(4,5,6,7-tetrahydro-1H-1,2,31-triazolo[4,5-c]pyridine-5-carbonyl)-2,7-diazaspiro[3.5]nonane-7-carboxylate

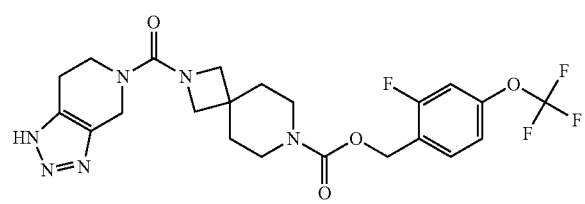

The title compound was produced in analogy to example 13 from 2-fluoro-4-(trifluoromethoxy)benzyl 4-(chloromethyl)-4-((4,5,6,7-tetrahydro-1H-[1,2,3]triazolo[4,5-c]pyridine-5-carboxamido)methyl)piperidine-1-carboxylate (intermediate 3.1). White foam, MS: 513.5 (M+H)+.

Example 14

[4-(Trifluoromethoxy)phenyl]methyl 2-((1H-triazol-4-ylmethyl)carbamoyl)-2,7-diazaspiro[3.5]nonane-7-carboxylate

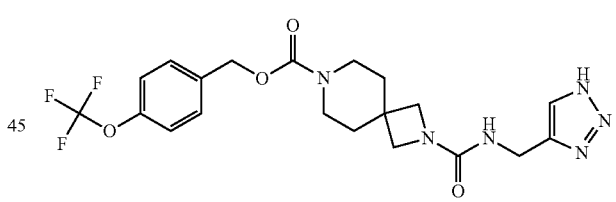

A solution of triphosgene (29 mg, 97 mmol) in ethyl acetate (5 mL) was added dropwise over a period of 5 min to a solution of 4-(trifluoromethoxy)benzyl 2,7-diazaspiro[3.5]nonane-7-carboxylate (intermediate 1.27; 67 mg, 195 mmol) in tetrahydrofuran (5 mL) at room temperature. The reaction mixture was heated at reflux for 2 h, then concentrated under vacuum. The residue was taken up in tetrahydrofuran (7 mL), then (1H-1,2,3-triazol-4-yemethanamine hydrochloride (26.2 mg, 195 mmol) and triethylamine (98.4 mg, 973 mmol) were added at room temperature. After 15 h the reaction mixture was partitioned between water and ethyl acetate, the organic layer was dried over sodium sulfate, filtered, and evaporated. Chromatography (silica gel; dichloromethane-methanol gradient) produced the title compound (35 mg, 38%). White foam, MS: 469.2 (M+H)+.

Example 14.1

[2-Fluoro-4-(trifluoromethoxy)phenyl]methyl 2-((1H-triazol-4-ylmethyl)carbamoyl)-2,7-diazaspiro[3.5]nonane-7-carboxylate

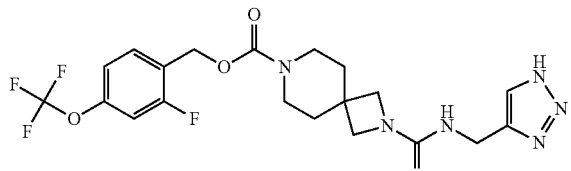

The title compound was produced in analogy to example 14 from 2-fluoro-4-(trifluoromethoxy)benzyl 2,7-diazaspiro[3.5]nonane-7-carboxylate (intermediate 1.28) and (1H-1,2,3-triazol-4-yl)methanamine hydrochloride. White foam, MS: 487.2 (M+H)$^+$.

Examples 15A and 15B (−)-2-Fluoro-4-(trifluoromethoxy)benzyl 2-(4,5,6,7-tetrahydro-1H-benzo[d][1,2,3]triazole-5-carbonyl)-2,7-diazaspiro[3.5]nonane-7-carboxylate and (+)-2-fluoro-4-(trifluoromethoxy)benzyl 2-(4,5,6,7-tetrahydro-1H-benzo[d][1,2,3]triazole-5-carbonyl)-2,7-diazaspiro[3.5]nonane-7-carboxylate

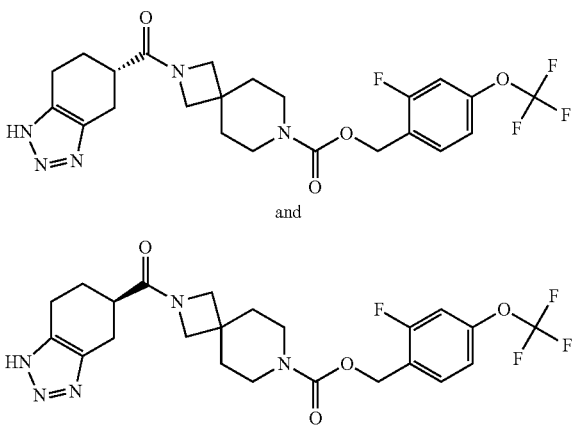

Racemic 2-fluoro-4-(trifluoromethoxy)benzyl 2-(4,5,6,7-tetrahydro-1H-benzo[d][1,2,3]triazole-5-carbonyl)-2,7-diazaspiro[3.5]nonane-7-carboxylate (example 12.36; 28 mg, 55 µmol) was separated by preparative HPLC using a Chiralpak AD column as the stationary phase and heptane/ethanol 3:2 as the eluent. This produced the faster eluting (−)-enantiomer (example 15A; 9 mg, 31%, light yellow foam, MS: 512.5 (M+H)$^+$) and the slower eluting (+)-enantiomer (example 15B, 10 mg, 34%, light yellow foam, MS: 512.5 (M+H)$^+$).

Examples 16A and 16B (S)-[2-Fluoro-4-(trifluoromethyl)phenyl]methyl 2-[4,5,6,7-tetrahydro-1H-benzotriazole-5-carbonyl]-2,7-diazaspiro[3.5]nonane-7-carboxylate and (R)-[2-fluoro-4-(trifluoromethyl)phenyl]methyl 2-[4,5,6,7-tetrahydro-1H-benzotriazole-5-carbonyl]-2,7-diazaspiro[3.5]nonane-7-carboxylate

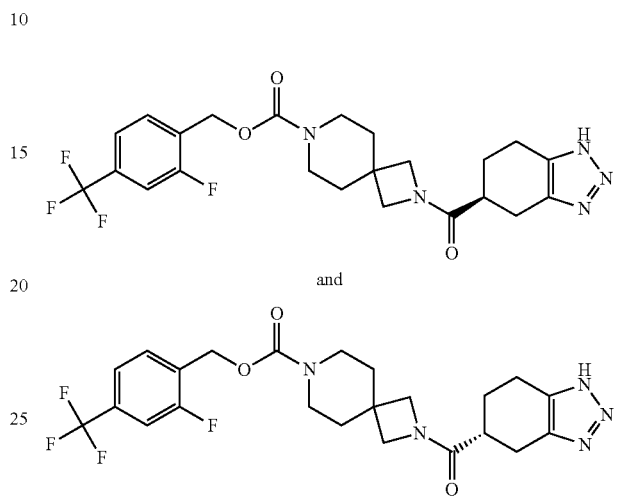

Racemic [2-fluoro-4-(trifluoromethyl)phenyl]methyl 2-[4,5,6,7-tetrahydro-1H-benzotriazole-5-carbonyl]-2,7-diazaspiro[3.5]nonane-7-carboxylate (example 12.36; 35 mg, 71 mmol) was separated by preparative HPLC using a Chiralpak AD column as the stationary phase and heptane/ethanol 3:2 as the eluent. This produced the faster eluting enantiomer (example 16A; 2 mg, 5%, light yellow foam, MS: 496.2 (M+H)$^+$) and the slower eluting enantiomer (example 16B, 3 mg, 8%, light yellow foam, MS: 496.2 (M+H)$^+$).

Intermediates

General Procedure A: Amide Coupling, Method 1

To a solution of the spirocyclic amine (starting material 1, 1 mmol) in N,N-dimethylformamide (5 mL) were added the carboxylic acid (starting material 2, 1.05 mmol), 4-methylmorpholine (4 mmol), and O-(7-azabenzotriazol-1-yl)-N,N,N',N'-tetramethyluronium hexafluoro-phosphate (1.5 mmol). The reaction mixture was stirred for 18 h at ambient temperature and was then partitioned between ethyl acetate and 1 M aqueous hydrochloric acid solution. The organic layer was washed with brine, dried over magnesium sulfate, filtered and evaporated in vacuo. The residue was taken up in toluene, concentrated in vacuo, and chromatographed on silica gel, using a gradient of dichloromethane to dichloromethane/methanol/25% aq. ammonia solution 90:10:0.25 to afford the amide intermediate as colorless solid, foam or oil.

General Procedure B: Ring Closure Reaction

To a light yellow suspension of the 4-amino-3-hydroxybenzamide derivative (1 mmol, obtained according to general procedure A) in tetrahydrofuran (8 mL) was added dropwise a solution of N,N'-carbonyldiimidazole (1.2 mmol) in tetrahydrofuran (4 mL). Then after 16 h the reaction mixture was partitioned between water and ethyl acetate. The organic layer was washed with brine, dried over magnesium sulfate, filtered and evaporated in vacuo. The residue was triturated in heptane/ethyl acetate 1:1 to produce the 2,3-dihydrobenzo[d]oxazole intermediate as a white solid.

General Procedure C: Amide Coupling, Method 2

A solution of the carboxylic acid (starting material 1, 1 mmol), the amine (starting material 2, 1 mmol), 1-hydroxybenzotriazole hydrate (1.3 mmol) and 1-(3-dimethylaminopropyl)-3-ethylcarbodiimide hydrochloride (1.1 mmol) in N,N-dimethylformamide (6 mL) was stirred at room temperature for 16 hours and was then partitioned between water and ethyl acetate. The organic layer was washed with brine, dried over sodium sulfate, filtered and evaporated in vacuo. The residue was taken up in toluene, concentrated in vacuo, and chromatographed on silica gel, using a dichloromethane-methanol gradient, producing the amide intermediate as an off-white foam.

General Procedure D: Reductive Amination

To a light yellow solution of the ketone (starting material 1, 1 mmol) amine (starting material 2, 1 mmol) in tetrahydrofuran (5 ml) were added sodium triacetoxyborohydride (1.5 mmol) and acetic acid (1.5 mmol) at room temperature. Then after 15 h the reaction mixture was partitioned between sat. aq. sodium hydrogencarbonate solution and ethyl acetate. The organic layer was washed with brine, dried over magnesium sulfate, filtered, and evaporated. The residue was triturated with ethyl acetate/heptane 4:1 to produce the secondary amine intermediate as a white solid.

General Procedure E: Carbamate Synthesis, Method 1

To a solution of the benzyl alcohol (starting material 2, 1 mmol) in dichloromethane (5 ml) was added N,N'-carbonyldiimidazole (1.05 mmol) at room temperature. The mixture was stirred for 3 h at ambient temperature, followed by addition of the spirocyclic amine (starting material 1, 1 mmol) and triethylamine (1 mmol). Then after 18 h the reaction mixture was partitioned between dichloromethane and brine. The organic layer was washed with brine, dried over magnesium sulfate, filtered and evaporated in vacuo. The residue was chromatographed on silica gel, using a heptane/ethyl acetate gradient, producing the benzyl carbamate intermediate as a colorless oil.

General Procedure F: Carbamate Synthesis, Method 2

The chloroformate ester (starting material 2, 1.2 mmol) was added to a solution of the spirocyclic amine (starting material 1, 1 mmol) and N-ethyldiisopropylamine (3 mmol) in dichloromethane (10 mL) at 0° C. Then after 2 h the ice bath was removed and stirring was continued at room temperature. After 16 h the reaction mixture was partitioned between water and ethyl acetate. The organic layer was washed with brine, dried over sodium sulfate, filtered and evaporated in vacuo. The residue was chromatographed on silica gel, using a heptane-ethyl acetate gradient, producing the benzyl carbamate intermediate as a colorless oil.

General Procedure G: N-Sulfonylation

To a solution or suspension of the spirocyclic amine (starting material 1, 1 mmol) and triethylamine (3 mmol) in tetrahydrofuran (5 mL) was added a solution of the sulfonyl chloride (starting material 2, 1.2 mmol) in tetrahydrofuran (1 mL) at 0° C. The ice bath was removed and then after 16 h the reaction mixture was partitioned between 1 M aq. hydrochloric acid solution and ethyl acetate. The organic layer was washed with sat. aq. sodium hydrogencarbonate solution and brine, dried over magnesium sulfate, filtered and evaporated. The residue was optionally triturated in heptane/ethyl acetate 1:1 to produce the sulfonamide intermediate.

General Procedure H: Boc-Deprotection, Method 1

The tert-butyl carbamate product from general procedure A, B, C, D, E, F, or G (100 mg) was combined with hydrogen chloride solution (5M to 6M in 2-propanol, 1 mL) and was stirred at ambient temperature for 18 h. Then the reaction mixture was evaporated and the residue was precipitated from ethyl acetate to give intermediate 1 as the hydrochloride salt.

General Procedure I: Boc-Deprotection, Method 2

Trifluoroacetic acid (10 mmol) was added at room temperature to a solution of the tert-butyl carbamate product from general procedure A, B, C, D, E, F, or G (1 mmol) in dichloromethane (10 mL). Then after 2 h the reaction mixture was concentrated in vacuo to produce intermediate 1 as the trifluoroacetate salt.

General procedure J: Boc-Deprotection, Method 3

Trifluoroacetic acid (10 mmol) was added at room temperature to a solution of the tert-butyl carbamate product from general procedure A, B, C, D, E, F, or G (1 mmol) in dichloromethane (10 mL). Then after 2 h the reaction mixture was partitioned between 2 M aq. sodium hydroxide solution and chloroform. The organic layer was dried over sodium sulfate, filtered and concentrated to produce intermediate 1 as the free base.

Intermediates 1

The intermediates 1.1-1.25 and 1.26 to 1.30 were prepared from starting material 1 and starting material 2 according to one or more of the general procedures A-G (step 1), followed by Boc-deprotection according to the general procedures H-J (step 2).

| No. | Systematic Name | Starting material 1 | Starting material 2 | MS, m/e | General procedures Step 1 | Step 2 |
|---|---|---|---|---|---|---|
| 1.1 | (1H-benzo[d][1,2,3]-triazol-5-yl)(2,7-diazaspiro[4.4]nonan-2-yl)methanone hydrochloride | 2,7-diazaspiro[4.4]nonane-2-carboxylic acid tert-butyl ester (CAS-RN 236406-49-8) | 1H-benzo[d][1,2,3]-triazole-5-carboxylic acid | 272.4 (M + H)+ | A | H |
| 1.2 | (1H-benzo[d][1,2,3]-triazol-5-yl)(2,7-diazaspiro[3.5]nonan-2-yl)methanone hydrochloride | 2,7-diazaspiro[3.5]nonane-7-carboxylic acid tert-butyl ester (CAS-RN 896464-16-7) | 1H-benzo[d][1,2,3]-triazole-5-carboxylic acid | 272.5 (M + H)+ | A | H |
| 1.3 | 3-(3,5-dichlorophenyl)-1-(2,7-diazaspiro[3.5]-nonan-7-yl)propan-1-one hydrochloride | tert-butyl 2,7-diazaspiro[3.5]nonane-2-carboxylate (CAS-RN 236406-55-6) | 3-(3,5-dichlorophenyl)-propanoic acid | 327.2 (M + H)+ | A | H |

-continued

| No. | Systematic Name | Starting material 1 | Starting material 2 | MS, m/e | General procedures Step 1 | Step 2 |
|---|---|---|---|---|---|---|
| 1.4 | (1H-benzo[d][1,2,3]-triazol-5-yl)(2,7-diazaspiro[4.5]decan-2-yl)methanone 2,2,2-trifluoroacetate | tert-butyl 2,7-diazaspiro[4.5]decane-7-carboxylate (CAS-RN 236406-61-4) | 1H-benzo[d][1,2,3]-triazole-5-carboxylic acid | 286.5 (M + H)+ | A | I |
| 1.5 | N-(2-azaspiro[3.3]heptan-6-yl)-1H-benzo[d]-[1,2,3]triazole-5-carboxamide 2,2,2-trifluoroacetate | tert-butyl 6-amino-2-azaspiro[3.3]heptane-2-carboxylate (CAS-RN 1211586-09-2) | 1H-benzo[d][1,2,3]-triazole-5-carboxylic acid | 370.6 (M − H)− | A | I |
| 1.6 | 1-(6-amino-2-azaspiro[3.3]heptan-2-yl)-3-(3,5-dichlorophenyl)-propan-1-one | tert-butyl 2-azaspiro[3.3]heptan-6-ylcarbamate (CAS-RN 1118786-85-8) | 3-(3,5-dichlorophenyl)-propanoic acid | 313.1 (M + H)+ | A | J |
| 1.7 | 1-(6-amino-2-azaspiro[3.3]heptan-2-yl)-4-phenylbutan-1-one | tert-butyl 2-azaspiro[3.3]heptan-6-ylcarbamate (CAS-RN 1118786-85-8) | 4-phenylbutanoic acid | 259.1 (M + H)+ | A | J |
| 1.8 | 6-(2,7-diazaspiro[3.5]nonane-2-carbonyl)-benzo[d]oxazol-2(3H)-one hydrochloride | 2,7-diazaspiro[3.5]-nonane-7-carboxylic acid tert-butyl ester (CAS-RN 896464-16-7) | 4-amino-3-hydroxybenzoic acid | 288.4 (M + H)+ | A, then B | H |
| 1.9 | 6-amino-N-(1H-benzo[d][1,2,3]triazol-5-yl)spiro[3.3]heptane-2-carboxamide 2,2,2-trifluoroacetate | 6-(tert-butoxy-carbonylamino)-spiro[3.3]heptane-2-carboxylic acid (CAS-RN 1087798-38-6) | 1H-benzo[d][1,2,3]triazol-5-amine | 272.4 (M + H)+ | C | I |
| 1.10 | 3,5-dichlorobenzyl 2,8-diazaspiro[4.5]decane-2-carboxylate hydrochloride | tert-butyl 2,8-diazaspiro[4.5]decane-8-carboxylate (CAS-RN 236406-39-6) | (3,5-dichlorophenyl)-methanol | 343.4 (M + H)+ | E | H |
| 1.11 | 6-(7-azaspiro[3.5]-nonan-2-ylamino)-benzo[d]oxazol-2(3H)-one trihydrochloride | 7-tert-butoxycarbonyl-7-azaspiro[3.5]nonan-2-one (CAS-RN 203661-69-2) | 6-aminobenzo[d]oxazol-2(3H)-one | 274.3 (M + H)+ | D | H |
| 1.12 | 3,5-dichlorobenzyl 2-azaspiro[3.3]heptan-6-ylcarbamate | tert-butyl 6-amino-2-azaspiro[3.3]heptane-2-carboxylate (CAS-RN 1211586-09-2) | (3,5-dichlorophenyl)-methanol | 315.4 (M + H)+ | E | J |
| 1.13 | 3,5-dichlorobenzyl 2,7-diazaspiro[3.5]-nonane-2-carboxylate hydrochloride | 2,7-diazaspiro[3.5]-nonane-7-carboxylic acid tert-butyl ester (CAS-RN 896464-16-7) | (3,5-dichlorophenyl)-methanol | 329.4 (M + H)+ | E | H |
| 1.14 | 3,5-dichlorobenzyl 2,6-diazaspiro[3.4]-octane-2-carboxylate hydrochloride | 2,6-diazaspiro[3.4]-octane-2-carboxylic acid tert-butyl ester (CAS-RN 885270-84-8) | (3,5-dichlorophenyl)-methanol | 315.4 (M + H)+ | E | H |
| 1.15 | 3-chloro-5-(methyl-sulfonyl)benzyl 2,7-diazaspiro[3.5]-nonane-7-carboxylate hydrochloride | tert-butyl 2,7-diazaspiro[3.5]-nonane-2-carboxylate (CAS-RN 236406-55-6) | (3-chloro-5-(methylsulfonyl)-phenyl)methanol (intermediate 2.1) | 373.4 (M + H)+ | E | H |
| 1.16 | 3-chlorobenzyl 2,7-diazaspiro[3.5]-nonane-7-carboxylate hydrochloride | tert-butyl 2,7-diazaspiro[3.5]-nonane-2-carboxylate (CAS-RN 236406-55-6) | (3-chlorophenyl)-methanol | 295.3 (M + H)+ | E | H |
| 1.17 | 4-chlorobenzyl 2,7-diazaspiro[3.5]-nonane-7-carboxylate hydrochloride | tert-butyl 2,7-diazaspiro[3.5]-nonane-2-carboxylate (CAS-RN 236406-55-6) | (3-chlorophenyl)-methanol | 295.3 (M + H)+ | E | H |

-continued

| No. | Systematic Name | Starting material 1 | Starting material 2 | MS, m/e | General procedures Step 1 | Step 2 |
|---|---|---|---|---|---|---|
| 1.18 | 3,5-dichlorobenzyl 2,7-diazaspiro[3.5]-nonane-7-carboxylate hydrochloride | tert-butyl 2,7-diazaspiro[3.5]-nonane-2-carboxylate (CAS-RN 236406-55-6) | (3,5-dichlorophenyl)methanol | 329.1 (M + H)+ | E | H |
| 1.19 | 3,5-dichlorobenzyl 6-amino-2-azaspiro[3.3]heptane-2-carboxylate | tert-butyl 2-azaspiro[3.3]heptan-6-ylcarbamate (CAS-RN 1118786-85-8) | 3,5-dichlorobenzyl carbonochloridate (CAS-RN 1175526-48-3) | 315.4 (M + H)+ | F | J |
| 1.20 | benzyl 2-azaspiro[3.3]heptan-6-ylcarbamate | tert-butyl 6-amino-2-azaspiro[3.3]heptane-2-carboxylate (CAS-RN 1211586-09-2) | benzyl chloroformate | 247.3 (M + H)+ | F | J |
| 1.21 | benzyl 6-amino-2-azaspiro[3.3]heptane-2-carboxylate | tert-butyl 2-azaspiro[3.3]heptan-6-ylcarbamate (CAS-RN 1118786-85-8) | benzyl chloroformate | 247.2 (M + H)+ | F | J |
| 1.22 | 6-(2,7-diazaspiro[3.5]-nonan-2-ylsulfonyl)-benzo[d]oxazol-2(3H)-one hydrochloride | 2,7-diazaspiro[3.5]-nonane-7-carboxylic acid tert-butyl ester (CAS-RN 896464-16-7) | 2-oxo-2,3-dihydrobenzo[d]oxazole-6-sulfonyl chloride | 360.3 (M + H)+ | G | H |
| 1.23 | 3-fluoro-5-(trifluoro-methoxy)benzyl 2,7-diazaspiro[4.5]decane-2-carboxylate 2,2,2-trifluoroacetate | tert-butyl 2,7-diazaspiro[4.5]decane-7-carboxylate (CAS-RN 236406-61-4) | (3-fluoro-5-(trifluoromethoxy)-phenyl)methanol | 377.5 (M + H)+ | E | I |
| 1.24 | N-((1H-1,2,3-triazol-5-yl)methyl)-7-azaspiro[3.5]nonane-2-carboxamide 2,2,2-trifluoroacetate | 7-(tert-butoxycarbonyl)-7-azaspiro[3.5]nonane-2-carboxylic acid (CAS-RN 873924-12-0) | (1H-1,2,3-triazol-4-yl)methanamine hydrochloride | 250.5 (M + H)+ | C | I |
| 1.25 | 7-(3-chlorophenethyl-sulfonyl)-2,7-diazaspiro[3.5]nonane | tert-butyl 2,7-diazaspiro[3.5]nonane-2-carboxylate (CAS-RN 236406-55-6) | 2-(3-chlorophenyl)-ethanesulfonyl chloride | 329.4 (M + H)+ | G | J |
| 1.26 | 2,7-diaza-spiro[3.5]nonan-7-yl-(4,5,6,7-tetrahydro-1H-benzo[d]-[1,2,3]triazol-5-yl)methanone 2,2,2-trifluoroacetate | tert-butyl 2,7-diaza-spiro[3.5]nonane-2-carboxylate (CAS-RN 236406-55-6) | 4,5,6,7-tetrahydro-1H-benzo[d]-[1,2,3]triazole-5-carboxylic acid (CAS-RN 33062-47-4) | 276.5 (M + H)+ | A | I |
| 1.27 | 4-(trifluoromethoxy)-benzyl 2,7-diazaspiro[3.5]nonane-7-carboxylate | tert-butyl 2,7-diazaspiro[3.5]nonane-2-carboxylate (CAS-RN 236406-55-6) | (4-(trifluoromethoxy)phenyl)-methanol | 345.1 (M + H)+ | E | J |
| 1.28 | 2-fluoro-4-(trifluoromethoxy)-benzyl 2,7-diazaspiro[3.5]nonane-7-carboxylate | tert-butyl 2,7-diazaspiro[3.5]nonane-2-carboxylate (CAS-RN 236406-55-6) | (2-fluoro-4-(trifluoromethoxy)-phenyl)methanol (CAS-RN | 363.5 (M + H)+ | E | J |
| 1.29 | 2,7-diazaspiro[3.5]nonan-2-yl(4,5,6,7-tetrahydro-1H-benzo[d]-[1,2,3]triazol-5-yl)methanone hydrochloride | 2,7-diazaspiro[3.5]nonane-7-carboxylic acid tert-butyl ester (CAS-RN 896464-16-7) | 4,5,6,7-tetrahydro-1H-benzo[d]-[1,2,3]triazole-5-carboxylic acid (CAS-RN 33062-47-4) | 276.5 (M + H)+ | A | H |
| 1.30 | 1-(2,7-diazaspiro[3.5]nonan-7-yl)-3-(4-(trifluoro-methoxy)-phenyl)propan-1-one | tert-butyl 2,7-diazaspiro[3.5]nonane-2-carboxylate (CAS-RN 236406-55-6) | 3-(4-(trifluoromethoxy)-phenyl)propanoic acid | 343.5 (M + H)+ | A | J |

Intermediate 2

(4-Chloro-3-(methylsulfonyl)phenyl)methanol

To a solution of 4-chloro-3-(methylsulfonyl)benzoic acid (500 mg, 2.13 mmol) in tetrahydrofuran (5 ml) was added slowly borane-tetrahydrofuran complex solution (1 M in tetrahydrofuran, 5.33 ml, 5.33 mmol) at 0° C. The ice-bath was removed after 2 h and the reaction mixture was stirred at room temperature overnight. After careful addition of methanol (4 mL), the reaction mixture was evaporated. The residue was partitioned between water and ethyl acetate. The organic layer was washed with brine, dried over magnesium sulfate, filtered and evaporated. Chromatography (silica gel; gradient ethyl acetate/heptane 1:1 to ethyl acetate) afforded the title compound (455 mg, 97%). Colourless gum, MS: 238.0 (M+NH$_4$)$^+$.

Intermediate 2.1

(3-Chloro-5-(methylsulfonyl)phenyl)methanol

The title compound was produced in analogy to intermediate 2 from 3-chloro-5-(methylsulfonyl)-benzoic acid (CAS-RN 151104-63-1). White solid, MS: 221.1 (M+H)$^+$.

Intermediate 3

4-(Trifluoromethoxy)benzyl 4-(chloromethyl)-4-((4,5,6,7-tetrahydro-1H-[1,2,3]triazolo[4,5-c]pyridine-5-carboxamido)methyl)piperidine-1-carboxylate Triethylamine (20.3 mg, 200 μmol) and N,N'-disuccinimidyl carbonate (51.3 mg, 200 μmol) were added to a solution of (4-(trifluoromethoxy)phenyl)methanol (38.5 mg, 200 μol) in acetonitrile (4 mL) at room temperature. After 3½ h N-((4-(chloromethyl)piperidin-4-yl)methyl)-6,7-dihydro-1H-[1,2,3]triazolo[4,5-c]pyridine-5(4H)-carboxamide hydrochloride (intermediate 4; 70 mg, 200 μmol) and triethylamine (40.6 mg, 401 μmol) were added, then after 65 h the reaction mixture was partitioned between water and ethyl acetate. The organic layer was washed with brine, dried over sodium sulfate, filtered, and evaporated. The crude material was purified by flash chromatography (silica gel, heptane-ethyl acetate gradient, then dichloromethane/methanol 19:1) to produce the title compound (50 mg, 46%). White solid, MS: 531.5 (M+H)$^+$.

Intermediate 3.1

2-Fluoro-4-(trifluoromethoxy)benzyl 4-(chloromethyl)-4-((4,5,6,7-tetrahydro-1H-[1,2,3]triazolo[4,5-c]pyridine-5-carboxamido)methyl)piperidine-1-carboxylate The title compound was produced in analogy to intermediate 3 from N-((4-(chloromethyl)-piperidin-4-yl)methyl)-6,7-dihydro-1H-[1,2,3]triazolo[4,5-c]pyridine-5(4H)-carboxamide hydrochloride (intermediate 4) and (2-fluoro-4-(trifluoromethoxy)phenyl)methanol (CAS-RN 1240257-07-1). White solid, MS: 549.5 (M+H)$^+$.

Intermediate 4

N-((4-(Chloromethyl)piperidin-4-yl)methyl)-6,7-dihydro-1H-[1,2,3]triazolo[4,5-c]pyridine-5(4H)-carboxamide hydrochloride Step 1: tert-butyl 2-(chlorocarbonyl)-2,7-diazaspiro[3.5]nonane-7-carboxylate To a colourless solution of tert-butyl 2,7-diazaspiro[3.5]nonane-7-carboxylate (CAS-RN 896464-16-7; 300 mg, 1.33 mmol) and pyridine (315 mg, 3.98 mmol) in dichloromethane (6 mL) was added dropwise over a period of 5 min a solution of triphosgene (157 mg, 530 μmol) in dichloromethane (3 mL) at 0° C. After 30 minutes the ice bath was removed and the mixture was warmed up to room temperature over 2 hours. The reaction mixture was partitioned between 2 M aq. hydrochloric acid solution and ethyl acetate, the organic layer was washed with brine, dried over sodium sulfate, filtered, and evaporated to produce the title compound (290 mg, 72%), which was directly used in the next step.

Step 2: tert-Butyl 2-(4,5,6,7-tetrahydro-1H-[1,2,3]-triazolo[4,5-c]pyridine-5-carbonyl)-2,7-diazaspiro[3.5]nonane-7-carboxylate To a colourless solution of 4,5,6,7-tetrahydro-1H-[1,2,3]triazolo[4,5-c]pyridine (CAS-RN 706757-05-3; 123 mg, 987 μmol) and N,N-diisopropylethylamine (255 mg, 1.97 mmol) in N,N-dimethylformamide (4 mL) was added a solution of tert-butyl 2-(chlorocarbonyl)-2,7-diazaspiro[3.5]nonane-7-carboxylate (285 mg, 987 μmol) in dichloromethane (8 mL) dropwise over a period of 10 minutes at room temperature. After 18 h the reaction mixture was partitioned between dichloromethane and sat. aq. ammonium chloride solution. The organic layer was washed with brine, dried over sodium sulfate, filtered, and evaporated. Chromatography (silica gel; heptane-ethyl acetate gradient, then dichloromethane/methanol 19:1) produced the title compound (212 mg, 56%). Light yellow foam, MS: 321.5 (M+H-isobutene)$^+$.

Step 3: N-((4-(Chloromethyl)piperidin-4-yl)methyl)-6,7-dihydro-1H-[1,2,3]triazolo[4,5-c]pyridine-5(4H)-carboxamide hydrochloride Hydrogen chloride solution (5-6 M in 2-propanol, 2.4 mL, 12 mmol) was added at room temperature to a solution of tert-butyl 2-(4,5,6,7-tetrahydro-1H-[1,2,3]triazolo[4,5-c]pyridine-5-carbonyl)-2,7-diazaspiro[3.5]nonane-7-carboxylate (208 mg, 553 μmol) in 2-propanol (4 mL). After 3½ h the reaction mixture was evaporated, and the residue was taken up in ethyl acetate (5 mL) and ethanol (3 drops), then after 30 min the precipitate was collected by filtration and dried to produce the title compound (200 mg, 100%). White solid, MS: 313.5 (M+H)$^+$.

Intermediate 5

3-Isopropyl-4-(2-oxo-2-(2,7-diazaspiro[3.5]nonan-7-yl)ethoxy)benzonitrile

Step 1: tert-Butyl 7-(2-bromoacetyl)-2,7-diazaspiro[3.5]nonane-2-carboxylate

To a suspension of tert-butyl 2,7-diazaspiro[3.5]nonane-2-carboxylate (CAS-RN 236406-55-6; 500 mg, 2.21 mmol) and triethylamine (291 mg, 2.87 mmol) in dichloromethane (15 mL) was added 2-bromoacetyl chloride (348 mg, 2.21 mmol), then the reaction mixture was allowed to reach room temperature over 16 h and partitioned between ice water and ethyl acetate The organic layer was washed with brine, dried over sodium sulfate, filtered, and evaporated. The crude material was purified by flash chromatography (silica gel; heptane-ethyl acetate gradient) to produce the title compound (531 mg, 68%). Light brown gum, MS: 247.4 (M−Me$_3$COCO+H)$^+$.

Step 2: tert-Butyl 7-(2-(4-cyano-2-isopropylphenoxy)acetyl)-2,7-diazaspiro[3.5]nonane-2-carboxylate Caesium carbonate (375 mg, 1.15 mmol) was added at room temperature to a solution of tert-butyl 7-(2-bromoacetyl)-2,7-diazaspiro[3.5]nonane-2-carboxylate (200 mg, 576 μmol) and 4-hydroxy-3-isopropylbenzonitrile (CAS-RN 46057-54-9; 92.8 mg, 576 μmol) in N,N-dimethylformamide (5 mL). After 18 h the reaction mixture was partitioned between water and ethyl acetate, the organic layer was washed with brine, dried over sodium sulfate, filtered, and evaporated. The crude material was purified by flash chromatography (silica gel, heptane-ethyl acetate gradient) to produce the title compound (197 mg, 78%). White foam, MS: 372.6 (M−isobutene+H)$^+$.

Step 3: 3-Isopropyl-4-(2-oxo-2-(2,7-diazaspiro[3.5]nonan-7-yl)ethoxy)benzonitrile Trifluoroacetic acid (500 mg, 4.4 mmol) was added dropwise to a solution of tert-butyl 7-(2-(4-cyano-2-isopropylphenoxy)acetyl)-2,7-diazaspiro[3.5]nonane-2-carboxylate (188 mg, 440 μmol) in dichloromethane (5 mL). After 4 h the reaction mixture was basified with sat. aq. sodium hydrogencarbonate solution and extracted with ethyl acetate. The organic layer was washed with brine, dried over sodium sulfate, filtered, and evaporated to afford the title compound (69 mg, 47%). Light yellow foam, MS: 328.6 (M+H)$^+$.

Intermediate 5.1

2-(4-Chloro-2-isopropylphenoxy)-1-(2,7-diazaspiro[3.5]nonan-7-yl)ethanone

The title compound was produced in analogy to intermediate 5, replacing 4-hydroxy-3-isopropylbenzonitrile in step 2 by 4-chloro-2-isopropylphenol. Light yellow gum, MS: 337.5 (M+H)$^+$.

The invention claimed is:
1. A compound of formula (I)

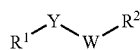
(I)

wherein
$R^1$ is phenylalkyl substituted with $R^8$, $R^9$ and $R^{10}$;
$R^2$ is —C(O)—$R^3$;
Y is —OC(O)—;
W is

or

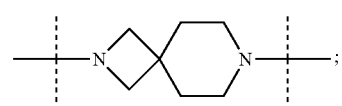

$R^3$ is;

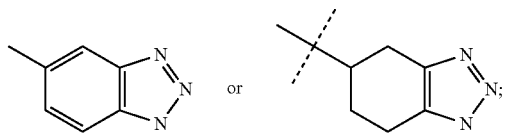

and
$R^8$, $R^9$, and $R^{10}$ are independently selected from H, alkyl, hydroxyalkyl, haloalkyl, cycloalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, haloalkoxyalkyl, alkoxyalkoxy, alkoxyalkoxyalkyl, halogen, hydroxy, cyano, alkylsulfonyl, cycloalkylsulfonyl, substituted aminosulfonyl, substituted amino and substituted aminoalkyl, wherein substituted aminosulfonyl, substituted amino and substituted aminoalkyl are substituted on the nitrogen atom with one to two substituents independently selected from hydrogen, alkyl, cycloalkyl, cycloalkylalkyl, hydroxyalkyl, alkoxyalkyl, alkylcarbonyl and cycloalkylcarbonyl;
or a pharmaceutically acceptable salt thereof.
2. A The compound of claim 1, wherein $R^8$ is haloalkoxy, halogen or alkylsulfonyl.
3. A The compound of claim 1, wherein $R^9$ is alkyl, haloalkyl or halogen.
4. The compound of claim 1, wherein $R^{10}$ is H.
5. The compound of claim 1, selected from:

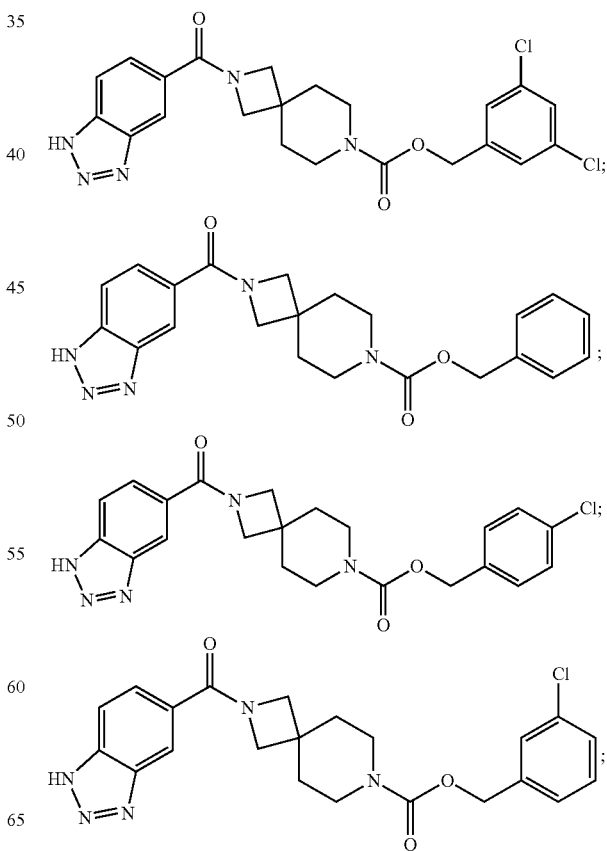

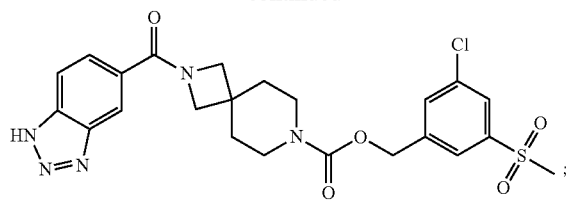
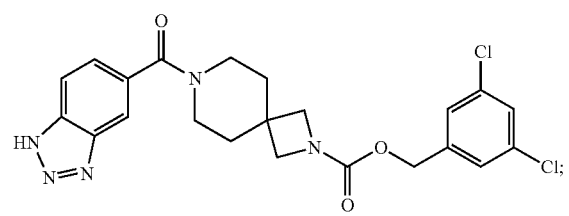
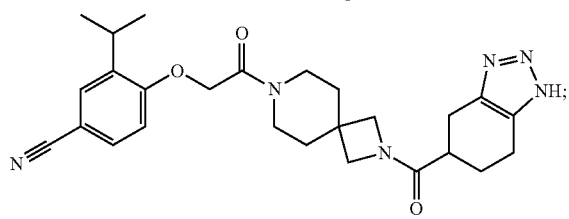
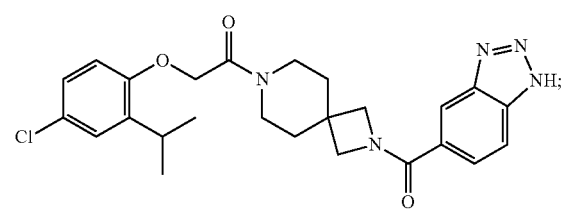
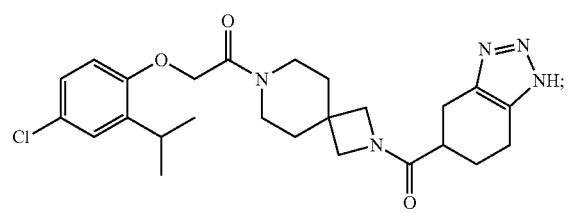
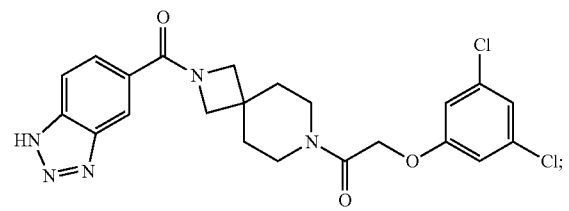
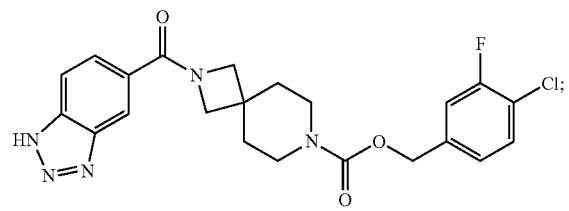
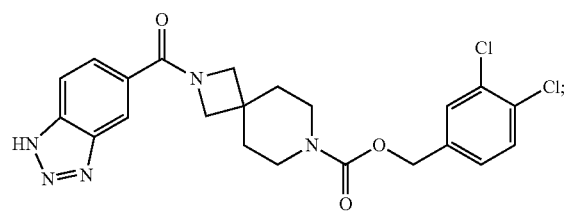
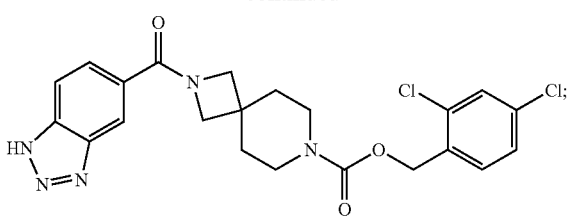
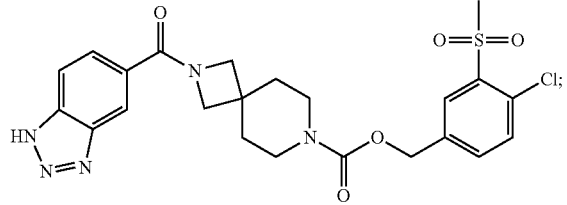
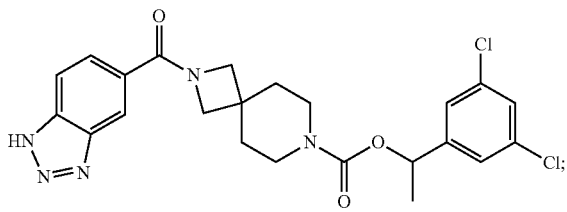
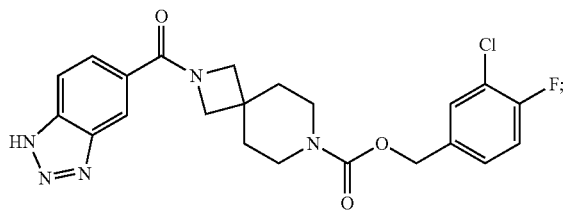
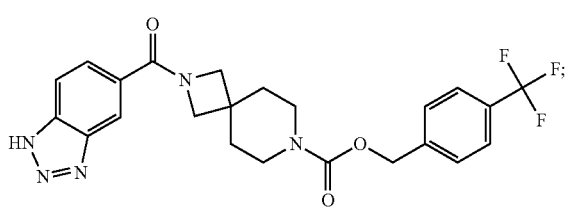
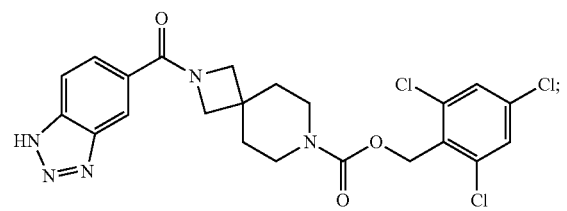
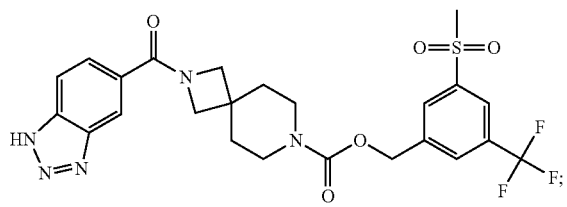 [SMILES: CS(=O)(=O)c1cc(COC(=O)N2CCC3(CC2)CN(C(=O)c2ccc4[nH]nnc4c2)C3)cc(C(F)(F)F)c1]
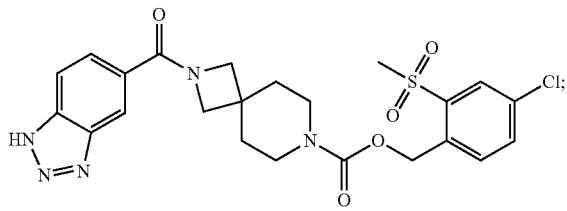

111
-continued
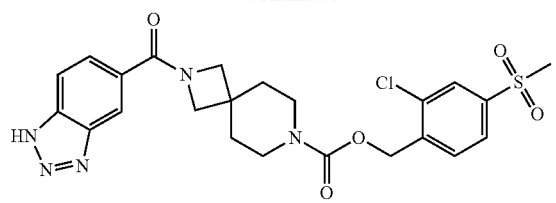 [SMILES: CS(=O)(=O)c1ccc(COC(=O)N2CCC3(CC2)CN(C(=O)c2ccc4[nH]nnc4c2)C3)c(Cl)c1]
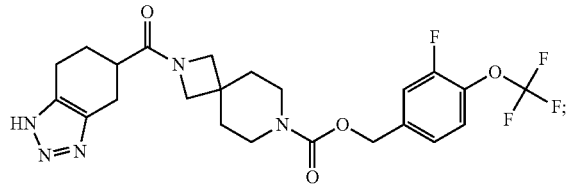
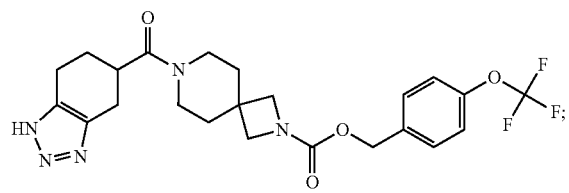
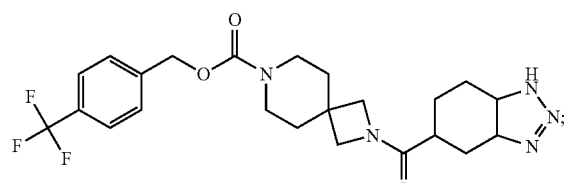
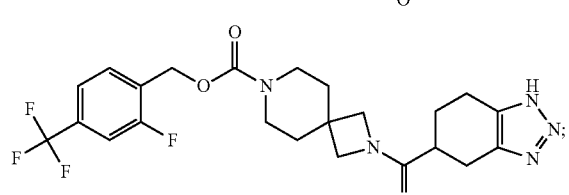
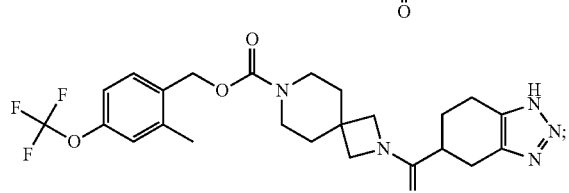
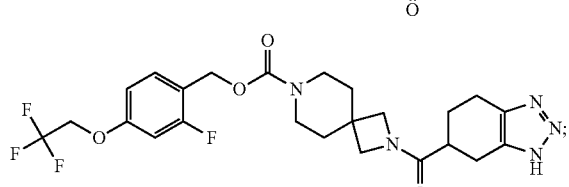
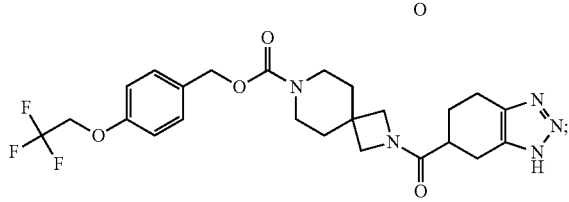
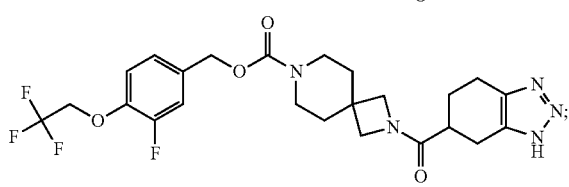
112
-continued
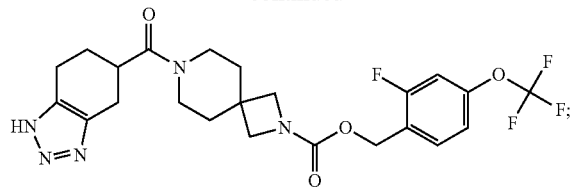
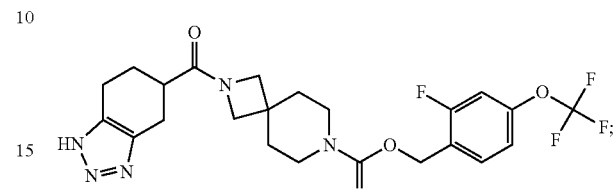
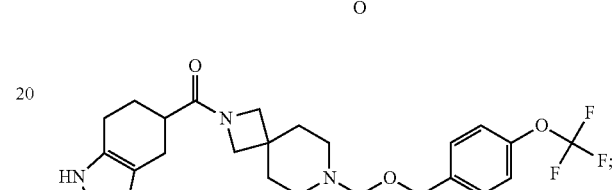
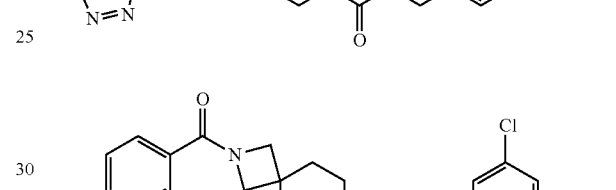
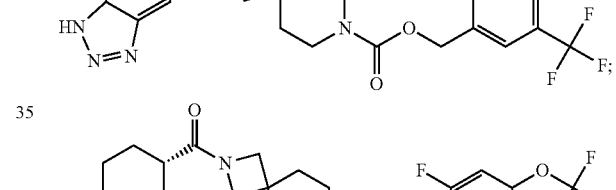
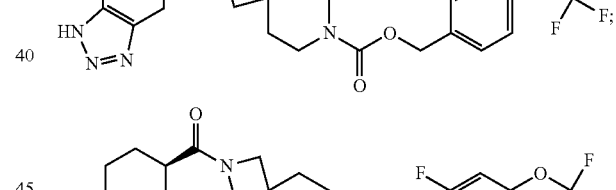
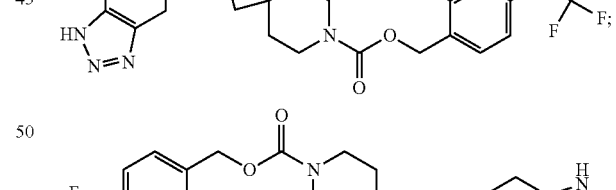
and
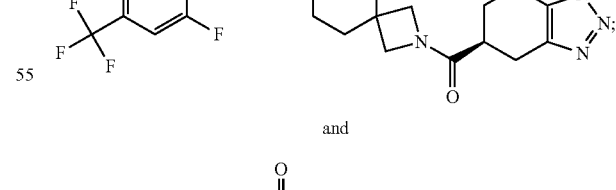

6. The compound of claim 5, selected from:
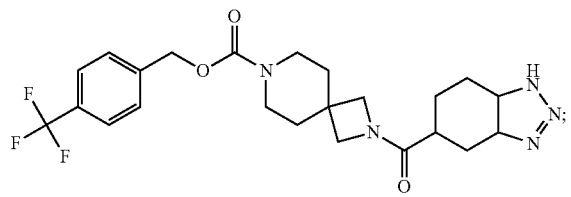
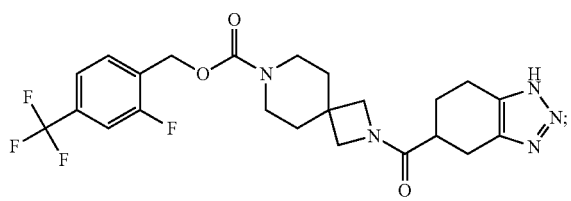
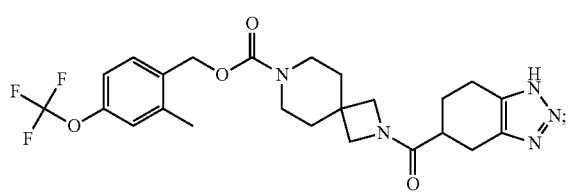
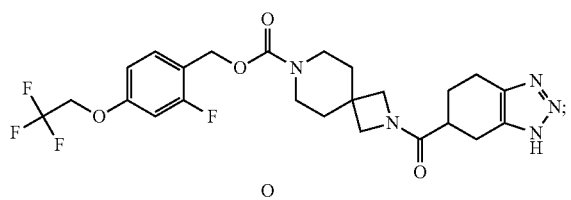
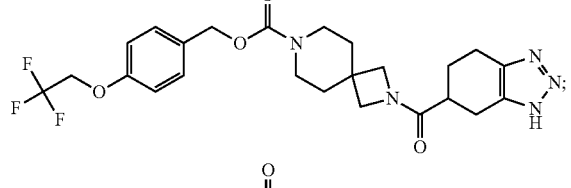
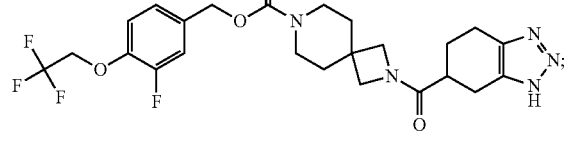
-continued
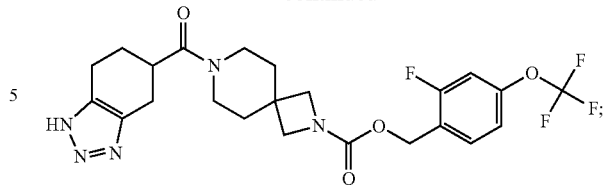
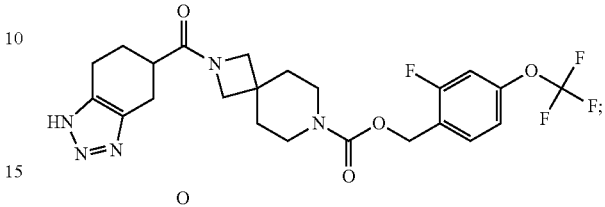
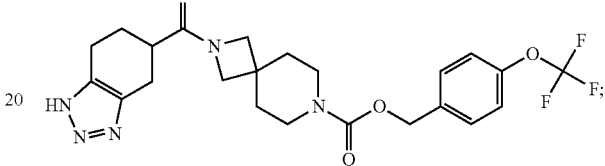
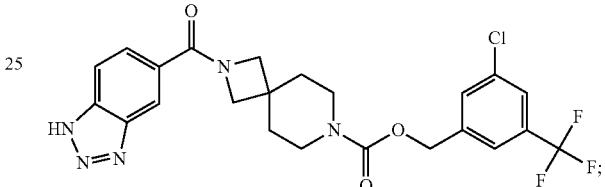
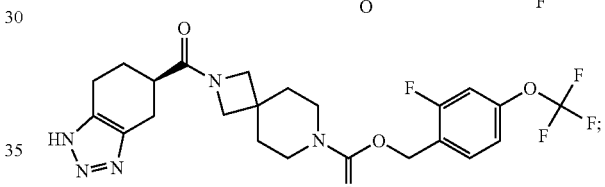
and
* * * * *